United States Patent
Zu et al.

(10) Patent No.: US 12,258,588 B2
(45) Date of Patent: Mar. 25, 2025

(54) FUSION POLYPEPTIDES FOR PRODUCTION OF 7-DEHYDROCHOLESTEROL AND METHODS OF USE THEREOF

(71) Applicant: Hangzhou Enhe Biotechnology Co., Ltd., Zhejiang (CN)

(72) Inventors: Yazhou Zu, Hangzhou (CN); Zhenhua Pang, Hangzhou (CN); Igor Walter Bogorad, Lafayette, CA (US)

(73) Assignee: Hangzhou Enhe Biotechnology Co., Ltd., Zhejiang (CN)

( * ) Notice: Subject to any disclaimer, the term of this patent is extended or adjusted under 35 U.S.C. 154(b) by 0 days.

(21) Appl. No.: 18/919,946

(22) Filed: Oct. 18, 2024

(65) Prior Publication Data
US 2025/0043252 A1 Feb. 6, 2025

Related U.S. Application Data

(63) Continuation of application No. PCT/CN2023/101041, filed on Jun. 19, 2023.

(51) Int. Cl.
| | |
|---|---|
| C12N 9/00 | (2006.01) |
| C12N 9/02 | (2006.01) |
| C12N 9/04 | (2006.01) |
| C12P 33/00 | (2006.01) |

(52) U.S. Cl.
CPC ......... *C12N 9/0071* (2013.01); *C12N 9/0006* (2013.01); *C12N 9/0077* (2013.01); *C12P 33/00* (2013.01); *C12Y 101/01001* (2013.01); *C12Y 101/03004* (2013.01); *C07K 2319/00* (2013.01)

(58) Field of Classification Search
CPC .................... C12N 9/0071; C12N 9/0077
See application file for complete search history.

(56) References Cited

U.S. PATENT DOCUMENTS

| | | |
|---|---|---|
| 7,659,097 B2 | 2/2010 | Renninger et al. |
| 2009/0203102 A1 | 8/2009 | Cervin et al. |
| 2009/0282545 A1 | 11/2009 | Eichelberger et al. |
| 2010/0003716 A1 | 1/2010 | Cervin et al. |
| 2010/0048964 A1 | 2/2010 | Calabria et al. |
| 2010/0297749 A1 | 11/2010 | Aravanis et al. |
| 2011/0045563 A1 | 2/2011 | Melis |
| 2014/0068797 A1 | 3/2014 | Doudna et al. |
| 2014/0315985 A1 | 10/2014 | May et al. |
| 2020/0179452 A1 | 6/2020 | Honkanen et al. |

FOREIGN PATENT DOCUMENTS

| | | |
|---|---|---|
| CN | 103882037 A | 6/2014 |
| CN | 107312787 A | 11/2017 |
| WO | WO 2004/033646 A2 | 4/2004 |
| WO | WO 2009/076676 A2 | 6/2009 |
| WO | WO 2009/132220 A2 | 10/2009 |
| WO | WO 2010/003007 A2 | 1/2010 |
| WO | WO 2011/034863 A1 | 3/2011 |
| WO | WO 2022/270588 A1 | 12/2022 |

OTHER PUBLICATIONS

Berka et al., "The development of gene expression systems for filamentous fungi," Biotechnology Advances, 1989, 7(2):127-154.
CAS No. 434-16-2, "7-Dehydrocholesterol," Sigma-Aldrich, retrieved on Jan. 13, 2025, retrieved from URL <https://www.sigmaaldrich.com/US/en/product/sigma/30800>, 7 pages.
Chen et al., "Fusion protein linkers: Property, design and functionality," Advanced Drug Delivery Reviews, Oct. 2013, 65(10):1357-1369.
International Search Report and Written Opinion in International Appln. No. PCT/CN2023/101041, mailed on Mar. 10, 2024, 11 pages.
Jinek et al., "A Programmable Dual-RNA-Guided DNA Endonuclease in Adaptive Bacterial Immunity," Science, Jun. 2012, 337(6096):816-821.
Lee et al., "Binding Energetics of Ferredoxin-NADP+ Reductase with Ferredoxin and Its Relation to Function," ChemBioChem, Sep. 2011, 13(12):2062-2070.
Lindberg et al., "Engineering a platform for photosynthetic isoprene production in cyanobacteria, using Synechocystis as the model organism," Metabolic Engineering, Jan. 2010, 12(1):70-79.
Miroux et al., "Over-production of Proteins in Escherichia coli: Mutant Hosts that Allow Synthesis of some Membrane Proteins and Globular Proteins at High Levels," Journal of Molecular Biology, Jun. 1996, 260(3):289-298.
Ran et al., "In vivo genome editing using *Staphylococcus aureus* Cas9," Nature, Apr. 2015, 20(7546):186-191.
Romanos et al., "Foreign Gene Expression in Yeast: a Review," Yeast, Jun. 1992, 8(6):423-488.
Shi et al., "Both human ferredoxins 1 and 2 and ferredoxin reductase are important for iron-sulfur cluster biogenesis," Biochimica et Biophysica Acta (BBA)—Molecular Cell Research, Feb. 2012, 1823(2):484-492.
Shilling et al., "Improved designs for pET expression plasmids increase protein production yield in *Escherichia coli*," Communications Biology, May 2020, 3(1):214, 8 pages.
UniProt Accession No. B6V6V6, "3-ketosteroid-9-alpha-monooxygenase, ferredoxin reductase component," dated May 25, 2022, 3 pages.
UniProt Accession No. H9IWP6, "Rieske domain-containing protein," dated Apr. 7, 2021, 1 page.
UniProt Accession No. I7ML19, "Cholesterol 7-desaturase," dated May 25, 2022, 2 pages.
UniProt Accession No. O54037, "Vanillate O-demethylase oxidoreductase," dated May 25, 2022, 2 pages.

(Continued)

*Primary Examiner* — Suzanne M Noakes
(74) *Attorney, Agent, or Firm* — Fish & Richardson P.C.

(57) ABSTRACT

The present disclosure relates to fusion proteins including an iron-sulfur protein (e.g., cholesterol 7-desaturase (C7D)) and a ferredoxin reductase (e.g., KshB) that can efficiently convert cholesterol to 7-dehydrocholesterol (7-DHC) in vivo. Also disclosed herein are engineered microbes (e.g., *E. coli*) expressing the fusion proteins and methods of use thereof.

20 Claims, 17 Drawing Sheets

Specification includes a Sequence Listing.

(56) References Cited

OTHER PUBLICATIONS

UniProt Accession No. P9WJ93, "3-ketosteroid-9-alpha-monooxygenase, ferredoxin reductase component," dated May 25, 2022, 4 pages.

UniProt Accession No. Q17938, "Cholesterol 7-desaturase," dated May 25, 2022, 3 pages.

UniProt Accession No. Q1JUZ1, "Cholesterol 7-desaturase nvd," dated May 25, 2022, 4 pages.

UniProt Accession No. Q8KQH9, "Oxygenase reductase KshB," dated Jan. 19, 2022, 2 pages.

Zhang et al., "Introduction of an NADH regeneration system into Klebsiella oxytoca leads to an enhanced oxidative and reductive metabolism of glycerol," Metabolic Engineering, Mar. 2009, 11(2):101-106.

Zhang, "Advances of ferredoxins from strictly anaerobic bacteria," Acta Microbiologica Sinica, Apr. 2021, 62(1):24-32 (with English abstract).

Zhu et al., "Development of Engineered Ferredoxin Reductase Systems for the Efficient Hydroxylation of Steroidal Substrates," ACS Sustainable Chemistry & Engineering, Oct. 2020, 8(44):16720-16730.

Zhu et al., "Soluble expression, purification and biochemical characterization of a C-7 cholesterol dehydrogenase from *Drosophila melanogaster*," Steroids, Dec. 2019, 152:108495, 7 pages.

FIG. 2

| Strain No. | Modification | C7D Gene ID | KshB Gene ID | C7D AA Sequence | KshB AA Sequence | Fusion protein AA sequence |
|---|---|---|---|---|---|---|
| 28 | Separated C7D and KshB Variant 1 | GENE051 | GENE065 | SEQ ID NO: 1 | SEQ ID NO: 7 | N/A |
| 29 | Separated C7D and KshB Variant 2 | GENE324 | GENE065 | SEQ ID NO: 2 | SEQ ID NO: 7 | N/A |
| 30 | No KshB (control) | GENE051 | N/A | SEQ ID NO: 1 | N/A | N/A |
| 31 | No KshB (control) | GENE324 | N/A | SEQ ID NO: 2 | N/A | N/A |
| 32 | Separated C7D and KshB Variant 3 | GENE1969 | GENE065 | SEQ ID NO: 3 | SEQ ID NO: 7 | N/A |
| 33 | Separated C7D and KshB Variant 4 | GENE1095 | GENE065 | SEQ ID NO: 4 | SEQ ID NO: 7 | N/A |
| 34 | Separated C7D and KshB Variant 5 | GENE1968 | GENE065 | SEQ ID NO: 5 | SEQ ID NO: 7 | N/A |
| 35 | Separated C7D and KshB Variant 6 | GENE1967 | GENE065 | SEQ ID NO: 6 | SEQ ID NO: 7 | N/A |
| 36 | Separated KshB and C7D Variant 7 | GENE1966 | GENE051 | SEQ ID NO: 8 | SEQ ID NO: 1 | N/A |
| 37 | Separated KshB and C7D Variant 8 | GENE065 | GENE324 | SEQ ID NO: 7 | SEQ ID NO: 2 | N/A |
| 38 | Fusion Variant 1 (flexible linker) | GENE429 (SEQ ID NO: 19) | | SEQ ID NO: 4 | SEQ ID NO: 7 | SEQ ID NO: 15 |
| 39 | Fusion Variant 2 (rigid linker) | GENE1965 (SEQ ID NO: 20) | | SEQ ID NO: 4 | SEQ ID NO: 7 | SEQ ID NO: 16 |
| 40 | Fusion Variant 3 (flexible linker) | GENE1964 (SEQ ID NO: 34) | | SEQ ID NO: 6 | SEQ ID NO: 7 | SEQ ID NO: 17 |
| 41 | Fusion Variant 4 (rigid linker) | GENE1963 (SEQ ID NO: 21) | | SEQ ID NO: 6 | SEQ ID NO: 7 | SEQ ID NO: 18 |

FIG. 7

Wild-type C. elegans C7D (SEQ ID NO: 1)

MLLEQIWGFLTAHPISVVTTILIVYLIHITLKPLNRVRRLGDVGLFFGKPELKGFYRERQLERLKLLRRVGDMPPVFPNGWYCVCESEK
LANNQIMEITVLGQFLSLIRSESGAVYITDSYCPHIGANFNIGGRVVRDNCIQCPFHGWIFSAETGKCVEVPYDEGRIPEQAKVTTWPC
IERNNNIYLWYHCDGAEPEWEIPEITEITDGFWHLGGRTEHEVMCHIQEIPENGADIAHLNYLHKSAPPVTKGSDIIKTDLSDPQPAVQ
HVWDGKWEVKSEEDRHCGVMHLNQFMTFWGYKVPLTSSKLVAEQHGPGIVHMLFDFGIWGKGVVFQTVTPEEALLQRVRFRIFSNIPWF
FVKFFMTVEAMQFERDVFIWSNKKYIKSPLLVKNDGPIQKHRRWFSQFYTENSPKMLKDGSLSNQAKSIFDW*

Wild-type C. elegans C7D with C-terminal HIS-tag (SEQ ID NO: 2)

MLLEQIWGFLTAHPISVVTTILIVYLIHITLKPLNRVRRLGDVGLFFGKPELKGFYRERQLERLKLLRRVGDMPPVFPNGWYCVCESEK
LANNQIMEITVLGQFLSLIRSESGAVYITDSYCPHIGANFNIGGRVVRDNCIQCPFHGWIFSAETGKCVEVPYDEGRIPEQAKVTTWPC
IERNNNIYLWYHCDGAEPEWEIPEITEITDGFWHLGGRTEHEVMCHIQEIPENGADIAHLNYLHKSAPPVTKGSDIIKTDLSDPQPAVQ
HVWDGKWEVKSEEDRHCGVMHLNQFMTFWGYKVPLTSSKLVAEQHGPGIVHMLFDFGIWGKGVVFQTVTPEEALLQRVRFRIFSNIPWF
FVKFFMTVEAMQFERDVFIWSNKKYIKSPLLVKNDGPIQKHRRWFSQFYTENSPKMLKDGSLSNQAKSIFDWAAALEHHHHHH*

Modified C. elegans C7D-1 (SEQ ID NO: 3)

MGSLLEQIWGFLTAHPISVVTTILIVYLIHITLKPLNRVRRLGDVGLFFGKPELKGFYRERQLERLKLLRRVGDMPPVFPNGWYCVCES
EKLANNQIMEITVLGQFLSLIRSESGAVITDSYCPHIGANFNIGGRVVRDNCIQCPFHGWIFSAETGKCVEVPYDEGRIPEQAKVTTW
PCIERNNNIYLWYHCDGAEPEWEIPEITEITDGFWHLGGRTEHEVMCHIQEIPENGADIAHLNYLHKSAPPVTKGSDIIKTDLSDPQPA
VQHVWDGKWEVKSEEDRHCGVMHLNQFMTFWGYKVPLTSSKLVAEQHGPGIVHMLFDFGIWGKGVVFQTVTPEEALLQRVRFRIFSNIP
WFFVKFFMTVEAMQFERDVFIWSNKKYIKSPLLVKNDGPIQKHRRWFSQFYTENSPKMLKDGSLSNQAKSIFDW*

Modified C. elegans C7D-2 (SEQ ID NO: 4)

MQLLEQIWGFLTAHPISVVTTILIVYLIHITLKPLNRVRRLGDVGLFFGKPELKGFYRERQLERLKLLRRVGDMPPVFPNGWYCVCES
EKLANNQIMEITVLGQFLSLIRSESGAVITDSYCPHIGANFNIGGRVVRDNCIQCPFHGWIFSAETGKCVEVPYDEGRIPEQAKVTTW
PCIERNNNIYLWYHCDGAEPEWEIPEITEITDGFWHLGGRTEHEVMCHIQEIPENGADIAHLNYLHKSAPPVTKGSDIIKTDLSDPQPA
VQHVWDGKWEVKSEEDRHCGVMHLNQFMTFWGYKVPLTSSKLVAEQHGPGIVHMLFDFGIWGKGVVFQTVTPEEALLQRVRFRIFSNIP
WFFVKFFMTVEAMQFERDVFIWSNKKYIKSPLLVKNDGPIQKHRRWFSQFYTENSPKMLKDGSLSNQAKSIFDW*

Modified C. elegans C7D-1 with C-terminal HIS-tag (SEQ ID NO: 5)

MGSLLEQIWGFLTAHPISVVTTILIVYLIHITLKPLNRVRRLGDVGLFFGKPELKGFYRERQLERLKLLRRVGDMPPVFPNGWYCVCES
EKLANNQIMEITVLGQFLSLIRSESGAVITDSYCPHIGANFNIGGRVVRDNCIQCPFHGWIFSAETGKCVEVPYDEGRIPEQAKVTTW
PCIERNNNIYLWYHCDGAEPEWEIPEITEITDGFWHLGGRTEHEVMCHIQEIPENGADIAHLNYLHKSAPPVTKGSDIIKTDLSDPQPA

FIG. 7 (continued)

VQHVWDGKWEVKSEEDRHCGVMHLNQFMTFWGYKVPLTSSKLVAEQHGPGIVHMLFDFGIWGKGVVFQTVTPEEALLQRVRFRIFSNIP
WFFVKFFMTVEAMQFERDVFIWSNKKYIKSPLLVKNDGPIQKHRRWFSQFYTENSPKMLKDGSLSNQAKSIFDWAAALEHHHHHH*

**Modified *C. elegans* C7D-2 with C-terminal HIS-tag (SEQ ID NO: 6)**

MQLLEQIWGFLTAHPISVVTTILIVYLIHITLKPLNRVRRLGDVGLFFGKPELKGFYREROLERLKLLRRVGDMPPVFPNGWYCVCES
EKLANNQIMEITVLGQFLSLIRSESGAVYITDSYCPHIGANFNIGGRVVRDNCIQCPFHGWIFSAETGKCVEVPYDEGRIPEQAKVTTW
PCIERNNNIYLWYHCDGAEPEWEIPEITEITDGFWHLGGRTEHEVMCHIQEIPENGADIAHLNYLHKSAPPVTKGSDIIKTDLSDPQPA
VQHVWDGKWEVKSEEDRHCGVMHLNQFMTFWGYKVPLTSSKLVAEQHGPGIVHMLFDFGIWGKGVVFQTVTPEEALLQRVRFRIFSNIP
WFFVKFFMTVEAMQFERDVFIWSNKKYIKSPLLVKNDGPIQKHRRWFSQFYTENSPKMLKDGSLSNQAKSIFDWAAALEHHHHHH*

**Wild-type *Mycobacterium tuberculosis* KshB (SEQ ID NO: 7)**

MTEAIGDEPLGDHVLELGIAEVVDETDEARSLVFAVPDGSDDPEIPPRRLRYAPGQFLTLRVPSERTGSVARCYSLCSSPYTDDALAVT
VKRTADGYASNWLCDHAQVGMRIHVLAPSGNFVPTTLDADFLLLAAGSGITPIMSICKSALAEGGQVTLLYANRDDRSVIFGDALREL
AAKYPDRLTVLHWLESLQGLPSASALAKLVAPYTDRPVFICGPGPFMQAARDALAALKVPAQQVHIEVFKSLESDPFAAVKVDDSGDEA
PATAVVELDGQTHTVSWPRTAKLLDVLLAAGLDAPFSCREGHCGACACTLRAGKVNMGVNDVLEQQDLDEGLILACQSRPESDSVEVTY
DE*

**Modified *Mycobacterium tuberculosis* KshB (SEQ ID NO: 8)**

MQLTEAIGDEPLGDHVLELGIAEVVDETDEARSLVFAVPDGSDDPEIPPRRLRYAPGQFLTLRVPSERTGSVARCYSLCSSPYTDDALA
VTVKRTADGYASNWLCDHAQVGMRIHVLAPSGNFVPTTLDADFLLLAAGSGITPIMSICKSALAEGGQVTLLYANRDDRSVIFGDALR
ELAAKYPDRLTVLHWLESLQGLPSASALAKLVAPYTDRPVFICGPGPFMQAARDALAALKVPAQQVHIEVFKSLESDPFAAVKVDDSGD
EAPATAVVELDGQTHTVSWPRTAKLLDVLLAAGLDAPFSCREGHCGACACTLRAGKVNMGVNDVLEQQDLDEGLILACQSRPESDSVEV
TYDE*

Fusion Variant 1 in strain No. 38 (SEQ ID NO: 15)

MQLLEQIWGFLTAHPISVVTTILIVYLIHITLKPLNRVRRLGDVGLFFGKPELKGFYREROLERLKLLRRVGDMPPVFPNGWYCVCES
EKLANNQIMEITVLGQFLSLIRSESGAVYITDSYCPHIGANFNIGGRVVRDNCIQCPFHGWIFSAETGKCVEVPYDEGRIPEQAKVTTW
PCIERNNNIYLWYHCDGAEPEWEIPEITEITDGFWHLGGRTEHEVMCHIQEIPENGADIAHLNYLHKSAPPVTKGSDIIKTDLSDPQPA
VQHVWDGKWEVKSEEDRHCGVMHLNQFMTFWGYKVPLTSSKLVAEQHGPGIVHMLFDFGIWGKGVVFQTVTPEEALLQRVRFRIFSNIP
WFFVKFFMTVEAMQFERDVFIWSNKKYIKSPLLVKNDGPIQKHRRWFSQFYTENSPKMLKDGSLSNQAKSIFDWGGGSGGGGSGGGGS
MTEAIGDEPLGDHVLELGIAEVVDETDEARSLVFAVPDGSDDPEIPPRRLRYAPGQFLTLRVPSERTGSVARCYSLCSSPYTDDALAVT
VKRTADGYASNWLCDHAQVGMRIHVLAPSGNFVPTTLDADFLLLAAGSGITPIMSICKSALAEGGQVTLLYANRDDRSVIFGDALREL
AAKYPDRLTVLHWLESLQGLPSASALAKLVAPYTDRPVFICGPGPFMQAARDALAALKVPAQQVHIEVFKSLESDPFAAVKVDDSGDEA

FIG. 7 (continued)

PATAVVELDGQTHTVSWPRTAKLLDVLLAAGLDAPFSCREGHCGACACTLRAGKVNMGVNDVLEQQDLDEGLILACQSRPESDSVEVTYDE*

Fusion Variant 2 in strain No. 39 (SEQ ID NO: 16)

MQLLEQIWGFLTAHPISVVTTLILIVYLIHITLKPLNRVRRLGDVGLFFGKPELKGFYRERQLERLKLLRRVGDMPPVFPNGWYCVCES
EKLANNQIMEITVLGQFLSLIRSESGAVYITDSYCPHIGANFNIGGRVVRDNCIQCPFHGWIFSAETGKCVEVPYDEGRIPEQAKVTTW
PCIERNNNIYLWYHCDGAEPEWEIPEITEITDGFWHLGGRTEHEVMCHIQEIPENGADIAHLNYLHKSAPPVTKGSDIIKTDLSDPQPA
VQHVWDGKWEVKSEEDRHCGVMHLNQFMTFWGYKVPLTSSKLVAEQHGPGIVHMLFDEGIWGKGVVFQTVTPEEALLQRVRFIFSNIP
WFFVKFFMTVEAMQFERDVFIWSNKKYIKSPLLVKNDGPIQKHRRWFSQFYTENSPKMLKDGSLSNQAKSIFDWAEAAAKEAAAKAMTE
AIGDEPLGDHVLELQIAEVVDETDEARSLVFAVPDGSDDPEIPPRRLRYAPGQFLTLRVPSERTGSVARCYSLCSSPYTDDALAVTVKR
TADGYASNWLCDHAQVGMRIHVLAPSGNFVPTTLDADFLLLAAGSGITPIMSICKSALAEGGGQVTLLYANRDDRSVIFGDALRELAAK
YPDRLTVLHWLESLQGLPSASALAKLVPAQQVHIEVFKSLESDPFAAVKVDDSGDEAPAT
AVVELDGQTHTVSWPRTAKLLDVLLAAGLDAPFSCREGHCGACACTLRAGKVNMGVNDVLEQQDLDEGLILACQSRPESDSVEVTYDE*

Fusion Variant 3 in strain No. 40 (SEQ ID NO: 17)

MQLLEQIWGFLTAHPISVVTTLILIVYLIHITLKPLNRVRRLGDVGLFFGKPELKGFYRERQLERLKLLRRVGDMPPVFPNGWYCVCES
EKLANNQIMEITVLGQFLSLIRSESGAVYITDSYCPHIGANFNIGGRVVRDNCIQCPFHGWIFSAETGKCVEVPYDEGRIPEQAKVTTW
PCIERNNNIYLWYHCDGAEPEWEIPEITEITDGFWHLGGRTEHEVMCHIQEIPENGADIAHLNYLHKSAPPVTKGSDIIKTDLSDPQPA
VQHVWDGKWEVKSEEDRHCGVMHLNQFMTFWGYKVPLTSSKLVAEQHGPGIVHMLFDEGIWGKGVVFQTVTPEEALLQRVRFIFSNIP
WFFVKFFMTVEAMQFERDVFIWSNKKYIKSPLLVKNDGPIQKHRRWFSQFYTENSPKMLKDGSLSNQAKSIFDWAAALEHHHHHHGGGG
SGGGGSGGGGSHHHHHHSSGLVPRGSHMTEAIGDEPLGDHVLELQIAEVVDETDEARSLVFAVPDGSDDPEIPPRRLRYAPGQFLTLRV
PSERTGSVARCYSLCSSPYTDDALAVTVKRTADGYASNWLCDHAQVGMRIHVLAPSGNFVPTTLDADFLLLAAGSGITPIMSICKSALA
EGGGQVTLLYANRDDRSVIFGDALRELAAKYPDRLTVLHWLESLQGLPSASALAKLVPAQQVHIEVFKSLESDPFAAVKVDDSGDEAPATAVVELDGQTHTVSWPRTAKLLDVLLAAGLDAPFSCREGHCGACACTLRAGKVNMGVNDV
LEQQDLDEGLILACQSRPESDSVEVTYDE*

Fusion Variant 4 in strain No. 41 (SEQ ID NO: 18)

MQLLEQIWGFLTAHPISVVTTLILIVYLIHITLKPLNRVRRLGDVGLFFGKPELKGFYRERQLERLKLLRRVGDMPPVFPNGWYCVCES
EKLANNQIMEITVLGQFLSLIRSESGAVYITDSYCPHIGANFNIGGRVVRDNCIQCPFHGWIFSAETGKCVEVPYDEGRIPEQAKVTTW
PCIERNNNIYLWYHCDGAEPEWEIPEITEITDGFWHLGGRTEHEVMCHIQEIPENGADIAHLNYLHKSAPPVTKGSDIIKTDLSDPQPA
VQHVWDGKWEVKSEEDRHCGVMHLNQFMTFWGYKVPLTSSKLVAEQHGPGIVHMLFDEGIWGKGVVFQTVTPEEALLQRVRFIFSNIP
WFFVKFFMTVEAMQFERDVFIWSNKKYIKSPLLVKNDGPIQKHRRWFSQFYTENSPKMLKDGSLSNQAKSIFDWAAALEHHHHHHAEAA
AKEAAAKAHHHHHHSSGLVPRGSHMTEAIGDEPLGDHVLELQIAEVVDETDEARSLVFAVPDGSDDPEIPPRRLRYAPGQFLTLRVPSE
RTGSVARCYSLCSSPYTDDALAVTVKRTADGYASNWLCDHAQVGMRIHVLAPSGNFVPTTLDADFLLLAAGSGITPIMSICKSALAEGG

FIG. 7 (continued)

GQVTLLYANRDDRSVIFGDALRELAAKYPDRLTVLHWLESLQGLPSASALAKLVAPYTDRPVFICGPGPFMQAARDALAALKVPAQQVH
IEVFKSLESDPFAAVKVDDSGDEAPATAVVELDGQTHTVSWPRTAKLLDVLLAAGLDAPFSCREGHCGACACTLRAGKVNMGVNDVLEQ
QDLDEGLILACQSRPESDSVEVTYDE*

FIG. 8

GENE429 (SEQ ID NO: 19)

ATGCAGCTTTTGTTGGAGCAAATCTGGGTTTCCTGACTGCACATCCAATCAGTGTAGTCACGACGATTTTAATCGTATATTTAATCCA
CATTACGCTGAAGCCGCTGAATCGTGTGCGTCGTTGCGTGGGACGTGGGCTTATTCTTCGGCAAGCCCGAATTGAAGGGTTTCTACCGTG
AGCGTCAGCTGAACGCCTGAAACTTTGCCGTGTGGGAGAATACAGTTTAGGTCAATTCGTAACGGTTGGTATTCGTGTTGCGAATCG
GAGAAACTGGCTAACAATCAGATCATGAATTGGTGCGAAATGCGTAGCCTTATTCGTAACTGTATCGCAGTGTCCCTTCCATG
TACAGATTCTTACTGTCCGCACATTGGTGCGAAATGCGTAGAAGACGCATCCCTGAACAGGGCAAAGGTCACCACCTGG
GGTGGATTTTCTCTGCGAGAACAACAACATCTATTTGTGATGGGCGGAGCCTTCAAGAGTAATGTGCCATATTCAAGAGATGGGAAATCCCTGAGAACGGAGCTGACATTG
CCGTGCATCGAACGGCTTTGGCATCTGGGGACGTACAGAACATGAGGTAATGTGCCATATTGACGTAATCAGAGATTGTCTGACCCCGAGCCTGCT
CGCACTTAAATTATTTACACAAGTCGGGACGGTAAATGGACGTTAAGAGTGAAGAAGACCCGTTATGTGGTATCTGAACCAGTTCATGACATT
GTCCCGCATGTATAAGGTCCCCTTGACCAGCTCTAAGTTGGTGCAGAACAGCATGGCCCAGGCATCGTGCAGCGTGTCAATTGTTTGATTTCGGTA
TTTGGGGTTATAAGGTCCCCTTGACCAGCTCTAAGTTGGTGCAGAACAGCATGGCCCAGGCATCGTGCAGCGTGTCAATTGTTTGATTTCGGTA
TTTGGGGAAAAGGGGTGGTGTTCCAAACGTTACACCCGAGGAAGCATTGTTGAACGGTCGATGTGTCATCTGGAGTAACAAGAAATATATTAAGTC
TGTTCTTCGTCAAGTTCTTTATGACCGTCAAGAACGATGGCCCCATCCAGAAACATCGTCGCTGGTTTAGCCAATTCTATACCGAGAACTCACCGAAATGCTGA
ACCCCTGTTGCATCTCTTTCTAACCAGGCGAAGCCACTGCGAACCACTGGAAGTCCATCGGAGATCATGTCTCAGAATTGGCCAGCAGCGCCCAGTTCTTTACT
AGGATGGGATCTCTTTCTAACCAGGCGAAGCCACTGCGAACCACTGGAAGTCCATCGGAGATCATGTCTCAGAATTGGCCAGCAGCGCCCAGTTCTTTACT
ATGACTGAGGCGATAGGCCAGTGCTGAGCGAGCGCACCGGCAGTGTTGCTCCAGTAATTGGTTATGTGCTTCTGGCCGCCTGAGATCGGGGATCACTCCATTATGAGTATTGCAAAGGTC
GAGTTTAGTATTGCCAGTCCCTAGCGTCCCTGTTATGTCCAGTAATTGGTTATGTGCTTCTGGCCGCCTGAGATCGGGGATCACTCCATTATGAGTATTGCAAAAGTG
TGCGGGGTGCCCAGGTACTGCTCAACGACATTGGATGCTGACTTTTGCTTCTGACGCTAATCGGTACGCAGATCAGTGATTTTGCCGACGCCTTACGCCAGTTG
GCGGCGAAGTACCCGGACCCGTCAGTTTCATCCGTGGTTAACAGTATTACAGTGTGTGGTGCCCTTGAATCTCTTCAAGGTTGCAAGCCCGGTCGGCCCGCCCAGTCAAATTGGT
TGCTCCATATACGCAGGTTCATATAGAGAGTATTCAAGTCTCAGATGGTCAGAGGTGGTGGAGTTGGATGGTCCGTGAGGTCGACGTTCAGCTTCCTGCTGCTAAGTCGCCTAGAAGCA
CCAGGCCACTGCTCCGTTCCTGTTGTGGAGTTGGATGGTCAGAGGGGCAGGTTGCAACCCGTTGGCCCTAGAACGGCAGCTCATAGGTTTCGCGGCCATTGGCTACGCACTTTGTCGTGCACTTTGTGCGCAAATTATTGATGTCCTTCTTGCGGC
GGGACTTGCTGAGCGCCTCCGTTCCTGTTGTGGAGTTGGATGGTCAGAGGGGCAGGTTGCAACCCGTTGGCCCTAGAACGGCAGCTCATAGGTTTCGCGGCCATTGGCTACGCACTTTGTCGTGCACTTTGTGCGCAAATTATTGATGTCCTTCTTGCGGC
ATGACGTGCTGAGCAGCAGGACCCTTGACGCAGGAGCCTCCGTTGTGCACTTTGTCGCGCAAATTATTGGATGCAGCCCCGCAGGAATCCCCTGCCGCGAGCCCCGAATTGCACCCGCCAGCCAGGACCCTTGACGCAGGAGCCTCCGTTGTGCATGCAGTCAGTCCCGCTCCCGTCCCGAATCGGACTCGGCCGTTGAGGTGACCTAT
GACGAGTAA

GENE1965 (SEQ ID NO: 20)

FIG. 8 (continued)

ATGCAGCTTTTGTTGGAGCAAATCTGGGGTTTCCTGACTGCACATCCAATCAGTGTAGTCACGACGATTTTAATCGTATATTTAATCCA
CATTACGCTGAAGCCGCTGAATCGTGTGCGTCGTTGCGCCGTGGGGGACGTCGGCAAGCCCGAATTGAAGGGTTTCTACCGTG
AGCCGTCAGCTGGAACGCCTGAAATCAGATCATGGATGCCAGTTCTCCAACGGTTGGTATTGTGTTTGCGAATCG
GAGAAACTGGCTACAATGTCCGCACATTGGTGCCGAAATTACACAGTTTTAGTCAGTCCTTATTCGTAGCGAACTGTATCTCGTCGTTTACAT
TACAGATTCTTACTGTCTCTCCGAGAACAACAACATCTATTTATGGTATCACACATGAGAAGGACGCCCTATGATGAAGGACGCATCCCTGAACAGGCAAAGGTCACCACCTGG
GGTGGATTTCTTCCTGGTGCCGGAAATGCCTAGAAGTGCCTATCACTGGTTATGGTATCACACATGAGAAGGACGCCCTATGATGAAGGACGCATCCCTGAACAGGCAAAGGTCACCACCTGG
CCGTGCATCGCAACGCAACAACAACATCTATTTATGGTATCACACATGAGAAGGACGCCCTATGATGAAGGACGCATCCCTGAACAGGCAAAGGTCACCACCTGG
CACTGACGCGTTTTGGCATCTGGGGGACGTACAGAAGTACAGAACATGAGTAATGCCGATATGCATTGTGGTTGTCTGAACCCAGTTCATGACATT
CGCACTTAAATTATTTACACAAGTCTGCCCCCCGGGAGAAGTTAAGAGTCCAGCAGCAGACCGCATGGCCCAGGCGTGTACGTTTCCGCATCTTTTCGAATATCCCT
GTCCCAGCATGTATAAGGTCCCCTTGACAAGTGGTGGCAGAACAGCAGCATTGTTGCAGCGTGTTTCATCTGGAGTAACAAGCAATTTGAACGCGATGTGTTCATCGTGTTCATCTGGAGTAACAAGAACTCACCGAAAATGCTGA
TTGGGGTTATAAGGTCCCCTTGACAAGTGGTGGCAGAACAGCAGCATTGTTGCAGCGTGTTTCATCTGGAGTAACAAGAACTCACCGAAAATGCTGA
TTTGGGAAAAGGGGTGGTGTTCAAGTTCTTTATGACGATGGCCCTCGAAGCAATTTGAACGCGATGTGTTCATCTGGAGTAACAAGAACTCACCGAAAATGCTGA
TGGTTCTTCGTCGTTGGTCAAGTTCTTTATGACGATGGCCCTCGAAGCAATTTGAACGCGATGTGTTCATCTGGAGTAACAAGAACTCACCGAAAATGCTGA
ACCCCTGTTGTCAAGAACGATGGCCCATCGGGAGCGAAGTCCATCTCGATTGGGCTGAGCGTGCACAGCCCTGTGCTCCAAGTCGGGGATCGGACAGAAGTTTGCGGAATTTCGT
AGGATGGATCTCTTTCTAACCACTGGGAGATCATGTCTCGTCGTTGTGCTGTGGAGGCCCAGCCAGCCAAGTCGGGGATCGGACAGAAGTTTGATCATGCCCAAGTCGGGGATCGGACAGAAGTTTGCGGAATTTCGT
GCGATAGGCGATGAACCACTGGGAGATCATGTCTCGTCGTTGTGCTGTGGAGGCCCAGCCAAGTCGGGGATCGGACAGAAGTTTGATCATGCCCAAGTCGGGGATCGGACAGAAGTTTGCGGAATTTCGT
ATTTGCAGTCCTGACGGGTCGGACGACCCTGAAATACCGCCAGCCCTGTTGCTACAGGCCATTCAAGTCGGGGATCGGACAGAAGTTTGATCATGCCCAAGTCGGGGATCGGACAGAAGTTTGCGGAATTTCGT
CTAGCGAGCGCACCGCAGTGGTTGCTCGTGTTGCTGCTGCTATGTGACTTTTTGCTTCGTACGCTAATTGGTATACGCGCTTAGCACGCCTTAGCACGCCTTAGCGCCTTGGCGG
TCCAACGACATTGGATGCTGACTTTTTGCTTCGTACGCTAATTGGTATACGCGCTTAGCACGCCTTAGCACGCCTTAGCGCCTTGGCGG
AAGGCGGCGGGCAAGCTGCTTAACAGTAACATTGTATTACACTGTGGTCTCATCTGTGTTCCCCTTTATGCAAGCCGCCTGTTAAGGTTGCCATTGGCGCACAGCCACT
AGTTCATATAGAGGTATTCAAGTCAGATGTCAGATGGTCAGACTTCAAGTCATACGGTTGGAGCTTGTCTTCAAGATGCGAAATTATTGATGTCCTTCTTGCGCGGGACTTGA
CGCTCCGGTCCGTGGCATTGTGTGCCGTTGCCTAGAACGGCAAGTCCACTTTGCGCAGCAATCGGAGGGTCAATATGCGGGGTCAATGACGTGC
TGGAGCAGGACCTTGACGAGGATTAATTTTGCATGTCAGTCCCGAATCGGACTCCCGTTGAGTGACCTATGACGAGTAA

GENE1964 (SEQ ID NO: 34)

ATGCAGCTTTTGTTGGAGCAAATCTGGGGTTTCCTGACTGCACATCCAATCAGTGTAGTCACGACGATTTTAATCGTATATTTAATCCA
CATTACGCTGAAGCCGCTGAATCGTGTGCGTCGTTGCGCCGTGGGGGACGTCGGCAAGCCCGAATTGAAGGGTTTCTACCGTG

FIG. 8 (continued)

```
AGCGTCAGCTGGAACGCCTGAAACTTTTGCGCCGTGTGGGAGATATGCCACCTGTATTTCCAACGGTTGGTATTGTGTTTGCGAATCG
GAGAAACTGGCTAACAATCAGATCATGGAAATTCAGATCATGGAGAATTACAGTTTTAGCTGAACTTCAGTTCGGCGAATCTGTGCGGTTTACAT
TACAGATTCTTACTGTCCGCACATTGGTGTGCGAACTTGCGAAATGCGTAGAACTCGGCTGATAACTGTATCCAGTGTCCCTTCCATG
GGTGGATTTTCTGCGAACGCAACAACATCTATTTATGGTATCACTGTGTAGAACAGGACGCATCCGAAAGTCACCACTGG
CCGTGCATCGAACGCGCTTTTGGCATCTGGGGGACGTACAGAACATGAGGTAATGTGCCATATTCAAGAGATCAAGAACGGAGTCACAGAAAT
CACTGACGGCTTTTGGCATCTGGGGGACGTACAGAACATGAGGTAATGTGCCATATTCAAGAGATCAAGAACAGATTTGTCTGACCCGCAGCCTGCT
CGCACTTAAATTATTTACACAAGTCTGCCCCCCCCGTAAGTTGGTGGCTAAATGGACGGTAAGTGAAGAAGACCGCCATTGTGTGGCAGAACAGAGCT
GTCCAGCATGTATAAGGTCCCCTTGACCGGTAAATGGACGGTAAGTGAAGAAGACCGCCATTGTGTTGGCAGAACAGAGCATTGTTGTTGCAGCCGTCGTGAGCATCGTGTAACGGTGAAGCGCAATTGTTGACGCTAACCGGTTACACCCGGAATGCGAACATGGTTCGTGTACGTTTCATCTGGAGTAACAAGAAATATATTAAGTC
TGGTTCTTCGTCAAGTTCTTTATGACCGTCGAAGCAATTTGACCGTGTTTCATCTGGAGTAACAAGAAATATATTAAGTC
ACCCCTGTTGGTCAAGAACGATGGCCCCATCCGAAGAAACATCGTCGTGTTTAGCCACTCGAGAACTCACCGAAATGCTGA
AGGATGGATCTCTTTCTAACCAGGCGAAGTCCATCTTCGATTGGGCGCCACTCGAGAACTCACCGAAATGCTGA
TCAGGAGGTGGTGGATCTGGCGAGGTGGTAGTcatcatcatcacagcagcgccgcctggtgccgcggcagccatATGACTGA
GCGATAGCGATGAACCACTGGGAGATCATGTCTTGGAACTTCAGATAGCGGAAGTTGTAGATGAGACTGACGAGGCGCGAGTTTAG
TATTTGCAGTCCCTGGAGCGGTCGGACGCAGTGTTGCTCAGTCAGTAGCGGAAGTTGTAGATGAGACTGACGAGGCGAGTTTAG
CCTAGCGAGCCACCGGCAGCCAGTGTTGCTCAGTAATTGGCTGTTATGTGATCATCCATCCGATGCGCATTGACGTTCAGTCCCATATACCGATGCGCATTCAGCGCGTCTTTAACGCTGCGGGTC
TTCCAACGACATTGGATGGGCAAGTAACATTGCTGTACGCTAATCGGATGACAGATCAGTGATTTTTGGCGACGCCTTAGCGCCCTTAACGCCAGTTGGCGGCGAA
GAAGGCGGCGGGACCCGGCTTAACCGCTTAACAGTATTACACTGCAGTTTTGGCGACGCCTTAGCGCCAAATTGTTGCTCCAT
GTACCCGGACCGGCTTAACCGCTTAACAGTATTACACTGCTTGAATCTCTTCAAGGTTTGCCGTCGGCCTTTGCGGATGCGCCTCAGCTTGGCGCAGCAG
ATACGGATGACCGGCTTAACCGCTTAACAGTATTACACTGCTTGAATCTCTTCAAGGTTTGCCGTCGGCCTTTGCGGATGCGCCTCAGCTTGGCGCAGCAG
ATACGGATGACCGGTTAACCGCTTAACAGTCCCTTGAATCAGACCCGTCGTTGCGCGGCTGTTAAGGTGCGAACAAGTGCCGGCACCGCCAC
CAGGTTCATATAGAGAGTATTCAAGTCAGTCCCTTGAATCAGACCCGTCGTTGCGCGGCTGTTAAGGTGCGAACAGGGCGAAATTATTGATGTCCTTCCTTGCCGGGACTTG
ACGCCCGTTCTGTGATGGTCAGATGGTCAGAGGGGCATTGTGTGCGTGGAGCTTGTGCTGCACTTTGCGCACTTTGCGGGCTAAGAAGGTGCACCTCATATGCAGCACTTGTGTCAATATGGGGTCATGACCAGCAAGGTCAATATGGGGTCAATGACGTTG
CTGGAGCAGGAGACCCTTGAGCGGAGATATGGGGTCAATGACGTTGTCCCGTTATTCTTCGGCAAGCCCGAATCGGACTCCGTTGAGGTGACCTATGACGAGTA
A
```

GENE1963 (SEQ ID NO: 21)

```
ATGGCAGCTTTTGTTGGAGCAAATCTGGGGTTTCCCTGACTGCACATCCAATCAGTGTAGTCACGACGATTTTAATTGTATATTTAATCCA
CATTACGCTGAAGCCGCTGAATCGTTGCGTCGTTGCGGTCGTTGCCGGCTTATTCTTCGGCAAGCCCGAATTGAAGGGTTTCTACCGTG
```

FIG. 8 (continued)

```
AGCGTCAGCTGGAACGCCTGAAACTTTTGCGCCGTGTGGGAGATATGCCACCTGTATTTCCCAACGGTTGGTATTGTGTTTGCGGAATCG
GAGAAACTGGCTAACAATCAGATCATGGAAATTACAGTTTAGGTCAGTTCAATATCCTTAAGCCTTATTGTGTAAGCGGAATCGTGTCGCGGTTTACAT
TACAGATTCTTACTGTCCGCACATTGGTGTGCAACTTCGGCGTGTGGTTCGCGATAACTGTATCCAGTGTCCCTTCCATG
GGTGGATTTCTGCGAACGCAACAACATCTATTTATGGTATCACTGTGAAGGACGCATCTGATGAAGGCGGAGCCTGAAGGACCTGAAGATCAAGACTGG
CCGTGCATCGACGGCTTTTGGCATCTGGGGGACGTACAGAGAACATGTGCCATATATTCAAGAGAGATCAAGAGACAGATTTGTCTGACCCGCCAGCCTGCT
CACTGACGGCTTTTAATTATTTACACAAGTCTGCCCCCCCCGGAGTAAGTGGAGGACAGTTAAGGTAGCGATATCAAGGTAGAGATCCTGAGGAGCTAAAGGAACGGAGCTGACATTG
CGCACTTAAATTATTTACACAAGTCTGCCCCCCCCGGAGTAAGTGGACGGTAAATGGAAGTTAAGTTCTAAAGTGAAGAAAGACCCGGAGTTCATGACATT
GTCCAGCATGTATAAGGTATGGAAGTCCCCTTGACCAGCTCCTTTGACCCTTGACCAGCTCTAAAGTTGGTGGCAGACAGACAGCATTGTTGCAGGCGTGTTGCAGCGTGTACTGTCCGATCCTTCGGTA
TTTGGGAAAAGGGTGGTGTTCTTTATGACGTCCAAGCGTCGATGGATGGTGTTCATCTCGAAGCAATTTGACGCGATGTGTTCATCTGAGATAACAAGAAATATATTAAGTC
TGGTTCTTCGTCAAGTTGTCAAGAACGATGGCCCCCATCCAGAAACATCCAGAAACATCGTCGTGGTTTAGCCACTCGAGAATCACCATCACGCTGAGGCTGA
ACCCCGTGTTGGTCAAGAACGATGGCCCCCATCCAGAAACATCGTCGTGGTTTAGCCACTCGAGAATCACCATCACGCTGAGGCTGCA
AGGATGGATCTCTTTCTAACAAGGCGCTAAGCGCATCATCATCATCATCATCATCACACAGCGCCCTGGTGTGGCGCCGCGGCAGCATCAGCCCGGAGTTTAGTATTTGCAG
GCCAAAGAAGCCACTGGGATCAGATCAATGTCTTGGTCGACAGATCACCTGCCGCCCTGCCCAGTTCTTAACGCTGCGCCAGCCCAGTTCTTAACGCTGGTGGTCCCTAGCGAG
TCCCTGACGGGTCGGACGACGCAGCAGTGTCCTGAAATACCGCCACGGCCGCCTCCTCCCAAGTCGGGGATCACTGATTTTTGCCGCGTCGCCCTTGC
GCACCGGCAGTGTTGCTCGTGCTGTGCTACAGCCTGGGATCATGCGCGTAATCGGGAATCAGTGTTTGCCGTCGCTGGCCTTGCGGGATATGCCGCTCCATTATCGACC
TGGGTATGCCAGTGCAGTGTCAGACTTTTGCTTCTGCGCCTAATCGGTCTCTGGAGCCGCCCTTTTGCAAAAGGCGTTGGCGCGCGAAGTACCCGGA
CATTGGACAAGTAACATTGCTAGTACGCTGTATTACACTGCTTGAAATCTCTGAATCTTCTTCAAGGTTTGCCGTCGCGGCCTTGGCTCCATATACGACC
GTCCAGTTTCATCTGTCGTCCAGGTCCAGTCTCAAGGATGAAGCCCGCGTGCGGAAGGGTGCCAGCAGCCCGGGTTCAT
ATAGAGTTATTCAAGTCCCTGAGATCAGAGGTGAGTGTTGGCCTAGAACGGCGAAATTATTGGACAGCCGAAATTATTGGACAGCCGAAGGCGGTTCGCTGTGT
GGAGTTGGATGGTCAGACTGGTCAGACTTGTGGAGCTTGTGCATGCATGTTGGCCTAGAACGGCGAAATTATTGGACAGCCGAAGGCGGTGCAAGATGGGTCAATATGGGGT
TCTCGTGCCGTAATGGTGACTTTTGCTTGTGCCATGTCAGTCCCGTTGCATGCATGTCAGTCCGTTGAGGTGACCTATGACGAGTAA
CAGGACCCTTGACGAGGGGATTAATTTTGCGGATTAATTTTTGCGGATGTCAGTCCCGTTGAGGTGACCTATGACGAGTAA
```

Sequence of codon optimized C7D (SEQ ID NO: 32)

```
ATGTTGTTGGAGCAAATCTGGGGTTTCCTGACTGCACATCCAATCAGTCAGTCACGACGATTTAATCGTATATTTAATCCACATTAC
GCTGAAGCCGCTGAATCGTCGTTGCGTTGGGGGACGTGGGCTTATTCTTCGGCAAGCCCGAATTGAAGGGTTTCTACCGTGAGCGTC
AGCTGGAACGCCTGAAACTTTTGCGCCGTGTGGGAGATATGCCACCTGTATTTCCCAACGGTTGGTATTGTGTTTGCGGAATCGGGAGAAA
```

FIG. 8 (continued)

```
CTGGCTAACAATCAGATCATGGAAATTACAGTTTTAGGTCAGTTCTTAAGCCTTATTCGTAGCGAATCTGGTGCGGTTTACATTACAGA
TTCTTACTGTCCGCCAGAGACAACAACACATTGGTGCGAACTTCAATATCGGCGGCTGTTGCGATAACTGTATCCAGTGTCCCTTCCATGGTGGA
TTTTCTCTGCCGCCAACCGGGAAATGCGTAGAAGTGCCCTATGATGAAGGGCGGAGCATCCCTGAACCAGGCAAAGGTCACCACCTGGCCGTGC
ATCGAACGCAACAACAACATCTATTTATGGTATCACTGTGATGAAGACATGTGCCATATTCATCAAGACAGATTTGTCTGAACAGTTGTCTGAACCGCAGCTTGACATTGCGCACT
CGGCTTTTGGCATCTGGGGACGTACAGAGGACGTAATGTGCCATATATCATCAAGACAGATTTGTCTGAACCAGTTGTTTCGATTTCGGTATTGGG
TAAATTATTACACAAGTCTGCCCCCCGTAAAGGTAAATGGAAGTTAAGAGTGAAGAAGACCGCATTGTTGCCAGGCATGCTATATGTTCGGCCATCTGTCCATATGTGTGTTCCGCCATCTTT
CATGTATGAGGACGGTAAATGGAAGTTAAGAGTGAAGAAGACCGCATTGTTGCCAGGCATGCTGTTCCAGACGTCAATATGTTGTTTCGCCATCTTTCCGAATATCCTTGGTTC
TTATAAGGTCCCCTTGACCAGCTGTTCCAAACGGTTACCGTCAAGCAATGCGATGTGTTAGCGCATGCCGATGTGTTAGCAATTGGGCGCTGTTACCGGCTCAAGCTCGAAGACGCTGCAATAATCCCCTTGGTTC
GAAAAGGGGTGGTGTTCTTTATGACCGTCAAGCAATGCGATGTGTTTAGCGCATGCCGATGTGTTAGCAATTGGGCGCTGTTACCGGAGTAACAAGAAATATTAAGTCACCCCT
GTTGGTCAAGAACGATGCCCCATCCAGAAACATCGTCGCTGGTTTAGCCAATTCTATACCGAGAACTCTATACCGAGAATCTAACCTCACCGAAATGCTGAAGGATG
GATCTCTTTCTAACCAGGCGAAGTCCATCTTCGATTGGTAA
```

Sequence of codon optimized KshB (SEQ ID NO: 33)

```
ATGACTGAGGCGGATAGGCGGATGAACCACTGGGAGATCATGTCTTGGAACTTCAGATAGCGGAAGTTGTAGATGAGACTGACGAGGCCG
GAGTTTAGTATTTGCAGTCCCTGAGGGTCGGACGCGCTGAAATACCGCCAGCCTGACGCTTGTGCTCCCCAGCCTGCCCGTGCTCCTCTTAACGC
TGCGGGCCCTAGCGAGCGCGCAGTGCCAGTGGCCCTATACCGCCAGCCTGACGCATTAGCGATGACGTTCACGTTCTGCCCCTTCGGG
GTAAAGCGTACTGCTGCTCCAACGACACATTGGATGCGGTATGCCAGTAATTGGTTATGTGATCATGCCCAAGTCGGGGATCAGTGTAGTAATTTGCAAAAGTG
CGTTCGTTGGCAAGGCGGGCCGGGGATCAATCGGATGACAGATCGGATGATGACAGATCGGATTGCATTTTTGCCGACGCCGCCTAGCCGCGAGTTG
GCGGCGAAGTACCCCGGACCCGTCAGTTCATCTGTGTTCCATCTGTGTTTTCATCGTCGTTCCAGGTTGCCCTTGAATCTCTTCAAGGTTTGCCCGTCGCCTTAGCCAAATTGGT
TGCTCCATATACGGACCCAGTTCATATAGAGGTATTAGTGATCGATGACACTGAGGCCGGCAGCCGACCCCGTTCCGCGCGGGCTGTTAAGCCCGGATGCCATTGAAGGTGC
CAGCACAGCAGGTTCATATAGAGGTATTAGTGATCGATGAGTTGGATGTCAGATCAGAGGGTTGATGATGCGCCTAGAACGGCAAGTCGAATCAAGGTCGAATCAACGGTTGG
CCAGCCACTGCTGCTCCAACGACACATTGGATGCGGTATGACTTTTTTTGCTCTAACGCCAAGTCGGGATCAGTGTAGTAATTTGCAAAAGTG
GGGACTTGACGCTCCCGTTCTCGTGGCCTGTGAGGCTCTGCATTTGTGGAGCTTGTTGCGGCAAGGCATTTGGATGCCCTTGAGAGGA
ATGACGTGCTGAGCAGCAGGAGGAGCCCTTGACGCAGGGCATTAATTTTGGCGAAGTCAATATGGGGGTCAGCAGGATTAATTTTTGGCGAAGTCAATATGGGGGTCA
GACGAGTAA
```

FIG. 9

Wild-type *Drosophila melanogaster* C7D (SEQ ID NO: 26)
MTSYSLFWMSLLKNNWKPISNDFVICLWTLAVTFIRIYWIFFVPLEWKKDLDNEKWSFLRKTENVVCYNHKRDTINRLRKLKIQKIIEL
PPPYPNGWYGILKSSQLKAGEATCVSCLGEDLVIFRSKKDIVFILDAYCPHLGANLGIGGSVADDCVICPFHQWKFRGTDGLCINIPYS
TSVPKGSKLKKWISQEVDGFIFIWYHAEQTELPWDLPVPMGEIDDTFVYHGHNEFYINCHIQEIPENGADIAHFNAIHKKNFINGSWAQ
KKRLFGLGSHHWKARWSPFTGKLKYLAEVNLSHTEKLFGKFGCFRMEVSGKQIGPSIVCLEVNSYTFGKIKVFQYITPIEPMLQKVVHE
FYGPRWIAPLMKIFIYGESLMFERDIKIWNHKVFNRNPILAKEDASIKKFRLWFSQFYSSNSKIYSEATNIGW Wild-type *Tetrahymena thermophila* C7D (SEQ ID NO: 27)
MIEFNKECLMDILKNQDYHFYMVIPLIFIGLYALYIKKFKYNPIEKQEWDDRRSNVKRGNPPPSYPNGWFRVCHKNELQIGQSKFFKL
NGRHITVFRGEDGIPYALHAYCSHMGANLGIGGKVKWNSCIECPFHGWSFDGKSGKCVNSEHLDEKQCTHHTYHDIKKMTKGSDNRYIK
TCESGSPSQIQKFHVRQQNNLIYVWFHAKNVDPYYEPFEINEIPYLEDRGETADYVNCQIQEIPENGADFKHFEYVHYAWIEILFPWIK
FKWVPKDRKPTDKDFDEVMRTHPNKKVQAFSNKLFDKYTNEQNKTHINNLVLDAYLVFFDKFEFYIQTATVFQLGSGTVFLFKFPIWE
AVVVQSVTPVGKFNQLVHHKMYTSWWLPYWVSAYLLAGFRKQFISDKIVWNNKIFADKLTYNPKAVFDERLLNWREWYSQYYEGCDEFE
KNQEAFDW Wild-type *Bombyx mori* C7D (SEQ ID NO: 28)
MADRQHFPSAITEAVSSNTACPDTGPKAETTNIFLLQRNITIESSKHVFSSIVEYILILTLMEAFSAILYVIYKSYISPVFYKKELTE
VGFDHIPQGPDKGRRISRAQASRRMGSKLPPPYPNGWFAVAETRELKVGSVLSIDALGQNLCVYRGEDGLARCVDAYCPHLGANLAVGG
TVRGSCIECPFHKWRFNAAGTCVSLPGSDIAPKGVSIRTWCVVETDGAIWIWHDAEGREPLWEITDPPELKDFGYRGRNEFEVSAHIQE
IPENGADVPHLNAVHSSSLLSDLGERYPVLHEIIGRHVWNNADWTKSDDHTSLMHITQEYKVLKYDLLARIDVKVTQIGPGHVRLFLKTSV
GPFYIAQSVTPLGPLLQKVIHRVYSPAYNAPVGAFLVRCEAYMFERDVTIWNSKRFVSAPAYVKTDKTIRTFRNWFGQFYSEHSLSFRD
ALQNPLDW Wild-type *Pseudomonas putida* VanB (SEQ ID NO: 29)
MIDAVVVSRNDEAQDICSFELAAVDGSLLRFSAGAHIDVHLPEGQVRQYSLCNHPEERHRYLIGVLKDPASRGGSRSLHEQIHNGARLR
ISAPRNLFPLAQGARRSLLFAGGIGITPILCMAEQLAASADFELHYCARSSERAAFIERMRGAAFADRLFVHFDEQPETALDIAQVLAN
PQADVHLYVCGPGGFMQHVLESAKAQGWQEACLHREYFAAAPVDTQGDGSFSVQLNSTGQVFEVPADQSVVHVLEQHGIAIAMSCEQGI
CGTCLTRVLSGTPEASRPVFLTEQEQALNDQFTPCCSRSKTPLLVLDL Wild-type *Rhodococcus erythropolis* KshB (SEQ ID NO: 30)

FIG. 9 (continued)

MTTVEVPHSSRSAVLTVSGVIEETSDARSLVFEIPAELKDKFDYKPGQFLTLRIPSDQTGSVARCYSLASSPFTDDAPKVTVKRTVDGY
GSNWLCDKLQVGDTIEVLPPSGVFTPKSLDHDFLLFGAGSGITPVISILKSALTQGSGNVVLIYANRDEKSVIFGAELRELAAQHPGRL
TVVHWIETVQGLPAVSQLATLAKPFVAYEAFMCGPGPFMDAVHKALAEAGMPRTQVHAEVFNSLAGDPFRDVEVAEVSDEEAADAATVE
VELDGETHTLVWPRKQTLVDIMLAKGLDVPYSCKEGESGSCACTVTEGEVQMDNSEILDAEDVANGYILGCKRSRSPIA

Wild-type Rhodococcus rhodochrous KshB (SEQ ID NO: 31)
MTTVEVPHGSRSVILTVSAVVEETADTRSIVFAVPDELRDKFAYRPGQFLTLRIPSDRTGSVARCYSLASSPFTDDAPKVTVKRTSDGY
GSNWLCDNIATGQTLEVLPPAGVFTPKSLDHDFLLFGAGSGITPVISILKSALTQGGGKVVLVYANRDEKSVIFAELRALAEKYPTRL
TVVHWLESVQGLPTADQLAATAAPYESYEAFMCGPGPFMDTVHQALNTVGMPRARVHAEVFNSLSGDPFADQAPVEVSDEDAADAATVE
VELDGEVHKLSWPRKQTLVDIMLAKGIDVPYSCQEGECGSCACTVLEGKVEMENCDVLDPEDIEAGYILGCQARPVTDHLKIEF Linker sequence 1 (SEQ ID NO: 9)
GGGGS Linker sequence 2 (SEQ ID NO: 10)
EAAAK HIS-tag (C-terminal) (SEQ ID NO: 11)
AAALEHHHHHH HIS-tag (N-terminal) (SEQ ID NO: 12)
HHHHHHSSGLVPRGSH

TIR1 (SEQ ID NO: 13)
GTTATCATGGGTAGC

TIR2 (SEQ ID NO: 14)
GCAGCTATGCAGCTT

HIS-tag (SEQ ID NO: 35)
HHHHHH

FUSION POLYPEPTIDES FOR PRODUCTION OF 7-DEHYDROCHOLESTEROL AND METHODS OF USE THEREOF

CLAIM OF PRIORITY

This application claims priority to International Application No. PCT/CN2023/101041, filed on Jun. 19, 2023. The entire contents of the foregoing application are incorporated herein by reference.

TECHNICAL FIELD

This disclosure relates to genetically engineered microbes expressing fusion proteins including an iron-sulfur protein and a ferredoxin reductase. The microbes can convert cholesterol to 7-dehydrocholesterol (7-DHC) with a high efficiency.

SEQUENCE LISTING

This application contains a Sequence Listing that has been submitted electronically as an XML file named "50548-0004001_SL_ST26.xml." The XML file, created on Jun. 16, 2023, is 52,350 bytes in size. The material in the XML file is hereby incorporated by reference in its entirety.

BACKGROUND

There are thousands of industrially important iron-sulfur proteins that catalyze a diverse set of chemical reactions. Cytochrome P450 and Rieske non-heme iron dependent oxygenase are two important classes of these metalloproteins. Cholesterol 7-desaturase is a Rieske oxygenase originally identified in insects and also observed in multiple other species. It has the unique ability to irreversibly catalyze the oxidation of cholesterol to 7-dehydrocholesterol (7-DHC). 7-DHC is a precursor to desirable Vitamin D3. However, the activity of cholesterol 7-desaturase is very low when expressed in heterologous organisms. There is a need to improve the activities of the enzymes.

SUMMARY

The present disclosure demonstrates that fusing cholesterol 7-desaturase with a ferredoxin reductase can lead to a highly active enzyme complex for 7-DHC production. Also provided herein are engineered microbial cells, cultures of the microbial cells, and methods for the production of 7-DHC.

In one aspect, the disclosure is related to a fusion polypeptide, comprising a first moiety comprising an iron-sulfur protein that can convert cholesterol to 7-dehydrocholesterol (7-DHC), and a second moiety comprising a ferredoxin reductase. In some embodiments, the iron-sulfur protein is cholesterol 7-desaturase (C7D). In some embodiments, the C7D is derived from *Caenorhabditis elegans* C7D, *Drosophila melanogaster* C7D, *Tetrahymena thermophila* C7D, or *Bombyx mori* C7D. In some embodiments, the C7D comprises an amino acid sequence that is at least 70%, 75%, 80%, 85%, 90%, 95%, 96%, 97%, 98%, 99%, or 100% identical to SEQ ID NO: 1, 3, 4, 26, 27, or 28. In some embodiments, the fusion polypeptide comprises a HIS-tag at C-terminus of C7D. In some embodiments, the ferredoxin reductase is derived from *Mycobacterium tuberculosis* 3-ketosteroid-9-alpha-monooxygenase, ferredoxin reductase component (KshB), *Pseudomonas putida* vanillate O-demethylase oxidoreductase (VanB), *Rhodococcus erythropolis* oxygenase reductase (KshB), or *Rhodococcus rhodochrous* 3-ketosteroid-9-alpha-monooxygenase, ferredoxin reductase component (KshB). In some embodiments, the ferredoxin reductase comprises an amino acid sequence that is at least 70%, 75%, 80%, 85%, 90%, 95%, 96%, 97%, 98%, 99%, or 100% identical to SEQ ID NO: 7, 8, 29, 30, or 31. In some embodiments, the fusion polypeptide comprises from N-terminus to C-terminus, the first moiety and the second moiety.

In some embodiments, the first moiety is fused with the second moiety with a linker. In some embodiments, the linker is a flexible linker. In some embodiments, the flexible linker comprises an amino acid sequence that is at least 80%, 90%, 95%, or 100% identical to SEQ ID NO: 25. In some embodiments, the linker is a rigid linker. In some embodiments, the rigid linker comprises an amino acid sequence that is at least 80%, 90%, 95%, or 100% identical to SEQ ID NO: 24. In some embodiments, the fusion polypeptide comprises an amino acid sequence that is at least 70%, 75%, 80%, 85%, 90%, 95%, 96%, 97%, 98%, 99%, or 100% identical to SEQ ID NO: 15, 16, 17, or 18.

In one aspect, the disclosure is related to a fusion polypeptide comprising from N-terminus to C-terminus: (a) *Caenorhabditis elegans* C7D; (b) a flexible linker; and (c) *Mycobacterium tuberculosis* KshB, In some embodiments, the *Caenorhabditis elegans* C7D comprises an amino acid sequence that is at least 70%, 75%, 80%, 85%, 90%, 95%, 96%, 97%, 98%, 99%, or 100% identical to SEQ ID NO: 4; in some embodiments, the flexible linker comprises an amino acid sequence that is at least 80%, 90%, 95%, or 100% identical to SEQ ID NO: 25; and in some embodiments, the ferredoxin reductase comprises an amino acid sequence that is at least 70%, 75%, 80%, 85%, 90%, 95%, 96%, 97%, 98%, 99%, or 100% identical to SEQ ID NO: 7. In some embodiments, the *Caenorhabditis elegans* C7D comprises an amino acid sequence that is at least 70%, 75%, 80%, 85%, 90%, 95%, 96%, 97%, 98%, 99%, or 100% identical to SEQ ID NO: 6; in some embodiments, the flexible linker comprises an amino acid sequence that is at least 80%, 90%, 95%, or 100% identical to SEQ ID NO: 25; and in some embodiments, the ferredoxin reductase comprises an amino acid sequence that is at least 70%, 75%, 80%, 85%, 90%, 95%, 96%, 97%, 98%, 99%, or 100% identical to SEQ ID NO: 7.

In one aspect, the disclosure is related to a fusion polypeptide comprising from N-terminus to C-terminus: (a) *Caenorhabditis elegans* C7D; (b) a rigid linker; and (c) *Mycobacterium tuberculosis* KshB, In some embodiments, the *Caenorhabditis elegans* C7D comprises an amino acid sequence that is at least 70%, 75%, 80%, 85%, 90%, 95%, 96%, 97%, 98%, 99%, or 100% identical to SEQ ID NO: 4; in some embodiments, the rigid linker comprises an amino acid sequence that is at least 80%, 90%, 95%, or 100% identical to SEQ ID NO: 24; and in some embodiments, the ferredoxin reductase comprises an amino acid sequence that is at least 70%, 75%, 80%, 85%, 90%, 95%, 96%, 97%, 98%, 99%, or 100% identical to SEQ ID NO: 7. In some embodiments, the *Caenorhabditis elegans* C7D comprises an amino acid sequence that is at least 70%, 75%, 80%, 85%, 90%, 95%, 96%, 97%, 98%, 99%, or 100% identical to SEQ ID NO: 6; in some embodiments, the rigid linker comprises an amino acid sequence that is at least 80%, 90%, 95%, or 100% identical to SEQ ID NO: 24; and in some embodiments, the ferredoxin reductase comprises an amino acid sequence that is at least 70%, 75%, 80%, 85%, 90%, 95%, 96%, 97%, 98%, 99%, or 100% identical to SEQ ID NO: 7.

In one aspect, the disclosure is related to a polynucleotide comprising a nucleic acid encoding the fusion polypeptide described herein.

In one aspect, the disclosure is related to a polynucleotide comprising from 5' end to 3' end: (a) a first nucleic acid encoding an iron-sulfur protein that can convert cholesterol to 7-dehydrocholesterol (7-DHC), (b) optionally a second nucleic acid encoding a linker; and (c) a third nucleic acid encoding a ferredoxin reductase. In some embodiments, the first nucleic acid and/or the third nucleic acid are codon optimized for E. coli expression. In some embodiments, the first nucleic acid comprises a sequence that is at least 70%, 75%, 80%, 85%, 90%, 95%, 96%, 97%, 98%, 99%, or 100% identical to SEQ ID NO: 32, and/or the third nucleic acid comprises a sequence that is at least 70%, 75%, 80%, 85%, 90%, 95%, 96%, 97%, 98%, 99%, or 100% identical to SEQ ID NO: 33. In some embodiments, the second nucleic acid comprises a sequence that is at least 70%, 75%, 80%, 85%, 90%, 95%, 96%, 97%, 98%, 99%, or 100% identical to SEQ ID NO: 22 or SEQ ID NO: 23. In some embodiments, the polynucleotide comprises a sequence that is at least 70%, 75%, 80%, 85%, 90%, 95%, 96%, 97%, 98%, 99%, or 100% identical to SEQ ID NO: 19, 20, 21, or 34.

In one aspect, the disclosure is related to a vector comprising the polynucleotide described herein. In some embodiments, the vector comprises a TIR1 or TIR2 translational initiation region.

In one aspect, the disclosure is related to an engineered microbial cell expressing the fusion polypeptide described herein.

In one aspect, the disclosure is related to an engineered microbial cell comprising the polynucleotide or the vector described herein. In some embodiments, the engineered microbial cell described herein further expresses (a) an alcohol dehydrogenase (ADH), and/or (b) a glucose oxidase. In some embodiments, the cell is a bacterial cell. In some embodiments, the bacterial cell is E. coli cell. In some embodiments, the E. coli cell has C43 (DE3), JM109 (DE3), W3110 (DE3), BL21 (DE3), or C41 (DE3) background.

In one aspect, the disclosure is related to a culture of engineered microbial cells comprising the engineered microbial cell described herein.

In one aspect, the disclosure is related to a method for producing 7-DHC, comprising culturing the engineered microbial cell described herein under conditions suitable for producing 7-DHC. In some embodiments, the method additionally comprises recovering 7-DHC from the culture. In some embodiments, the method further comprises adding isopropanol and/or glucose to the culture. In some embodiments, the method comprises adding polymyxin B to the culture. In some embodiments, the concentration of polymyxin B is at least 32 mg/L, at least 64 mg/L, at least 96 mg/L, at least 128 mg/L, at least 160 mg/L, or at least 192 mg/L. In some embodiments, the 7-DHC can be produced at a concentration of greater than 10 mg/L, greater than 20 mg/L, greater than 30 mg/L, greater than 40 mg/L, greater than 50 mg/L, greater than 60 mg/L, greater than 70 mg/L, greater than 80 mg/L, greater than 85 mg/L, or greater than 90 mg/L, per 100 mg/L cholesterol.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2 is a table summarizing the sequences of C7D, KshB, and/or C7D-KshB fusion proteins expressed by different E. coli strains in Example 1.

FIG. 7 lists amino acid sequences of C7D, KshB, and fusion variants discussed in Example 1.

FIG. 8 lists nucleotide sequences discussed in the disclosure.

FIG. 9 lists additional sequences discussed in the disclosure.

DETAILED DESCRIPTION

Figure 1:
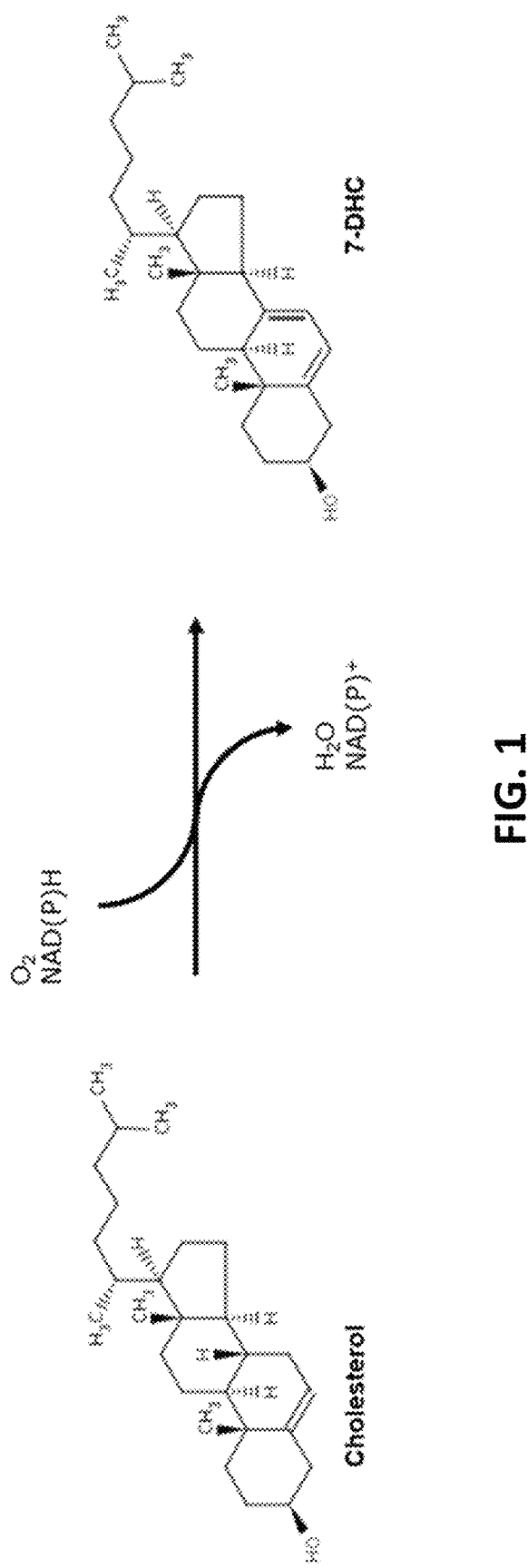
FIG. 1 shows the oxidation reaction catalyzed by cholesterol 7-desaturase to generate 7-dehydrocholesterol (7-DHC). The chemical structures of cholesterol and 7-DHC are provided.

This disclosure describes methods for the production of 7-dehydrocholesterol (7-DHC) via fermentation by a microbial host. For example, a fusion protein including an iron-sulfur protein (or a variant thereof) and a ferredoxin reductase (or a variant thereof) can be expressed by suitable microbial cells (e.g., E. coli strains), for large-scale production of 7-DHC. Additional enzymes can also be introduced into the microbial cells, e.g., alcohol dehydrogenase (ADH) and/or glucose oxidase, to supply electron sources (e.g., NAD(P)H). The fermentation can also include polymyxin B to further boost 7-DHC yield.

The term "fermentation" is used herein to refer to a process whereby a microbial cell converts one or more substrate(s) into a desired product (e.g., 7-DHC) by means of one or more biological conversion steps, without the need for any non-biological conversion step.

The term "variant" refers to molecules with some differences, generated synthetically or naturally, in their nucleotide or amino acid sequences as compared to a reference polynucleotide or polypeptide, respectively. These differences include substitutions, insertions, deletions or any desired combination of such modifications.

The term "engineered" is used herein, with reference to a cell, to indicate that the cell contains at least one targeted genetic alteration introduced by man that distinguishes the engineered cell from the naturally occurring cell.

The term "native" is used herein to refer to a cellular component, such as a polynucleotide or polypeptide, that is naturally present in a particular cell. A native polynucleotide or polypeptide is endogenous to the cell.

When used with reference to a polynucleotide or polypeptide, the term "non-native" refers to a polynucleotide or polypeptide that is not naturally present in a particular cell.

When used with reference to the context in which a gene is expressed, the term "non-native" refers to a gene expressed in any context other than the genomic and cellular context in which it is naturally expressed. A gene expressed in a non-native manner may have the same nucleotide sequence as the corresponding gene in a host cell, but may be expressed from a vector or from an integration point in the genome that differs from the locus of the native gene.

The term "heterologous" is used herein to describe a polynucleotide or polypeptide introduced into a host cell. This term encompasses a polynucleotide or polypeptide, respectively, derived from a different organism, species, or strain than that of the host cell. In this case, the heterologous polynucleotide or polypeptide has a sequence that is different from any sequence(s) found in the same host cell. However, the term also encompasses a polynucleotide or polypeptide that has a sequence that is the same as a sequence found in the host cell, wherein the polynucleotide or polypeptide is present in a different context than the native sequence (e.g., a heterologous polynucleotide can be linked to a different promotor and inserted into a different genomic location than that of the native sequence). "Heterologous expression" thus encompasses expression of a sequence that is non-native to the host cell, as well as expression of a sequence that is native to the host cell but in a non-native context.

As used with reference to polynucleotides or polypeptides, the term "wild-type" refers to any polynucleotide having a nucleotide sequence, or polypeptide having an amino acid sequence present in a polynucleotide or polypeptide from a naturally occurring organism, regardless of the source of the molecule; i.e., the term "wild-type" refers to sequence characteristics, regardless of whether the molecule is purified from a natural source; expressed recombinantly, followed by purification; or synthesized. The term "wild-type" is also used to denote naturally occurring cells.

A "control cell" is a cell that is otherwise identical to an engineered cell being tested, including being of the same genus and species as the engineered cell, but lacks the specific genetic modification(s) being tested in the engineered cell.

As used herein, unless otherwise indicated, the enzymes (e.g., cholesterol 7-desaturase and ferredoxin reductase) in the disclosure includes the wildtype enzymes and the variants thereof. A variant can have at least 60%, 65%, 70%, 75%, 80%, 85%, 90%, 95%, 96%, 97%, 98%, 99%, or 100% amino acid sequence identity to the wildtype enzyme, but the variant retains similar functions or activities or even can have improved functions or activities. For example, the "cholesterol 7-desaturase" enzyme catalyzes conversion of cholesterol to 7-dehydrocholesterol. The term "cholesterol 7-desaturase" includes the wildtype cholesterol 7-desaturase and the variants thereof, wherein the variants have substantially similar or even better functions or activities. Similarly, the "ferredoxin reductase" enzyme includes the wildtype ferredoxin reductase and the variants thereof, wherein the variants have substantially similar or even better functions or activities. Similarly, *Caenorhabditis elegans* C7D, *Drosophila melanogaster* C7D, *Tetrahymena thermophila* C7D, *Bombyx mori* C7D, *Mycobacterium tuberculosis* 3-ketosteroid-9-alpha-monooxygenase, ferredoxin reductase component (KshB), *Pseudomonas putida* vanillate O-demethylase oxidoreductase (VanB), *Rhodococcus erythropolis* oxygenase reductase (KshB), or *Rhodococcus rhodochrous* 3-ketosteroid-9-alpha-monooxygenase, ferredoxin reductase component (KshB), etc., include the wildtype enzymes and the respective variants thereof.

Enzymes are identified herein by the reactions they catalyze and, unless otherwise indicated, refer to any polypeptide capable of catalyzing the identified reaction. Unless otherwise indicated, enzymes may be derived from any organism and may have a native or mutated amino acid sequence. As is well known, enzymes may have multiple functions and/or multiple names, sometimes depending on the source organism from which they derive. The enzyme names used herein encompass orthologs, including enzymes that may have one or more additional functions or a different name.

The term "7-dehydrocholesterol" refers to a chemical compound of the formula $C_{27}H_{44}O$ (CAS #: 434-16-2).

The term "sequence identity," in the context of two or more amino acid or nucleotide sequences, refers to two or more sequences that are the same or have a specified percentage of amino acid residues or nucleotides that are the same, when compared and aligned for maximum correspondence, as measured using a sequence comparison algorithm or by visual inspection.

For sequence comparison to determine percent nucleotide or amino acid sequence identity, typically one sequence acts as a "reference sequence," to which a "test" sequence is compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence relative to the reference sequence, based on the designated program parameters. Alignment of sequences for comparison can be conducted using BLAST set to default parameters.

The term "titer," as used herein, refers to the mass of a product (e.g., 7-DHC) produced by a culture of microbial cells divided by the culture volume.

As used herein with respect to recovering 7-DHC from a cell culture, "recovering" refers to separating the 7-DHC from at least one other component of the cell culture medium.

7-dehydrocholesterol

The zoosterol 7-dehydrocholesterol (7-DHC) is a cholesterol precursor found in the serum that is used for synthesizing provitamin-D3. It is converted to vitamin D3 in human skin via the intermediate isomer pre-vitamin D3 under the action of ultraviolet rays from sun light. Vitamin D deficiency increases the risk of different cancers, Type 1 diabetes, multiple sclerosis, and hypertension. Consequently, adequate vitamin D3 intake is essential for maintaining musculoskeletal health, calcium homeostasis bone homeostasis, and physical performance. Vitamin D is reported to reduce the risk of immune disorders and cardiovascular disease. It is beneficial in treating damaged beta cells because vitamin D is an important modulator of both inflammation and beta cell survival, and therefore has potential to treat diabetes.

Traditionally, 7-DHC is produced by chemical synthesis and biocatalytic reactions. Microbial production of 7-DHC from glucose has been recognized as an attractive complement to the traditional sources, which rely on chemical synthesis and biotransformation. Several studies have revealed that conversion of cholesterol into 7-DHC, catalyzed by Rieske-type oxygenases belonging to the neverland/DAF-36 (NVD) family, is a crucial step in steroid hormone biosynthesis in insects and nematodes. These enzymes contain a typical iron-sulfur center and are highly conserved among invertebrates, including *Drosophila* sp., *Bombyx mori, Caenorhabditis elegans*, and *Tetrahymena thermophila*. In these organisms, they are important for the synthesis of dafachronic acids and ecdysteroides. Furthermore, the lethality of neverland/DAF-36 knockout in the fruit fly *Drosophila melanogaster* can be rescued by other DAF-36/neverland genes or supplementation with 7-DHC. Therefore, DAF-36/neverland is a potential regulatory node for the partitioning of cholesterol to steroidogenic and bile acid pathways, thereby influencing development and longevity.

However, the expression of NVD protein in engineered *Escherichia coli* has failed due to the persistent formation of inclusion bodies, even after codon optimization. Previous reports have cloned the NVD gene with sequences encoding various fusion tags (e.g., MBP and HIS tags), such that soluble NVD proteins can be expressed in *E. coli* and purified. Details can be found, e.g., in Zhu, Z., et al. "Soluble expression, purification and biochemical characterization of a C-7 cholesterol dehydrogenase from *Drosophila melanogaster.*" *Steroids* 152 (2019): 108495, which is incorporated herein by reference in its entirety.

Fusion Proteins

Provided herein are fusion proteins having a first moiety and a second moiety. In some embodiments, the first moiety includes an iron-sulfur protein that can convert cholesterol to 7-dehydrocholesterol (7-DHC). In some embodiments, the iron-sulfur protein is a Rieske oxygenase. In some embodiments, the iron-sulfur protein is a Rieske protein. In some embodiments, the iron-sulfur protein can irreversibly catalyze the oxidation of cholesterol to 7DHC. In some embodiments, the iron-sulfur protein is cholesterol 7-desaturase (e.g., any of the C7D enzymes or variants thereof). In some embodiments, the second moiety includes a ferredoxin reductase. In some embodiments, the ferredoxin reductase is KshB (e.g., any of the KshB enzymes or variants thereof) or VanB (e.g., any of the VanB enzymes or variants thereof).

In some embodiments, the fusion protein or fusion polypeptide described herein includes, from N-terminus to C-terminus, a cholesterol 7-desaturase, optionally a linker, and a ferredoxin reductase. In some embodiments, the fusion protein or fusion polypeptide includes an amino acid sequence that is at least 70%, 75%, 80%, 85%, 90%, 95%, 96%, 97%, 98%, 99%, or 100% identical to Fusion Variant 1 (SEQ ID NO: 15), Fusion Variant 2 (SEQ ID NO: 16), Fusion Variant 3 (SEQ ID NO: 17), or Fusion Variant 4 (SEQ ID NO: 18). In some embodiments, the fusion protein or fusion polypeptide described herein includes any of the sequences in FIG. 7.

In some embodiments, the fusion protein or fusion polypeptide described herein includes, from N-terminus to C-terminus, (a) a non-native C7D (e.g., any one of the C7D described herein); (b) a flexible linker (e.g., any one of the flexible linkers described herein); and (c) a non-native KshB (e.g., any one of the KshB described herein). In some embodiments, the fusion protein or fusion polypeptide described herein includes, from N-terminus to C-terminus, (a) a non-native C7D (e.g., any one of the C7D described herein); (b) a rigid linker (e.g., any one of the rigid linkers described herein); and (c) a non-native KshB (e.g., any one of the KshB described herein). In some embodiments, the non-native C7D is derived from *Caenorhabditis. elegans*. In some embodiments, the non-native KshB is derived from *Mycobacterium tuberculosis*.

In some embodiments, the fusion protein or fusion polypeptide described herein includes, from N-terminus to C-terminus, (a) a non-native C7D (e.g., any one of the C7D described herein); (b) a flexible linker (e.g., any one of the flexible linkers described herein); and (c) a non-native VanB (e.g., any one of the VanB described herein). In some embodiments, the fusion protein or fusion polypeptide described herein includes, from N-terminus to C-terminus, (a) a non-native C7D (e.g., any one of the C7D described herein); (b) a rigid linker (e.g., any one of the rigid linkers described herein); and (c) a non-native VanB (e.g., any one of the VanB described herein). In some embodiments, the non-native C7D is derived from *Caenorhabditis. elegans*. In some embodiments, the non-native VanB is derived from *Pseudomonas putida*.

In some embodiments, the non-native C7D is encoded by a nucleic acid sequence that is codon optimized for expression in a microbial cell (e.g., *E. coli*). In some embodiments, the nucleic acid sequence is at least 70%, 75%, 80%, 85%, 90%, 95%, 96%, 97%, 98%, 99%, or 100% identical to SEQ ID NO: 32.

In some embodiments, the non-native KshB is encoded by a nucleic acid sequence that is codon optimized for expression in a microbial cell (e.g., *E. coli*). In some embodiments, the nucleic acid sequence is at least 70%, 75%, 80%, 85%, 90%, 95%, 96%, 97%, 98%, 99%, or 100% identical to SEQ ID NO: 33.

In some embodiments, the fusion protein or fusion polypeptide described herein is encoded by a nucleic acid sequence that is codon optimized for expression in a microbial cell (e.g., *E. coli*). In some embodiments, the nucleic acid sequence is codon optimized to expression Fusion Variant 1, wherein the nucleic acid sequence is at least 70%, 75%, 80%, 85%, 90%, 95%, 96%, 97%, 98%, 99%, or 100% identical to SEQ ID NO: 19. In some embodiments, the nucleic acid sequence is codon optimized to expression Fusion Variant 2, wherein the nucleic acid sequence is at least 70%, 75%, 80%, 85%, 90%, 95%, 96%, 97%, 98%, 99%, or 100% identical to SEQ ID NO: 20. In some embodiments, the nucleic acid sequence is codon optimized to expression Fusion Variant 3, wherein the nucleic acid sequence is at least 70%, 75%, 80%, 85%, 90%, 95%, 96%, 97%, 98%, 99%, or 100% identical to SEQ ID NO: 34. In some embodiments, the nucleic acid sequence is codon optimized to expression Fusion Variant 4, wherein the nucleic acid sequence is at least 70%, 75%, 80%, 85%, 90%, 95%, 96%, 97%, 98%, 99%, or 100% identical to SEQ ID NO: 21. In some embodiments, the fusion protein or fusion polypeptide described herein is encoded by any of the sequences in FIG. 8.

Cholesterol 7-desaturase (C7D, or NVD)

FIG. 1 shows the catalytic reaction catalyzed by C7D for the conversion of cholesterol to 7-DHC. Specifically, using oxygen, NAD(P)H, and cholesterol as reactants, C7D oxidizes the 7,8 position to produce water, NAD(P)+, and 7-dehydrocholesterol.

In some embodiments, the C7D is derived from *Caenorhabditis elegans* C7D (UniProt ID: Q17938), *Drosophila melanogaster* C7D (UniProt ID: Q1JUZ1), *Tetrahymena thermophila* C7D (UniProt ID: I7ML19), or *Bombyx mori* C7D (UniProt ID: H9IWP6). In some embodiments, the C7D described herein is a wild-type C7D or a variant thereof.

In some embodiments, the *Caenorhabditis elegans* C7D includes an amino acid sequence that is at least 70%, 75%, 80%, 85%, 90%, 95%, 96%, 97%, 98%, 99%, or 100% identical to SEQ ID NO: 1, SEQ ID NO: 3, or SEQ ID NO: 4. In some embodiments, the fusion protein or fusion polypeptide described herein includes a HIS-tag at the C-terminus of C7D. In some embodiments, the C7D with a C-terminal HIS-tag has an amino acid sequence that is at least 70%, 75%, 80%, 85%, 90%, 95%, 96%, 97%, 98%, 99%, or 100% identical to SEQ ID NO: 2, SEQ ID NO: 5, or SEQ ID NO: 6.

In some embodiments, the *Drosophila melanogaster* C7D includes an amino acid sequence that is at least 70%, 75%, 80%, 85%, 90%, 95%, 96%, 97%, 98%, 99%, or 100% identical to SEQ ID NO: 26. In some embodiments, the *Tetrahymena thermophila* C7D includes an amino acid sequence that is at least 70%, 75%, 80%, 85%, 90%, 95%, 96%, 97%, 98%, 99%, or 100% identical to SEQ ID NO: 27. In some embodiments, the *Bombyx mori* C7D includes an amino acid sequence that is at least 70%, 75%, 80%, 85%, 90%, 95%, 96%, 97%, 98%, 99%, or 100% identical to SEQ ID NO: 28.

KshB

In some embodiments, the ferredoxin reductase described herein is KshB or a variant thereof. KSH is a two-component class IA type monooxygenase involved in microbial steroid catabolism and is encoded by a Rieske oxygenase (KshA) and a ferredoxin reductase (KshB). KshA contains a Rieske [2Fe-2S] cluster and mononuclear ferrous iron, while KshB also contains [2Fe-2S] cluster, and it requires nicotinamide adenine dinucleotide (NADH) and flavin adenine dinucleotide (FAD) as the electron donors and transfer. KSH enzyme systems are important in the cleavage of steroid nucleus in microorganisms, e.g., *Rhodococcus erythropolis* SQ1, *R. rhodochrous* DSM43269, and *Mycobacterium tuberculosis* H37Rv, whereas 4-androstene-3,17-dione (AD) and androsta-1,4-diene-3,17-dione (ADD) can be stably accumulated by genetic inactivation of KSH in *M. tuberculosis*. The biochemical characterization of KSH has been investigated by heterologous expression in *Escherichia coli*. The activity of KshA, unfortunately, is almost entirely lost after purification due to its instability. However, co-expression of KshA and KshB in *E. coli* can enhance the stability of KshA and increase the hydroxylation activity of KSH, which demonstrates a protein-protein interaction between them. The deletion of the Rieske oxygenase gene in *R. erythropolis* SQ1 abolished the ability to grow on the AD and ADD, indicating that these two components were essential.

In the hydroxylation of steroids, the electrons transferred from NAD(P)H by a ferredoxin reductase are required. The KshB in a KSH system is responsible for donating electrons from NADH and transferring them to KshA via a [2Fe-2S] cluster domain. The cofactor NAD(P)H is essential due to its high cost for application in chemical and pharmaceutical industries, and the bioconversion should not occur when NADH is consumed up in vitro. Therefore, the NAD(P)H regeneration systems should be established as more economical processes in preparative biotransformation. The enzymatic regeneration mode of NAD(P)H has been widely developed using alcohol dehydrogenases (ADH), hydroxy acid dehydrogenases, and several other dehydrogenases, of which formate dehydrogenase (FDH) and glucose dehydrogenase (GDH) are commonly used.

Although detailed information has been obtained about KSH in some microorganisms, attempts to modify this KSH system for desirable sterol substrates in high purity and productivity have rarely been successful. In Zhu, Z., et al. "Development of engineered ferredoxin reductase systems for the efficient hydroxylation of steroidal substrates." *ACS Sustainable Chemistry & Engineering* 8.44 (2020): 16720-16730, an efficient whole-cell catalyst was constructed with considerable production and yield by modification of a Rieske [2Fe-2S] cluster in toluene 2,3-dioxygenase (TDO) with increased efficiency of electron transfer. Details of the electron transfer system for these steroid hydroxylation reactions and NADH regeneration systems can be found in this article, which is incorporated herein by reference in its entirety.

In some embodiments, the KshB is derived from *Mycobacterium tuberculosis* 3-ketosteroid-9-alpha-monooxygenase, ferredoxin reductase component (KshB; UniProt ID: P9WJ93), *Rhodococcus erythropolis* oxygenase reductase (KshB; UniProt ID: Q8KQH9), or *Rhodococcus rhodochrous* 3-ketosteroid-9-alpha-monooxygenase, ferredoxin reductase component (KshB; UniProt ID: B6V6V6). In some embodiments, the ferredoxin reductase described herein is a KshB or a variant thereof.

In some embodiments, the *Mycobacterium tuberculosis* KshB includes an amino acid sequence that is at least 70%, 75%, 80%, 85%, 90%, 95%, 96%, 97%, 98%, 99%, or 100% identical to SEQ ID NO: 7 or SEQ ID NO: 8. In some embodiments, the *Rhodococcus erythropolis* KshB includes an amino acid sequence that is at least 70%, 75%, 80%, 85%, 90%, 95%, 96%, 97%, 98%, 99%, or 100% identical to SEQ ID NO: 30. In some embodiments, the *Rhodococcus rhodochrous* KshB includes an amino acid sequence that is at least 70%, 75%, 80%, 85%, 90%, 95%, 96%, 97%, 98%, 99%, or 100% identical to SEQ ID NO: 31.

VanB

In some embodiments, the ferredoxin reductase described herein is VanB or a variant thereof. In some embodiments, the VanB is derived from *Pseudomonas putida* vanillate 0-demethylase oxidoreductase (VanB; UniProt ID: O54037). In some embodiments, the ferredoxin reductase described herein described herein is a VanB or a variant thereof. In some embodiments, the *Pseudomonas putida* VanB includes an amino acid sequence that is at least 70%, 75%, 80%, 85%, 90%, 95%, 96%, 97%, 98%, 99%, or 100% identical to SEQ ID NO: 29.

Linker

As a product of recombinant DNA technology, fusion proteins have been developed as a class of novel biomolecules with multi-functional properties. By genetically fusing two or more protein domains together, the fusion protein product may obtain many distinct functions derived from each of their component moieties. Besides their wide applications in biological research such as protein purification and imaging, recombinant fusion proteins have also become an important category of biopharmaceuticals. For example, many protein drugs are fused to Fc domains of antibodies, such as Fc-immunoglobulin G1 (Fc-IgG1), or to carrier proteins such as human serum albumin (HSA) or transferrin (Tf) to extend their plasma half-lives and to achieve enhanced therapeutic effects. They have also been widely applied for drug targeting, since proteins such as single chain antibodies or ligands for cell surface receptors can specifically target a linked functional protein (e.g. toxin or cytokine) to a specific type of cells. In drug delivery, the conjugation of protein drugs to carrier moieties such as cell penetrating peptides, antibodies or Tf can achieve efficient transport of the protein drugs across biological barriers such as cell membranes, the blood brain barrier or intestinal epithelium. Several fusion proteins drugs including Enbrel® (tumor necrosis factor/Fc-IgG1), Ontak® (interleukin-2/diphtheria toxin), Orencia® (cytotoxic T-lymphocyte antigen-4/Fc-IgG1), Amevive® (leukocyte function antigen-3/Fc-IgG1), Arcalyst® (interleukin-1 receptor extracellular domain/Fc-IgG1), and Nplate® (thrombopoietin/Fc-IgG1) have been approved by the FDA. With the rapid advancement of biotechnology, it is foreseeable that fusion protein technology will have increasing importance in creating novel protein therapeutics and in improving the performance of current protein drugs.

The successful construction of a recombinant fusion protein often requires two elements: the component proteins and the linkers. The choice of the component proteins is based on the desired functions of the fusion protein product and, in most cases, is relatively straightforward. On the other hand, the selection of a suitable linker to join the protein domains together can be complicated and is often neglected in the design of fusion proteins. Direct fusion of functional domains without a linker may lead to many undesirable outcomes, including misfolding of the fusion proteins, low yield in protein production, or impaired bioactivity. Therefore, the selection or rational design of a linker to join fusion protein domains is an important, yet underexplored, area in recombinant fusion protein technology. Details of linker design, especially the selection between flexible linkers and rigid linkers, can be found, e.g., in Chen, X. et al. "Fusion protein linkers: property, design and functionality." *Advanced Drug Delivery Reviews* 65.10 (2013): 1357-1369, which is incorporated herein by reference in its entirety.

In some embodiments, the fusion proteins or fusion polypeptides described herein includes a linker that connects a first moiety and a second moiety. In some embodiments, the linker is a flexible linker, e.g., a linker with an amino acid sequence that is at least 70%, 75%, 80%, 85%, 90%, 95%, 96%, 97%, 98%, 99%, or 100% identical to SEQ ID NO: 25. In some embodiments, the linker includes an amino acid sequence that is at least 80%, 85%, 90%, 95%, or 100% identical to one or more (e.g., 1, 2, 3, 4, 5, 6, 7, or 8) repeats of GGGGS (SEQ ID NO: 9). In some embodiments, at least 50%, 60%, 70%, 80%, or 90% of the amino acid residues in the flexible linker are glycine residues. In some embodiments, the flexible linker is encoded by a nucleotide sequence that is at least 70%, 75%, 80%, 85%, 90%, 95%, 96%, 97%, 98%, 99%, or 100% identical to SEQ ID NO: 23. In some embodiments, the flexible linker is encoded by a nucleotide sequence that is codon optimized for *E. coli* expression.

In some embodiments, the linker is a rigid linker, e.g., a linker with an amino acid sequence that is at least 70%, 75%, 80%, 85%, 90%, 95%, 96%, 97%, 98%, 99%, or 100% identical to SEQ ID NO: 24. In some embodiments, the rigid linker includes an amino acid sequence that is at least 80%, 85%, 90%, 95%, or 100% identical to one or more (e.g., 1, 2, 3, 4, 5, 6, 7, or 8) repeats of EAAAK (SEQ ID NO: 10).

In some embodiments, at least 30%, 40%, 50%, 60%, 70%, or 80% of the amino acid residues in the rigid linker are alanine residues. In some embodiments, the rigid linker is encoded by a nucleotide sequence that is at least 70%, 75%, 80%, 85%, 90%, 95%, 96%, 97%, 98%, 99%, or 100% identical to SEQ ID NO: 22. In some embodiments, the rigid linker is encoded by a nucleotide sequence that is codon optimized for *E. coli* expression.

In some embodiments, the flexible linker and/or the rigid linker described herein have the same sequence described in Chen, X. et al. "Fusion protein linkers: property, design and functionality." *Advanced Drug Delivery Reviews* 65.10 (2013): 1357-1369.

Redox cofactor

Metabolic engineering studies have generally focused on genetic manipulation (overexpression or disruption) of genes encoding enzymes involved in a particular pathway. However, the flux of a cofactor-dependent pathway is not only controlled by the availability of enzyme, but also controlled by the cofactor and the ratio of the reduced form to the oxidized one of the cofactor. Cofactor manipulations can potentially become a powerful tool for metabolic engineering. Nicotinamide adenine dinucleotide (NADH and $NAD^+$) is one of the most important cofactors, which acts as a cofactor in over 300-oxido-reduction reactions and regulates various enzyme activities and genetic processes. The fluxes of NADH or $NAD^+$-dependent pathways are determined by the availability of NADH (or $NAD^+$), which could be improved by either weakening the metabolic branches competing for NADH (or $NAD^+$), or introducing an NADH (or $NAD^+$) regeneration system. Intracellular NADH or $NAD^+$ can be regenerated in situ by overexpressing an $NAD^+$-dependent formate dehydrogenase (FDH) or an NADH oxidase, respectively. Cofactor engineering approaches have been applied in *Escherichia coli*, *Lactococcus lactis*, and *Saccharomyces cerevisiae*. Details can be found, e.g., in Zhang, Y., et al. "Introduction of an NADH regeneration system into *Klebsiella oxytoca* leads to an enhanced oxidative and reductive metabolism of glycerol." *Metabolic Engineering* 11.2 (2009): 101-106, which is incorporated herein by reference in its entirety.

In some embodiments, a heterogeneous NAD(P)H regeneration system can be expressed in the engineered microbial cell described herein. For example, the microbial cell can express a heterogeneous alcohol dehydrogenases (ADH), glucose oxidase, hydroxy acid dehydrogenases, formate dehydrogenase (FDH), and/or glucose dehydrogenase (GDH). In some embodiments, substrates of these heterogeneous enzymes are supplemented for 7-DHC expression, e.g., isopropanol or glucose.

In some embodiments, the engineered microbial cell described herein expresses an alcohol dehydrogenase (ADH), and isopropanol is supplemented to the culture of the microbial cell for 7-DHC production. In some embodiments, the engineered microbial cell described herein expresses a glucose oxidase, and glucose is supplanted to the culture of the microbial cell for 7-DHC production.

Vectors

Any C7D enzyme and ferredoxin reductase partner that are active in the microbial cell being engineered can be introduced into the cell, typically by introducing and expressing a plasmid encoding the fusion proteins or fusion peptides described herein using standard genetic engineering techniques. The C7D enzyme and ferredoxin reductase partner that are active in the microbial cell being engineered can also be introduced into the cell by genomic integration. For example, a nucleic acid (e.g., any of the nucleic acids encoding the fusion polypeptides described herein) can be knocked into the genome of the cell.

Suitable C7D enzyme and ferredoxin reductase partner can be derived from any source, including plant, archaeal, fungal, gram-positive bacterial, and gram-negative bacterial sources.

One or more copies of any of the plasmids in Table 1 can be introduced into a selected microbial host cell. If more than one type of plasmid is introduced, the plasmids can have the same or different nucleotide sequences. For example, Fusion Variant 1, Fusion Variant 2, Fusion Variant 3, and/or Fusion Variant 4 can be used to co-transform *E. coli* cells. In some embodiments, the fusion proteins or fusion polypeptides are expressed from a strong, constitutive promoter. In some embodiments, the fusion proteins or fusion polypeptides are expressed from an inducible promoter. The sequences encoding the non-native C7D, non-native ferredoxin reductase, fusion proteins or fusion polypeptides can optionally be codon-optimized to enhance expression in the selected microbial host cell (e.g., *E. coli*).

In one aspect, the engineered microbial cell described herein contains a vector that is suitable for expressing the fusion proteins or fusion polypeptides (e.g., any one or combination of the fusion proteins in Table 1) in the host microbial cells. In some embodiments, the vector includes one or more nucleic acid sequences encoding the fusion proteins or fusion polypeptides described herein.

In some embodiments, the vector described herein includes, from 5' end to 3' end: a region including a promoter and/or TIR (e.g., a portion of TIR1 or TIR2, a Shine-Dalgarno sequence, a lac operator, and/or a T7 promoter), a first sequence encoding a C7D enzyme (e.g., any one of the C7D enzymes or a variant thereof described herein), optionally a second sequence encoding any one of the linkers described herein (e.g., a flexible linker or a rigid linker), and a third sequence encoding a ferredoxin reductase (e.g., any one of the ferredoxin reductase partner or a variant thereof described herein). In some embodiments, the first sequence is at least 70%, 75%, 80%, 85%, 90%, 95%, 96%, 97%, 98%, 99%, or 100% identical to SEQ ID NO: 32. In some embodiments, the second sequence is at least 70%, 75%, 80%, 85%, 90%, 95%, 96%, 97%, 98%, 99%, or 100% identical to SEQ ID NO: 22 or 23. In some embodiments, the third sequence is at least 70%, 75%, 80%, 85%, 90%, 95%, 96%, 97%, 98%, 99%, or 100% identical to SEQ ID NO: 33.

In some embodiments, the vector described herein includes all or a portion of TIR1 or TIR2. Typically, the translational initiation region (TIR) sequence includes part of the upstream (Shine-Dalgarno/RBS sequence) and part of the gene coding sequence. In some embodiments, the TIR1 sequence is set forth in SEQ ID NO: 13. In some embodiments, the TIR2 sequence is set forth in SEQ ID NO: 14. Details of the TIR can be found, e.g., in Shilling, P. J., et al. "Improved designs for pET expression plasmids increase protein production yield in *Escherichia coli*." *Communications Biology* 3.1 (2020): 214, which is incorporated herein by reference in its entirety.

In some embodiments, there is a sequence encoding a HIS-tag (e.g., SEQ ID NO: 11) downstream of the first sequence. In some embodiments, there is a sequence encoding a HIS-tag (SEQ ID NO: 12) upstream of the third sequence. In some embodiments, the HIS-tag described herein comprises or consists of an amino acid sequence that is at least 80%, 85%, 90%, 95%, or 100% identical to SEQ ID NO: 11, 12, or 35.

In some embodiments, the sequence encoding the fusion protein or fusion polypeptide described herein is cloned to a pShilling plasmid. Details of the pShilling vector can be found, e.g., in Shilling, P. J., et al. "Improved designs for pET expression plasmids increase protein production yield in *Escherichia coli*." *Communications Biology* 3.1 (2020): 214, which is incorporated herein by reference in its entirety.

In some embodiments, the vector described herein includes, from 5' end to 3' end, a first sequence encoding *Caenorhabditis elegans* C7D (e.g., SEQ ID NO: 4), a second sequence encoding a flexible linker (e.g., SEQ ID NO: 25), and a third sequence encoding a *Mycobacterium tuberculosis* KshB (e.g., SEQ ID NO: 7). In some embodiments, the vector includes a sequence that is at least 70%, 75%, 80%, 85%, 90%, 95%, 96%, 97%, 98%, 99%, or 100% identical to SEQ ID NO: 19. In some embodiments, the vector encodes a fusion polypeptide that has an amino acid sequence that is at least 70%, 75%, 80%, 85%, 90%, 95%, 96%, 97%, 98%, 99%, or 100% identical to SEQ ID NO: 15.

In some embodiments, the vector described herein includes, from 5' end to 3' end, a first sequence encoding *Caenorhabditis elegans* C7D (e.g., SEQ ID NO: 4), a second sequence encoding a rigid linker (e.g., SEQ ID NO: 24), and a third sequence encoding a *Mycobacterium tuberculosis* KshB (e.g., SEQ ID NO: 7). In some embodiments, the vector includes a sequence that is at least 70%, 75%, 80%, 85%, 90%, 95%, 96%, 97%, 98%, 99%, or 100% identical to SEQ ID NO: 20. In some embodiments, the vector encodes a fusion polypeptide that has an amino acid sequence that is at least 70%, 75%, 80%, 85%, 90%, 95%, 96%, 97%, 98%, 99%, or 100% identical to SEQ ID NO: 16.

In some embodiments, the vector described herein includes, from 5' end to 3' end, a first sequence encoding *Caenorhabditis elegans* C7D (e.g., SEQ ID NO: 4), a second sequence encoding a C-terminal HIS-tag (e.g., SEQ ID NO: 11), a third sequence encoding a flexible linker (e.g., SEQ ID NO: 25), a fourth sequence encoding an N-terminal HIS-tag (e.g., SEQ ID NO: 12), and a fifth sequence encoding a *Mycobacterium tuberculosis* KshB (e.g., SEQ ID NO: 7). In some embodiments, the vector includes a sequence that is at least 70%, 75%, 80%, 85%, 90%, 95%, 96%, 97%, 98%, 99%, or 100% identical to SEQ ID NO: 34. In some embodiments, the vector encodes a fusion polypeptide that has an amino acid sequence that is at least 70%, 75%, 80%, 85%, 90%, 95%, 96%, 97%, 98%, 99%, or 100% identical to SEQ ID NO: 17.

In some embodiments, the vector described herein includes, from 5' end to 3' end, a first sequence encoding *Caenorhabditis elegans* C7D (e.g., SEQ ID NO: 4), a second sequence encoding a C-terminal HIS-tag (e.g., SEQ ID NO: 11), a third sequence encoding a rigid linker (e.g., SEQ ID NO: 24), a fourth sequence encoding an N-terminal HIS-tag (e.g., SEQ ID NO: 12), and a fifth sequence encoding a *Mycobacterium tuberculosis* KshB (e.g., SEQ ID NO: 7). In some embodiments, the vector includes a sequence that is at least 70%, 75%, 80%, 85%, 90%, 95%, 96%, 97%, 98%, 99%, or 100% identical to SEQ ID NO: 21. In some embodiments, the vector encodes a fusion polypeptide that has an amino acid sequence that is at least 70%, 75%, 80%, 85%, 90%, 95%, 96%, 97%, 98%, 99%, or 100% identical to SEQ ID NO: 18.

Microbial Host Cells

Any microbe that can be used to express introduced genes can be engineered for fermentative production of 7-DHC as described above. In certain embodiments, the microbe is one that is naturally incapable of fermentative production of 7-DHC. In some embodiments, the microbe is one that is readily cultured, for example, a microbe known to be useful as a host cell in fermentative production of compounds of interest. Bacteria cells, including gram-positive or gram-negative bacteria can be engineered as described above. Examples include, in addition to *C. glutamicum* cells, *Bacillus subtilus*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, *B. thuringiensis*, *S. albus*, *S. lividans*, *S. coelicolor*, *S. griseus*, *Pseudomonas* sp. (e.g. *Pseudomonas putida*), *P. alcaligenes*, *P. citrea*, *Lactobacillus* spp. (e.g., *L. lactis*, *L. plantarum*), *L. grayi*, *E. coli*, *E. faecium*, *E. gallinarum*, *E. casseliflavus*, and/or *E. faecalis* cells.

In some embodiments, the microbe or microbial cell described herein is a *E. coli* strain. In some embodiments, the microbe or microbial cell described herein is an engineered *E. coli* strain for expressing toxic membrane proteins. In some embodiments, the engineered *E. coli* strain have a background of JM109 (DE3), W3110 (DE3), BL21 (DE3), C41 (DE3), and/or C43 (DE3). Details of the engineered *E. coli* strains can be found, e.g., Miroux B. and Walker J. E. "Over-production of proteins in *Escherichia coli*: mutant hosts that allow synthesis of some membrane proteins and globular proteins at high levels." *Journal of Molecular Biology* 260.3 (1996): 289-298, which is incorporated herein by reference in its entirety.

There are numerous types of anaerobic cells that can be used as microbial host cells in the methods described herein. In some embodiments, the microbial cells are obligate anaerobic cells. Obligate anaerobes typically do not grow well, if at all, in conditions where oxygen is present. It is to be understood that a small amount of oxygen may be present, that is, there is some level of tolerance level that obligate anaerobes have for a low level of oxygen. Obligate anaerobes engineered as described above can be grown under substantially oxygen-free conditions, wherein the amount of oxygen present is not harmful to the growth, maintenance, and/or fermentation of the anaerobes.

Alternatively, the microbial host cells used in the methods described herein can be facultative anaerobic cells. Facultative anaerobes can generate cellular ATP by aerobic respiration (e.g., utilization of the TCA cycle) if oxygen is present. However, facultative anaerobes can also grow in the absence of oxygen. Facultative anaerobes engineered as described above can be grown under substantially oxygen-free conditions, wherein the amount of oxygen present is not harmful to the growth, maintenance, and/or fermentation of the anaerobes, or can be alternatively grown in the presence of greater amounts of oxygen.

In some embodiments, the microbial host cells used in the methods described herein are filamentous fungal cells. (See, e.g., Berka & Barnett, Biotechnology Advances, (1989), 7(2):127-154). Examples include *Trichoderma longibrachiatum*, *T. viride*, *T. koningii*, *T. harzianum*, *Penicillium* sp., *Humicola insolens*, *H. lanuginose*, *H. grisea*, *Chrysosporium* sp., *C. lucknowense*, *Gliocladium* sp., *Aspergillus* sp. (e.g., *A. oryzae*, *A. niger*, *A. sojae*, *A. japonicus*, *A. nidulans*, or *A. awamori*), *Fusarium* sp. (e.g., *F. roseum*, *F. graminum*, *F. cerealis*, *F. oxysporuim*, or *F. venenatum*), *Neurospora* sp. (e.g., *N. crassa* or *Hypocrea* sp.), *Mucor* sp. (e.g., *M. miehei*), *Rhizopus* sp., and *Emericella* sp. cells. In particular embodiments, the fungal cell engineered as described above is *A. nidulans*, *A. awamori*, *A. oryzae*, *A. aculeatus*, *A. niger*, *A. japonicus*, *T. reesei*, *T. viride*, *F. oxysporum*, or *F. solani*. Illustrative plasmids or plasmid components for use with such hosts include those described in U.S. Patent Pub. No. 2011/0045563.

Yeasts can also be used as the microbial host cell in the methods described herein. Examples include: *Saccharomyces* sp., *Schizosaccharomyces* sp., *Pichia* sp., *Hansenula polymorpha*, *Pichia stipites*, *Kluyveromyces marxianus*, *Kluyveromyces* spp., *Yarrowia lipolytica* and *Candida* sp. In some embodiments, the *Saccharomyces* sp. is *S. cerevisiae* (See, e.g., Romanos et al., Yeast, (1992), 8(6):423-488). Illustrative plasmids or plasmid components for use with such hosts include those described in U.S. Pat. No. 7,659,097 and U.S. Patent Pub. No. 2011/0045563.

In some embodiments, the host cell can be an algal cell derived, e.g., from a green alga, red alga, a glaucophyte, a chlorarachniophyte, a euglenid, a chromista, or a dinoflagellate. (See, e.g., Saunders & Warmbrodt, "Gene Expression in Algae and Fungi, Including Yeast," (1993), National Agricultural Library, Beltsville, Md.). Illustrative plasmids or plasmid components for use in algal cells include those described in U.S. Patent Pub. No. 2011/0045563.

In other embodiments, the host cell is a cyanobacterium, such as cyanobacterium classified into any of the following groups based on morphology: Chlorococcales, Pleurocapsales, Oscillatoriales, Nostocales, Synechosystic or Stigonematales (See, e.g., Lindberg et al., Metab. Eng., (2010) 12(1):70-79). Illustrative plasmids or plasmid components for use in cyanobacterial cells include those described in U.S. Patent Pub. Nos. 2010/0297749 and 2009/0282545 and in Intl. Patent Pub. No. WO 2011/034863.

In other embodiments, the host cell may include other prokaryotic and eukaryotic organisms not limited to bacteria or yeasts. Exemplary species include *Escherichia coli*, *Saccharomyces cerevisiae*, *Saccharomyces kluyveri*, *Candida boidinii*, *Clostridium kluyveri*, *Clostridium acetobutylicum*, *Clostridium beijerinckii*, *Clostridium saccharoperbutylacetonicum*, *Clostridium perfringens*, *Clostridium difficile*, *Clostridium botulinum*, *Clostridium tyrobutyricum*, *Clostridium tetanomorphum*, *Clostridium tetani*, *Clostridium propionicum*, *Clostridium aminobutyricum*, *Clostridium subterminale*, *Clostridium sticklandii*, *Ralstonia eutropha*, *Mycobacterium bovis*, *Mycobacterium tuberculosis*, *Porphyromonas gingivalis*, *Arabidopsis thaliana*, *Thermus thermophilus*, *Pseudomonas* species, including *Pseudomonas aeruginosa*, *Pseudomonas putida*, *Pseudomonas stutzeri*, *Pseudomonas fluorescens*, *Homo sapiens*, *Oryctolagus cuniculus*, *Rhodobacter spaeroides*, *Thermoanaerobacter brockii*, *Metallosphaera sedula*, *Leuconostoc mesenteroides*, *Chloroflexus aurantiacus*, *Roseiflexus castenholzii*, *Erythrobacter*, *Simmondsia chinensis*, *Acinetobacter* species, including *Acinetobacter calcoaceticus* and *Acinetobacter baylyi*, *Porphyromonas gingivalis*, *Sulfolobus tokodaii*, *Sulfolobus solfataricus*, *Sulfolobus acidocaldarius*, *Bacillus subtilis*, *Bacillus cereus*, *Bacillus megaterium*, *Bacillus brevis*, *Bacillus pumilus*, *Rattus norvegicus*, *Klebsiella pneumonia*, *Klebsiella oxytoca*, *Euglena gracilis*, *Treponema denticola*, *Moorella thermoacetica*, *Thermotoga maritima*, *Halobacterium salinarum*, *Geobacillus stearothermophilus*, *Aeropyrum pernix*, *Sus scrofa*, *Caenorhabditis elegans*, *Corynebacterium glutamicum*, *Acidaminococcus fermentans*, *Lactococcus lactis*, *Lactobacillus plantarum*, *Streptococcus thermophilus*, *Enterobacter aerogenes*, *Candida*, *Aspergillus terreus*, *Pedicoccus pentosaceus*, *Zymomonas mobilus*, *Acetobacter pasteurians*, *Kluyveromyces lactis*, *Eubacterium barkeri*, *Bacteroides capillosus*, *Anaerotruncus colihominis*, *Natranaerobius thermophilusm*, *Campylobacter jejuni*, *Haemophilus influenzae*, *Serratia marcescens*, *Citrobacter amalonaticus*, *Myxococcus xanthus*, *Fusobacterium nuleatum*, *Penicillium chrysogenum*, *Nocardia iowensis*, *Nocardia farcinica*, *Streptomyces griseus*, *Schizosaccharomyces pombe*, *Geobacillus thermoglucosidasius*, *Salmonella typhimurium*, *Vibrio chol-* era, *Heliobacter pylori, Nicotiana tabacum, Oryza sativa, Haloferax mediterranei, Agrobacterium tumefaciens, Achromobacter denitrificans, Fusobacterium nucleatum, Streptomyces clavuligenus, Acinetobacter baumanii, Mus musculus, Lachancea kluyveri, Trichomonas vaginalis, Trypanosoma brucei, Pseudomonas stutzeri, Bradyrhizobium japonicum, Mesorhizobium loti, Bos taurus, Nicotiana glutinosa, Vibrio vulnificus, Selenomonas ruminantium, Vibrio parahaemolyticus, Archaeoglobus fulgidus, Haloarcula marismortui, Pyrobaculum aerophilum, Mycobacterium smegmatis* MC2 155, *Mycobacterium avium* subsp. paratuberculosis K-10, *Mycobacterium marinum* M, *Tsukamurella paurometabola* DSM 20162, *Cyanobium* PCC7001, *Dictyostelium discoideum* AX4.

In certain embodiments, suitable organisms include *Acinetobacter baumannii* Naval-82, *Acinetobacter* sp. ADP1, *Acinetobacter* sp. strain M-1, *Actinobacillus succinogenes* 130Z, *Allochromatium vinosum* DSM 180, *Amycolatopsis methanolica, Arabidopsis thaliana, Atopobium parvulum* DSM 20469, *Azotobacter vinelandii* DJ, *Bacillus alcalophilus* ATCC 27647, *Bacillus azotoformans* LMG 9581, *Bacillus coagulans* 36D1, *Bacillus megaterium, Bacillus methanolicus* MGA3, *Bacillus methanolicus* PB1, *Bacillus methanolicus* PB-1, *Bacillus selenitireducens* MLS10, *Bacillus smithii, Bacillus subtilis, Burkholderia cenocepacia, Burkholderia cepacia, Burkholderia multivorans, Burkholderia pyrrocinia, Burkholderia stabilis, Burkholderia thailandensis* E264, *Burkholderiales bacterium* Joshi_001, *Campylobacter jejuni, Candida albicans, Candida boidinii, Candida methylica, Carboxydothermus hydrogenoformans, Carboxydothermus hydrogenoformans* Z-2901, *Caulobacter* sp. APO7, *Chloroflexus aggregans* DSM 9485, *Chloroflexus aurantiacus* J-10-fl, *Citrobacter freundii, Citrobacter koseri* ATCC BAA-895, *Citrobacter youngae, Clostridium, Clostridium acetobutylicum, Clostridium acetobutylicum* ATCC 824, *Clostridium acidurici, Clostridium aminobutyricum, Clostridium asparagiforme* DSM 15981, *Clostridium beijerinckii, Clostridium beijerinckii* NCIMB 8052, *Clostridium bolteae* ATCC BAA-613, *Clostridium carboxidivorans* P7, *Clostridium cellulovorans* 743B, *Clostridium difficile, Clostridium hiranonis* DSM 13275, *Clostridium hylemonae* DSM 15053, *Clostridium kluyveri, Clostridium kluyveri* DSM 555, *Clostridium ljungdahli, Clostridium ljungdahlii* DSM 13528, *Clostridium methylpentosum* DSM 5476, *Clostridium pasteurianum, Clostridium pasteurianum* DSM 525, *Clostridium perfringens, Clostridium perfringens* ATCC 13124, *Clostridium perfringens* str. 13, *Clostridium phytofermentans* ISDg, *Clostridium saccharobutylicum, Clostridium saccharoperbutylacetonicum, Clostridium saccharoperbutylacetonicum* N1-4, *Clostridium tetani, Corynebacterium glutamicum* ATCC 14067, *Corynebacterium glutamicum* R, *Corynebacterium* sp. U-96, *Corynebacterium variabile, Cupriavidus necator* N-1, *Cyanobium* PCC7001, *Desulfatibacillum alkenivorans* AK-01, *Desulfitobacterium hafniense, Desulfitobacterium metallireducens* DSM 15288, *Desulfotomaculum reducens* MI-1, *Desulfovibrio africanus* str. Walvis Bay, *Desulfovibrio fructosovorans* JJ, *Desulfovibrio vulgaris* str. Hildenborough, *Desulfovibrio vulgaris* str. 'Miyazaki F', *Dictyostelium discoideum* AX4, *Escherichia coli, Escherichia coli* K-12, *Escherichia coli* K-12 MG1655, *Eubacterium hallii* DSM 3353, *Flavobacterium frigoris, Fusobacterium nucleatum* subsp. *polymorphum* ATCC 10953, *Geobacillus* sp. Y4.1MC1, *Geobacillus thermodenitrificans* NG80-2, *Geobacter bemidjiensis* Bem, *Geobacter sulfurreducens, Geobacter sulfurreducens* PCA, *Geobacillus stearothermophilus* DSM 2334, *Haemophilus influenzae, Helicobacter pylori, Homo sapiens, Hydrogenobacter thermophilus, Hydrogenobacter thermophilus* TK-6, *Hyphomicrobiwn denitrificans* ATCC 51888, *Hyphomicrobium zavarzinii, Klebsiella pneumoniae, Klebsiella pneumoniae* subsp. *pneumoniae* MGH 78578, *Lactobacillus brevis* ATCC 367, *Leuconostoc mesenteroides, Lysinibacillus fusiformis, Lysinibacillus sphaericus, Mesorhizobiurn loti* MAFF303099, *Metallosphaera sedula, Methanosarcina acetivorans, Methanosarcina acetivorans* C2A, *Methanosarcina barkeri, Methanosarcina mazei* Tuc01, *Methylobacter marinus, Methylobacterium extorquens, Methylobacterium extorquens* AM1, *Methylococcus capsulatas, Methylomonas aminofaciens, Moorella thermoacetica, Mycobacter* sp. strain JC1 DSM 3803, *Mycobacterium avium* subsp. *paratuberculosis* K-10, *Mycobacterium bovis* BCG, *Mycobacterium gastri, Mycobacterium marinum* M, *Mycobacterium smegmatis, Mycobacterium smegmatis* MC2 155, *Mycobacterium tuberculosis, Nitrosopumilus solaria* BD31, *Nitrososphaera gargensis* Ga9.2, *Nocardia farcinica* IFM 10152, *Nocardia iowensis* (sp. NRRL 5646), *Nostoc* sp. PCC 7120, *Ogataea angusta, Ogataea parapolymorpha* DL-1 (*Hansenula polymorpha* DL-1), *Paenibacillus peoriae* KCTC 3763, *Paracoccus denitrificans, Penicillium chrysogenum, Photobacterium profundum* 3TCK, *Phytofermentans* ISDg, *Pichia pastoris, Picrophilus torridus* DSM9790, *Porphyromonas gingivalis, Porphyromonas gingivalis* W83, *Pseudomonas aeruginosa* PA01, *Pseudomonas denitrificans, Pseudomonas knackmussii, Pseudomonas putida, Pseudomonas* sp, *Pseudomonas syringae* pv. *syringae* B728a, *Pyrobaculum islandicum* DSM 4184, *Pyrococcus abyssi, Pyrococcus furiosus, Pyrococcus horikoshii* OT3, *Ralstonia eutropha, Ralstonia eutropha* H16, *Rhodobacter capsulatus, Rhodobacter sphaeroides, Rhodobacter sphaeroides* ATCC 17025, *Rhodopseudomonas palustris, Rhodopseudomonas palustris* CGA009, *Rhodopseudomonas palustris* DX-1, *Rhodospirillum rubrum, Rhodospirillum rubrum* ATCC 11170, *Ruminococcus obeum* ATCC 29174, *Saccharomyces cerevisiae, Saccharomyces cerevisiae* S288c, *Salmonella enterica, Salmonella enterica* subsp. *enterica* serovar *Typhimurium* str. LT2, *Salmonella enterica typhimurium, Salmonella typhimurium, Schizosaccharomyces pombe, Sebaldella termitidis* ATCC 33386, *Shewanella oneidensis* MR-1, *Sinorhizobium meliloti* 1021, *Streptomyces coelicolor, Streptomyces griseus* subsp. *griseus* NBRC 13350, *Sulfolobus acidocalarius, Sulfolobus solfataricus* P-2, *Synechocystis* str. PCC 6803, *Syntrophobacter fumaroxidans, Thauera aromatica, Thermoanaerobacter* sp. X514, *Thermococcus kodakaraensis, Thermococcus litoralis, Thermoplasma acidophilum, Thermoproteus neutrophilus, Thermotoga maritima, Thiocapsa roseopersicina, Tolumonas auensis* DSM 9187, *Trichomonas vaginalis* G3, *Trypanosoma brucei, Tsukamurella paurometabola* DSM 20162, *Vibrio cholera, Vibrio harveyi* ATCC BAA-1116, *Xanthobacter autotrophicus* Py2, *Yersinia intermedia*, or *Zea mays*.

Genetic Engineering Methods

Microbial cells can be engineered for fermentative 7-DHC production using conventional techniques of molecular biology (including recombinant techniques), microbiology, cell biology, and biochemistry, which are within the skill of the art. Such techniques are explained fully in the literature, see e.g., "Molecular Cloning: A Laboratory Manual," fourth edition (Sambrook et al., 2012); "Oligonucleotide Synthesis" (M. J. Gait, ed., 1984); "Culture of Animal Cells: A Manual of Basic Technique and Specialized Applications" (R. I. Freshney, ed., 6th Edition, 2010); "Methods in Enzymology" (Academic Press, Inc.); "Current Protocols in Molecular Biology" (F. M. Ausubel et al., eds., 1987, and periodic updates); "PCR: The Polymerase Chain Reaction," (Mullis et al., eds., 1994); Singleton et al., Dictionary of Microbiology and Molecular Biology 2nd ed., J. Wiley & Sons (New York, N.Y. 1994).

Vectors are polynucleotide vehicles used to introduce genetic material into a cell. Vectors useful in the methods described herein can be linear or circular. Vectors can integrate into a target genome of a host cell or replicate independently in a host cell. For many applications, integrating vectors that produced stable transformants are preferred. Vectors can include, for example, an origin of replication, a multiple cloning site (MCS), and/or a selectable marker. An expression vector typically includes an expression cassette containing regulatory elements that facilitate expression of a polynucleotide sequence (often a coding sequence) in a particular host cell. Vectors include, but are not limited to, integrating vectors, prokaryotic plasmids, episomes, viral vectors, cosmids, and artificial chromosomes.

Illustrative regulatory elements that may be used in expression cassettes include promoters, enhancers, internal ribosomal entry sites (IRES), and other expression control elements (e.g., transcription termination signals, such as polyadenylation signals and poly-U sequences). Such regulatory elements are described, for example, in Goeddel, Gene Expression Technology: Methods In Enzymology 185, Academic Press, San Diego, Calif. (1990).

In some embodiments, vectors may be used to introduce systems that can carry out genome editing, such as CRISPR systems. See U.S. Patent Pub. No. 2014/0068797, published 6 Mar. 2014; see also Jinek M., et al., "A programmable dual-RNA-guided DNA endonuclease in adaptive bacterial immunity," Science 337:816-21, 2012). In Type II CRISPR-Cas9 systems, Cas9 is a site-directed endonuclease, namely an enzyme that is, or can be, directed to cleave a polynucleotide at a particular target sequence using two distinct endonuclease domains (HNH and RuvC/RNase H-like domains). Cas9 can be engineered to cleave DNA at any desired site because Cas9 is directed to its cleavage site by RNA. Cas9 is therefore also described as an "RNA-guided nuclease." More specifically, Cas9 becomes associated with one or more RNA molecules, which guide Cas9 to a specific polynucleotide target based on hybridization of at least a portion of the RNA molecule(s) to a specific sequence in the target polynucleotide. Ran, F. A., et al., ("In vivo genome editing using *Staphylococcus aureus* Cas9," Nature 520 (7546):186-91, 2015, Apr. 9; including all extended data) present the crRNA/tracrRNA sequences and secondary structures of eight Type II CRISPR-Cas9 systems. Cas9-like synthetic proteins are also known in the art (see U.S. Published Patent Application No. 2014-0315985, published 23 Oct. 2014).

Vectors or other polynucleotides can be introduced into microbial cells by any of a variety of standard methods, such as transformation, conjugation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. Transformants can be selected by any method known in the art. Suitable methods for selecting transformants are described in U.S. Patent Pub. Nos. 2009/0203102, 2010/0048964, and 2010/0003716, and International Publication Nos. WO 2009/076676, WO 2010/003007, and WO 2009/132220.

Engineered Microbial Cells

The above-described methods can be used to produce engineered microbial cells that produce, and in certain embodiments, overproduce, 7-DHC.

In some embodiments, an engineered microbial cell expresses a fusion protein or fusion polypeptide that include at least two heterologous sequences encoding, e.g., a non-native C7D enzymes and a non-native ferredoxin reductase. In various embodiments, the microbial cell can include and express, for example: (1) a single type of fusion protein or fusion polypeptide, or (2) two or more types of fusion proteins or fusion polypeptides described herein.

This engineered host cell can include at least one additional genetic alteration that increases flux through any pathway leading to the production of an immediate precursor of 7-DHC. For example, this can be accomplished by: increasing the activity of upstream enzymes, and/or reducing consumption of 7-DHC precursors.

The engineered microbial cells can contain introduced genes that have a native nucleotide sequence or that differ from native. For example, the native nucleotide sequence can be codon-optimized for expression in a particular host cell. Codon optimization for a particular host can, for example, be based on the codon usage tables found at www.kazusa.or.jp/codon/. The amino acid sequences encoded by any of these introduced genes can be native or can differ from native. In various embodiments, the amino acid sequences have at least 60 percent, 70 percent, 75 percent, 80 percent, 85 percent, 90 percent, 95 percent or 100 percent amino acid sequence identity with a native amino acid sequence.

In some embodiments, the engineered microbial cell described herein expresses a fusion protein or fusion polypeptide that includes a non-native C7D enzyme (e.g., any one of the C7D enzymes described herein), and a non-native ferredoxin reductase (e.g., any one of the non-native ferredoxin reductase described herein). In some embodiments, the fusion protein or fusion polypeptide described herein can increase the production of 7-DHC by at least 10, 20, 30, 40, 50, 60, 70, 80, or 90 percent or by at least 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, or 1000-fold, as compared to the combination of the non-native C7D enzyme and non-native ferredoxin reductase.

In some embodiments, the fusion protein or fusion polypeptide described herein can increase the production of 7-DHC by at least 10, 20, 30, 40, 50, 60, 70, 80, or 90 percent or by at least 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, or 1000-fold, as compared to a native C7D and/or a native ferredoxin reductase.

In some embodiments, expressing the fusion protein or fusion polypeptide described herein can increase the production of 7-DHC by at least 10, 20, 30, 40, 50, 60, 70, 80, or 90 percent or by at least 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 150-fold, 200-fold, 250-fold, 300-fold, 350-fold, 400-fold, 450-fold, 500-fold, 550-fold, 600-fold, 650-fold, 700-fold, 750-fold, 800-fold, 850-fold, 900-fold, 950-fold, or 1000-fold, as compared to expressing each protein or a variant thereof individually from the same vector.

In various embodiments, the increase in 7-DHC titer is in the range of 1-fold to 2-fold, 2-fold to 3-fold, 3-fold to 4-fold, 4-fold to 5-fold, 5-fold to 6-fold, 6-fold to 7-fold, 7-fold to 8-fold, 8-fold to 9-fold, 9-fold to 10-fold, 10-fold to 20-fold, 20-fold to 50-fold, 50-fold to 100-fold, 100-fold to 200-fold, 200-fold to 500-fold, 500-fold to 1000-fold, 1000-fold to 2000-fold, 2000-fold to 5000-fold, 5000-fold to 10000-fold, or any range bounded by any of the values listed above. These increases are determined relative to the 7-DHC titer observed in a 7-DHC-producing microbial cell that does not include the modification (e.g., transformation) discussed herein. This reference cell may (but need not) have other modifications aimed at increasing 7-DHC production.

In some embodiments, the fusion protein or fusion polypeptide described herein, when expressed in a microbial cell (e.g., *E. coli*), can produce greater than 100 mg/L, greater than 200 mg/L, greater than 300 mg/L, greater than 400 mg/L, greater than 500 mg/L, greater than 600 mg/L, or greater than 700 mg/L 7-DHC, from about 800 mg/L starting cholesterol.

Any of the approaches for increasing 7-DHC production described herein can be combined, in any combination, to achieve even higher 7-DHC production levels.

Culturing of Engineered Microbial Cells

Any of the microbial cells described herein can be cultured, e.g., for maintenance, growth, and/or 7-DHC production. In some embodiments, the microbial cells described herein (e.g., bacteria) are cultured to an optical density at 600 nm of 1-100, e.g., an optical density of 1-50, 5-50, 10-50, 20-50, 30-50, or 40-50.

In various embodiments, the cultures include produced 7-DHC at titers of at least 10, 20, 30, 40, 50, 60, 70, 80, 90, 100, 200, 300, 400, 500, 600, 700, 800, 900, or 1000 mg/L. In various embodiments, the titer is in the range of 10 mg/L to 1000 mg/L, 50 mg/L to 1000 mg/L, 100 mg/L to 1000 mg/L, 200 mg/L to 1000 mg/L, 300 mg/L to 1000 mg/L, 400 mg/L to 1000 mg/L, 500 mg/L to 1000 mg/L, 600 mg/L to 1000 mg/L, 700 mg/L to 1000 mg/L, 800 mg/L to 1000 mg/L, 10 mg/L to 800 mg/L, 50 mg/L to 800 mg/L, 100 mg/L to 800 mg/L, 200 mg/L to 800 mg/L, 300 mg/L to 800 mg/L, 400 mg/L to 800 mg/L, 500 mg/L to 800 mg/L, 600 mg/L to 800 mg/L, 700 mg/L to 800 mg/L, 10 mg/L to 600 mg/L, 50 mg/L to 600 mg/L, 100 mg/L to 600 mg/L, 200 mg/L to 600 mg/L, 300 mg/L to 600 mg/L, 400 mg/L to 600 mg/L, 500 mg/L to 600 mg/L, or any range bounded by any of the values listed above.

Culture Media

Microbial cells can be cultured in any suitable medium including, but not limited to, a minimal medium, i.e., one containing the minimum nutrients possible for cell growth. Minimal medium typically contains: (1) a carbon source for microbial growth; (2) salts, which may depend on the particular microbial cell and growing conditions; and (3) water. Suitable media can also include any combination of the following: a nitrogen source for growth and product formation, a sulfur source for growth, a phosphate source for growth, metal salts for growth, vitamins for growth, and other cofactors for growth.

Any suitable carbon source can be used to cultivate the host cells. The term "carbon source" refers to one or more carbon-containing compounds capable of being metabolized by a microbial cell. In various embodiments, the carbon source is a carbohydrate (such as a monosaccharide, a disaccharide, an oligosaccharide, or a polysaccharide), or an invert sugar (e.g., enzymatically treated sucrose syrup). Illustrative monosaccharides include glucose (dextrose), fructose (levulose), and galactose; illustrative oligosaccharides include dextran or glucan, and illustrative polysaccharides include starch and cellulose. Suitable sugars include C6 sugars (e.g., fructose, mannose, galactose, or glucose) and C5 sugars (e.g., xylose or arabinose). Other, less expensive carbon sources include sugar cane juice, beet juice, sorghum juice, and the like, any of which may, but need not be, fully or partially deionized.

The salts in a culture medium generally provide essential elements, such as magnesium, nitrogen, phosphorus, and sulfur to allow the cells to synthesize proteins and nucleic acids.

Minimal medium can be supplemented with one or more selective agents, such as antibiotics.

To produce 7-DHC, the culture medium can include, and/or is supplemented during culture with, glucose and/or a nitrogen source such as urea, an ammonium salt, ammonia, or any combination thereof. In some embodiments, the culture medium can include isopropanol.

Culture Conditions

Materials and methods suitable for the maintenance and growth of microbial cells are well known in the art. See, for example, U.S. Pub. Nos. 2009/0203102, 2010/0003716, and 2010/0048964, and International Pub. Nos. WO 2004/033646, WO 2009/076676, WO 2009/132220, and WO 2010/003007, Manual of Methods for General Bacteriology Gerhardt et al., eds), American Society for Microbiology, Washington, D.C. (1994) or Brock in Biotechnology: A Textbook of Industrial Microbiology, Second Edition (1989) Sinauer Associates, Inc., Sunderland, Mass.

In some embodiments, the engineered microbial cells (e.g., transformed *E. coli* cells expressing the fusion protein or fusion polypeptide described herein) are expressed at a temperature of about 10-20° C. (e.g., about 13° C., about 14° C., about 15° C., about 16° C., about 17° C., about 18° C., about 19° C., or about 20° C.) for about 1-24 hours, about 1-20 hours, about 1-16 hours, about 1-12 hours, about 1-8 hours, about 1-4 hours, about 4-24 hours, about 4-20 hours, about 4-16 hours, about 4-12 hours, about 4-8 hours, about 8-24 hours, about 8-20 hours, about 8-16 hours, about 8-12 hours, about 12-24 hours, about 12-18 hours, about 12-16 hours, about 16-24 hours, about 16-20 hours, or about 20-24 hours.

In some embodiments, the engineered microbial cells (e.g., transformed *E. coli* cells) are induced by IPTG to induce expression of the fusion protein or fusion polypeptide described herein. In some embodiments, the IPTG concentration is about 0.05 mM, about 0.06 mM, about 0.07 mM, about 0.08 mM, about 0.09 mM, about 0.1 mM, about 0.15 mM, about 0.2 mM, about 0.25 mM, about 0.3 mM, about 0.35 mM, about 0.4 mM, about 0.45 mM, about 0.5 mM, about 0.55 mM, about 0.6 mM, about 0.65 mM, about 0.7 mM, about 0.75 mM, about 0.8 mM, about 0.85 mM, about 0.9 mM, about 0.95 mM, or about 0.1 mM. In some embodiments, the IPTG concentration is about 0.05-1 mM, about 0.05-0.5 mM, about 0.1-1 mM, or about 0.1-0.5 mM.

Cells can be grown under aerobic, anoxic, or anaerobic conditions based on the requirements of the particular cell.

In some embodiments, the culture of engineered microbial cells (transformed E. coli cells expressing the fusion protein or fusion polypeptide described herein) is supplemented with polymyxin B. In some embodiments, the concentration of polymyxin B in the culture is at least 8 mg/L, at least 16 mg/L, at least 32 mg/L, at least 64 mg/L, at least 64 mg/L, at least 80 mg/L, at least 96 mg/L, at least 112 mg/L, at least 128 mg/L, at least 144 mg/L, at least 160 mg/L, at least 176 mg/L, or at least 192 mg/L. In some embodiments, the concentration of polymyxin B in the culture is about 32-192 mg/L, about 64-192 mg/L, about 96-192 mg/L, about 128-192 mg/L, about 160-192 mg/L, about 32-160 mg/L, about 64-160 mg/L, about 96-160 mg/L, about 128-160 mg/L, about 32-128 mg/L, about 64-128 mg/L, about 96-128 mg/L, about 32-96 mg/L, or about 32-64 mg/L.

In some embodiments, the cell density for 1× cell loading described herein (e.g., in FIG. 6) is not directly measured but determined by measuring $OD_{600}$ value of the culture (e.g., in rich media). For instance, the 1× cell loading described herein has a $OD_{600}$ value of about 10-20 (e.g., about 10, about 11, about 12, about 13, about 14, about 15, about 16, about 17, about 18, about 19, or about 20).

Standard culture conditions and modes of fermentation, such as batch, fed-batch, or continuous fermentation that can be used are described in U.S. Publ. Nos. 2009/0203102, 2010/0003716, and 2010/0048964, and International Pub. Nos. WO 2009/076676, WO 2009/132220, and WO 2010/003007. Batch and Fed-Batch fermentations are common and well known in the art, and examples can be found in Brock, Biotechnology: A Textbook of Industrial Microbiology, Second Edition (1989) Sinauer Associates, Inc.

7-DHC Production and Recovery

Any of the methods described herein may further include a step of recovering 7-DHC. In some embodiments, the produced 7-DHC contained in a so-called harvest stream is recovered/harvested from the production vessel. The harvest stream may include, for instance, cell-free or cell-containing aqueous solution coming from the production vessel, which contains 7-DHC as a result of the conversion of production substrate by the resting cells in the production vessel. Cells still present in the harvest stream may be separated from the 7-DHC by any operations known in the art, such as for instance filtration, centrifugation, decantation, membrane crossflow ultrafiltration or microfiltration, tangential flow ultrafiltration or microfiltration or dead-end filtration. After this cell separation operation, the harvest stream is essentially free of cells.

Further steps of separation and/or purification of the produced 7-DHC from other components contained in the harvest stream, i.e., so-called downstream processing steps may optionally be carried out. These steps may include any means known to a skilled person, such as, for instance, concentration, extraction, crystallization, precipitation, adsorption, ion exchange, and/or chromatography. Any of these procedures can be used alone or in combination to purify 7-DHC. Further purification steps can include one or more of, e.g., concentration, crystallization, precipitation, washing and drying, treatment with activated carbon, ion exchange, nanofiltration, and/or re-crystallization. The design of a suitable purification protocol may depend on the cells, the culture medium, the size of the culture, the production vessel, etc. and is within the level of skill in the art.

EXAMPLES

The invention is further described in the following examples, which do not limit the scope of the invention described in the claims.

Example 1. Initial Screening of C7D-KshB Fusion Proteins

A C. elegans gene encoding cholesterol 7-desaturase (C7D; UniProt ID: Q17938; SEQ ID NO: 1) was codon optimized for E. coli expression. Various potential ferredoxin reductases were tested. A Mycobacterium tuberculosis gene encoding KshB (UniProt ID: P9WJ93; SEQ ID NO: 7) was also codon optimized for E. coli expression. The codon optimized genes for C7D and KshB are shown in SEQ ID NO: 32 and SEQ ID NO: 33, respectively. A flexible poly glycine-serine linker (SEQ ID NO: 25) or a rigid linker (SEQ ID NO: 24) was used to connect C7D and KshB.

E. coli cells were transformed with plasmids encoding C7D, KshB, or fusion proteins of cholesterol 7-desaturase and ferredoxin reductase (C7D-KshB), as shown in the table below and FIG. 2. For example, E. coli cells were transformed with expression plasmid pShilling_TIR2_CeC7D_KshB 1.0 to generate Strain No. 38 below. The plasmids have an IPTG-inducible backbone, and also contain kanamycin antibiotic resistance gene, a lacI repressor gene, a T7 promoter, and a high copy ColE1 origin of replication.

TABLE 1

| Strain No. | Expression Plasmids | Modification |
|---|---|---|
| 28 | C7D_CAEEL_Ec_IDT1 and KshB (not fused) separated by RBS | Separated C7D and KshB Variant 1 |
| 29 | C7D_CAEEL_Ec_IDT1[C-terminal HIS-tag] and KshB (not fused) separated by RBS | Separated C7D and KshB Variant 2 |
| 30 | pET28a_C7D_CAEEL_Ec_IDT_1 | No KshB (control) |
| 31 | pET28a-C7D_CAEEL_Ec_IDT_1_Chis | No KshB (control) |
| 32 | pShilling_TIR1_C7D_CAEEL_Ec_IDT_1_KshB_MYCTU_Ec_IDT_2 | Separated C7D and KshB Variant 3 |
| 33 | pShilling_TIR2_C7D_CAEEL_Ec_IDT_1_KshB_MYCTU_Ec_IDT_2 | Separated C7D and KshB Variant 4 |
| 34 | pshilling_TIR1_C7D_CAEEL_Ec_IDT_1_Chis_KshB_MYCTU_Ec_IDT_2_Nhis | Separated C7D and KshB Variant 5 |

TABLE 1-continued

| Strain No. | Expression Plasmids | Modification |
|---|---|---|
| 35 | pshilling_TIR2_C7D_CAEEL_Ec_IDT_1_Chis_KshB_MYCTU_Ec_IDT_2_Nhis | Separated C7D and KshB Variant 6 |
| 36 | pShilling_TIR2_KshB_MYCTU_Ec_IDT_2_C7D_CAEEL_Ec_IDT_1_Rvr | Separated KshB and C7D Variant 7 |
| 37 | pShilling_TIR2_KshB_MYCTU_Ec_IDT_2_Nhis_C7D_CAEEL_Ec_IDT_1_Chis_Rvr | Separated KshB and C7D Variant 8 |
| 38 | pShilling_TIR2_CeC7D_KshB 1.0 | Fusion Variant 1 (flexible linker) |
| 39 | pShilling_TIR2_C7D_CAEEL_Ec_IDT_1_rgl_KshB_MYCTU_Ec_IDT_2 | Fusion Variant 2 (rigid linker) |
| 40 | pShilling_TIR2_C7D_CAEEL_Ec_IDT_1_Chis_fxl_KshB_MYCTU_Ec_IDT_2_Nhis | Fusion Variant 3 (flexible linker) |
| 41 | pShilling_TIR2_C7D_CAEEL_Ec_IDT_1_Chis_rgl_KshB_MYCTU_Ec_IDT_2_Nhis | Fusion Variant 4 (rigid linker) |

Note:
RBS: ribosome-binding site

Sequences of the linkers used in the fusion proteins are summarized in the table below.

TABLE 2

| Linker | DNA Sequence | Amino Acid (AA) Sequence |
|---|---|---|
| Rigid (rgl) | GCTGAGGCTGCAGCCAAAGAAGCGG CGGCTAAGGCG (SEQ ID NO: 22) | AEAAAKEAAAKA (SEQ ID NO: 24) |
| Flexible (fxl) | GGAGGCGGTGGGTCAGGAGGTGGTG GATCTGGCGGAGGTGGTAGT (SEQ ID NO: 23) | GGGGSGGGGSGGGGS (SEQ ID NO: 25) |

Specifically, Fusion Variant 1 (SEQ ID NO: 15) includes from N-terminus to C-terminus: a modified C7D polypeptide (SEQ ID NO: 4), a flexible linker (SEQ ID NO: 25), and a wild-type KshB polypeptide (SEQ ID NO: 7); Fusion Variant 2 (SEQ ID NO: 16) includes from N-terminus to C-terminus: a modified C7D polypeptide (SEQ ID NO: 4), a rigid linker (SEQ ID NO: 24), and a wild-type KshB polypeptide (SEQ ID NO: 7); Fusion Variant 3 (SEQ ID NO: 17) includes from N-terminus to C-terminus: a modified C7D polypeptide with a C-terminal HIS-tag (SEQ ID NO: 6), a flexible linker (SEQ ID NO: 25), and a wild-type KshB polypeptide (SEQ ID NO: 7); and Fusion Variant 4 (SEQ ID NO: 18) includes from N-terminus to C-terminus: a modified C7D polypeptide with a C-terminal HIS-tag (SEQ ID NO: 6), a rigid linker (SEQ ID NO: 24), and a wild-type KshB polypeptide (SEQ ID NO: 7). The amino acid sequences of C7D, KshB, and fusion variants are shown in FIG. 7.

As shown in FIG. 8, the nucleotide sequences encoding Fusion Variant 1, Fusion Variant 2, Fusion Variant 3, and Fusion Variant 4 are listed as SEQ ID NO: 19, SEQ ID NO: 20, SEQ ID NO: 34, and SEQ ID NO: 21, respectively.

Figure 3:
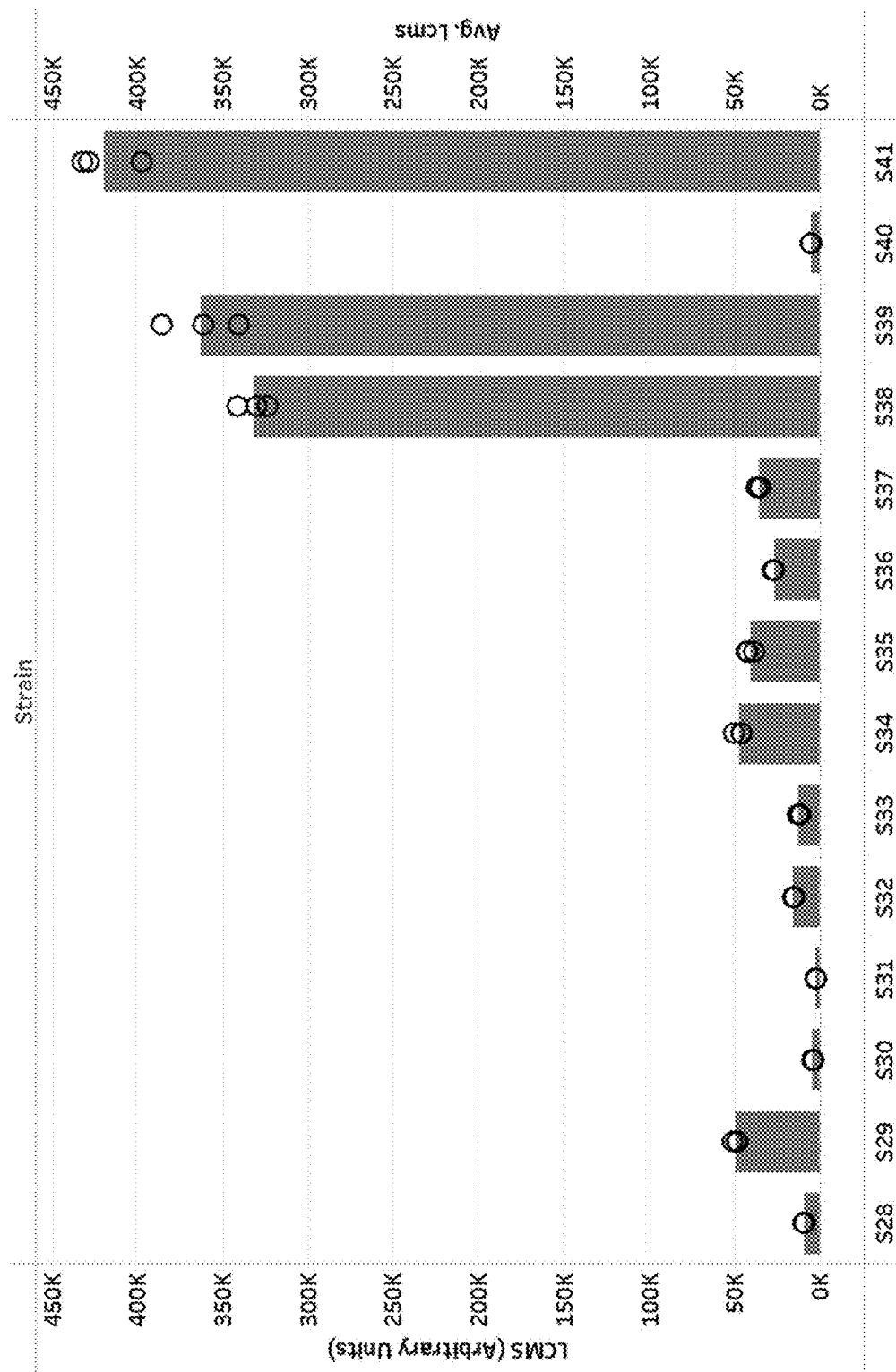
FIG. 3 shows the 7-DHC production level of the transformed E. coli strains listed in Table 1. The level of 7-DHC was determined by liquid chromatography/mass spectrometry (LC/MS). Y-axis represents arbitrary units of 7-DHC determined by LC/MS.

The initial screening results of the E. coli strains for converting cholesterol to 7-DHC are shown in FIG. 3. Both flexible and rigid linkers were tested. The activity of the fusion proteins was tested in vivo when the cells were not lysed. The results demonstrated that Fusion Variant 1 (strain No. 38), Fusion Variant 2 (strain No. 39), and Fusion Variant 4 (strain No. 41) led to improved activity for 7-DHC production. It is contemplated that either the flexible linker (e.g., in Fusion Variant 1) or the rigid linker (e.g., in Fusion Variant 2 and Fusion Variant 4) contributed to the improved activity, possibly due to an optimal conformation of the C7D-KshB complex having a more efficient electron shuttling system. However, Fusion Variant 3 did not exhibit an improved activity. It is possible that the C-terminal HIS tag of C7D is not compatible with the flexible linker to orient the C7D-KshB complex with a high electron shuttling efficiency.

Figure 4:
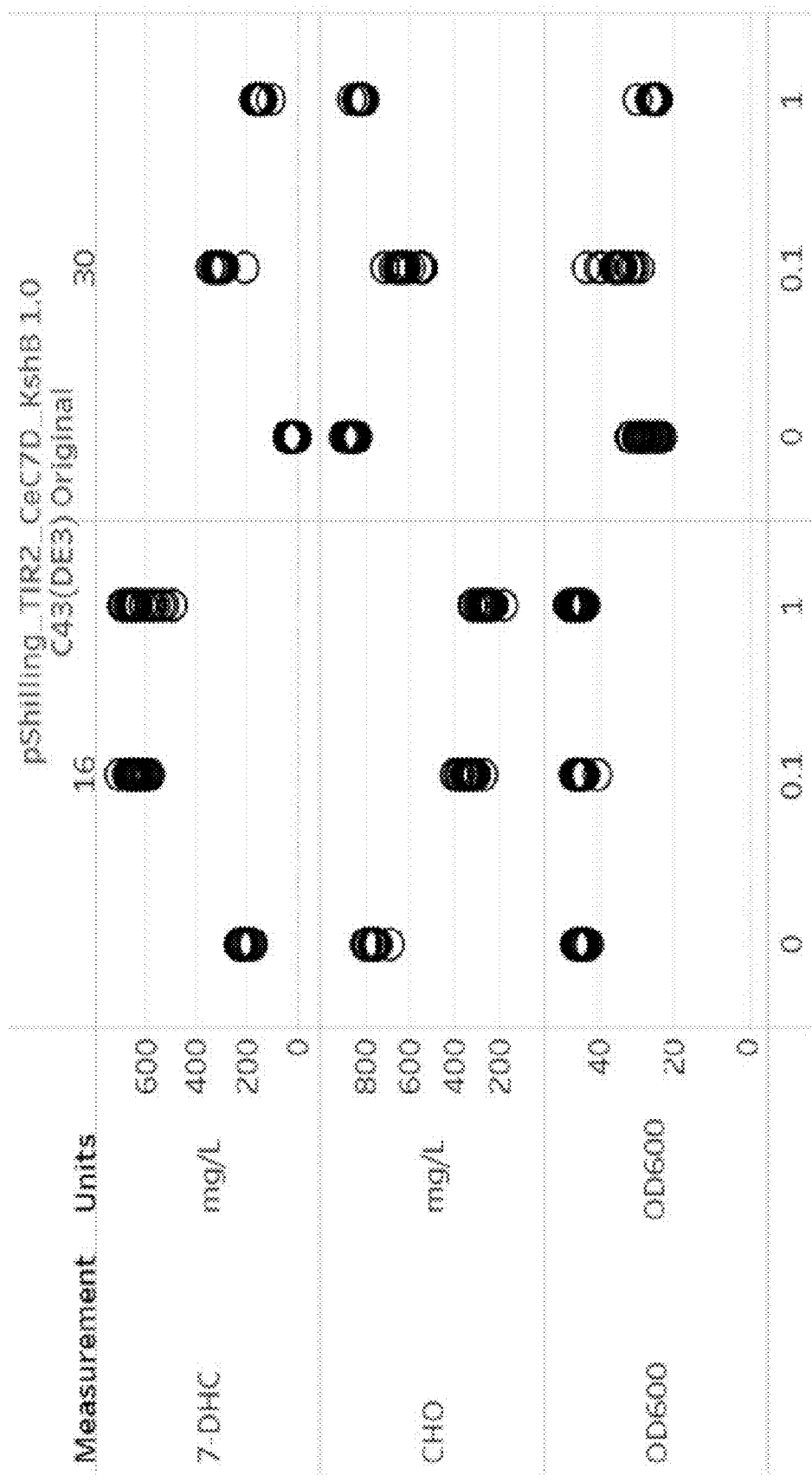
FIG. 4 is a graph of in vivo conversion of cholesterol to 7-DHC using C43 (DE3) host E. coli cells expressing pShilling_TIR2_CeC7D_KshB 1.0 (Strain No. 38). 7-DHC production was induced at two different temperatures (16° C. and 30° C.). The concentration of IPTG (isopropyl (3-D-1-thiogalactopyranoside) was also varied between 0, 0.1, and 1 mM. CHO stands for cholesterol.

As shown in FIG. 4, over 700 mg/L of 7-DHC can be produced from about 800 mg/L cholesterol using E. coli strains expressing the fusion proteins.

Example 2. Expressing Fusion Proteins in Various E. coli Strains

The C7D-KshB fusion proteins were expressed in multiple E. coli strains of different backgrounds, including JM109 (DE3), W3110 (DE3), BL21 (DE3), C41 (DE3), and C43 (DE3) strains. C41 (DE3) and C43 (DE3) strains (referred in literatures as Walker strains because these strains were identified by Miroux B. and Walker J. E. "Overproduction of proteins in Escherichia coli: mutant hosts that allow synthesis of some membrane proteins and globular proteins at high levels." Journal of Molecular Biology 260.3 (1996): 289-298) have genomic mutations that enable better expression of toxic membrane proteins, e.g., those that are difficult to express in wild-type E. coli strains. Results showed that in vivo activity was highest in the E. coli strain with C43 (DE3) background.

Figure 5:
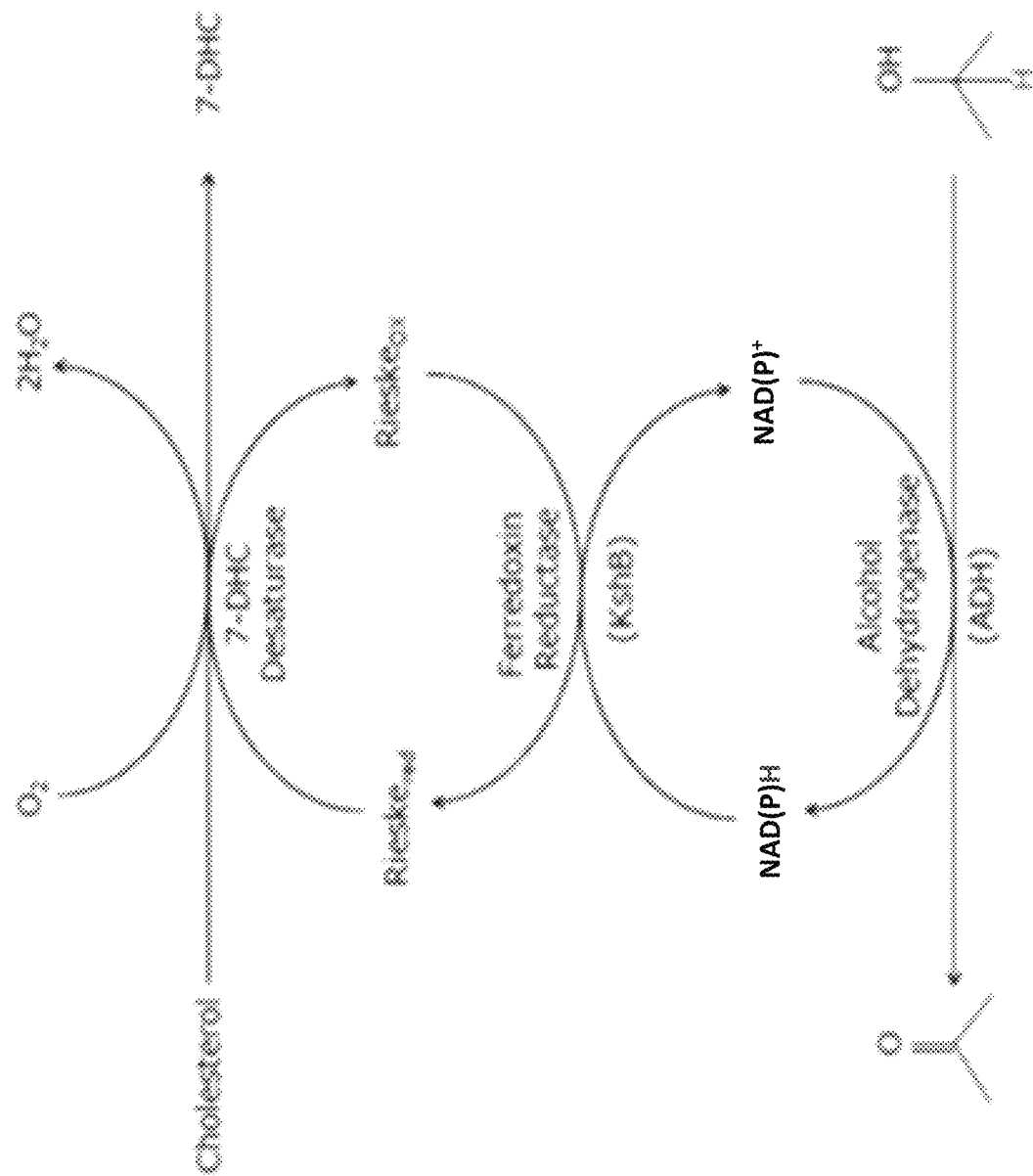
FIG. 5 is a schematic showing electron transfer reactions involved in 7-DHC production. Electrons transfer from isopropanol to acetone by alcohol dehydrogenase, then from $NAD(P)^+$ to NAD(P)H, then from NAD(P)H to cholesterol 7-desaturase, and ultimately to oxidize cholesterol to 7-DHC.

Example 3. Oxidation of Cholesterol can be Facilitated by Oxidation of an Additional Chemical The oxidation of cholesterol to produce 7-DHC requires an electron source, e.g., NAD(P)H. As shown in FIG. 5, the ferredoxin reductase (KshB) can oxidize NAD(P)H to form $NAD(P)^+$, and reduce Rieske from an oxidized state (Rieske$_{ox}$) to a reduced state (Rieske$_{red}$). Meanwhile, cholesterol 7-desaturase (or 7-DHC desaturase, C7D) can oxidize Rieske$_{red}$ and cholesterol to generate Rieske$_{ox}$ and 7-DHC, respectively, and reduce $O_2$ to form $H_2O$. The overall reaction is summarized as follows:

$$\text{cholesterol} + H^+ + NAD(P)H + O_2 = 7\text{-DHC} + 2H_2O + NAD(P)^+$$

Further, the electron source NAD(P)H can be generated from NAD(P)$^+$ when coupled with an oxidation reaction of isopropanol, catalyzed by alcohol dehydrogenase (ADH). Alternatively, reduction of NAD(P)$^+$ can be coupled with oxidization of glucose to form gluconate using glucose oxidase.

Figure 6:
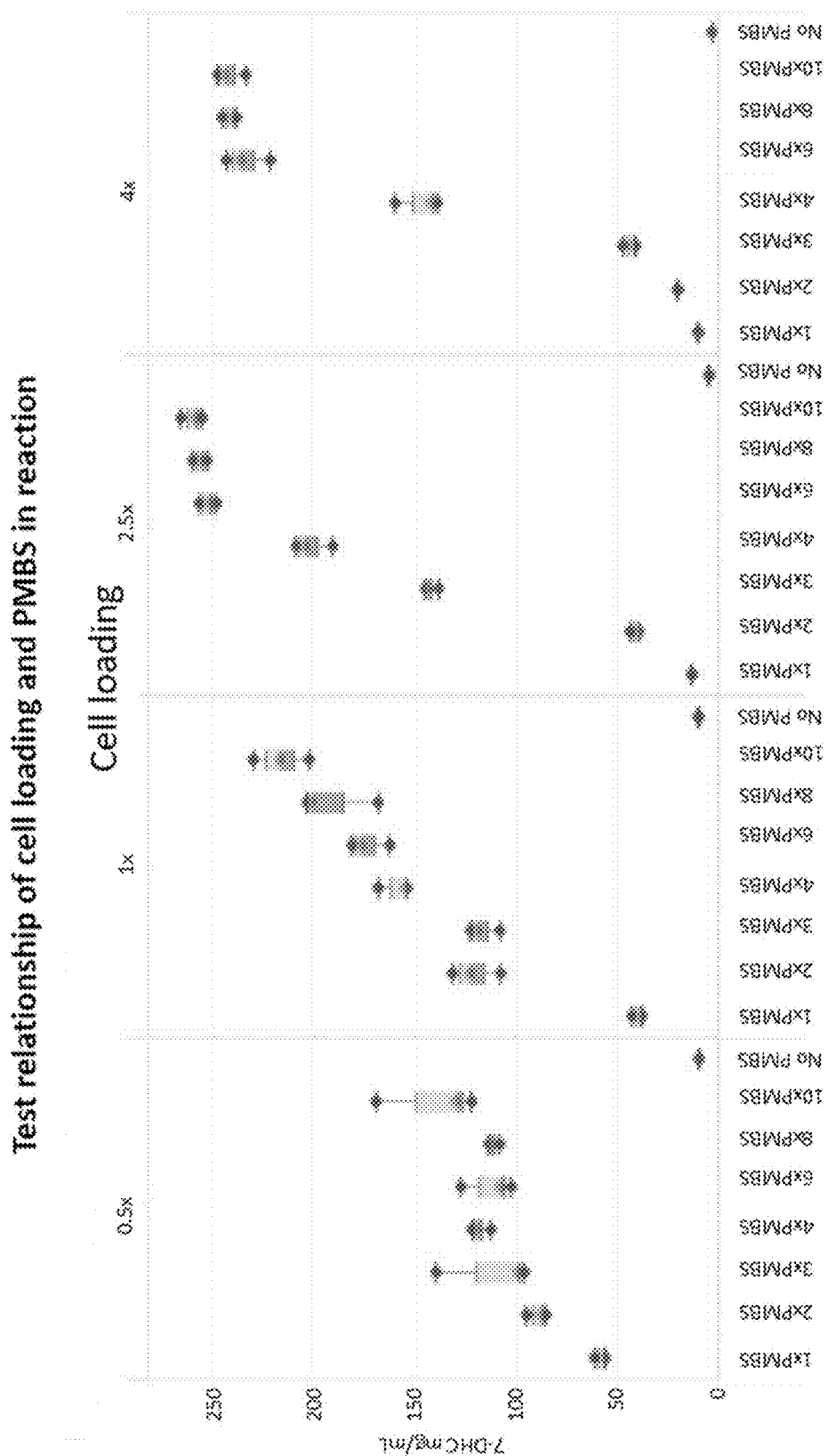
FIG. 6 is a graph showing the effect of PMBS and cell loading to the in vivo reaction system to generate 7-DHC. Y-axis represents 7-DHC concentration (mg/L). HPβ-cyclodextrin was added to all conditions. Cell loading stands for the amount of pelleted cells that were resuspended in the reaction mixture.

Example 4. Addition of PMBS Significantly Improves In Vivo Conversion to 7-DHC Polymyxin B (PMBS) was added to the in vivo reaction system at various cell loading amounts. 1×PMBS corresponds to 32 mg/L final concentration. As shown in FIG. 6, when no PMBS was added, 7-DHC production was not observed. Addition of PMBS improved 7-DHC production. However, no further improvement was observed when more than 6×PMBS was added.

It is contemplated that the function of PMBS was to permeabilize the *E. coli* cell membrane to facilitate transport of cholesterol to the C7D-KshB fusion protein.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

SEQUENCE LISTING

```
Sequence total quantity: 35
SEQ ID NO: 1             moltype = AA  length = 428
FEATURE                  Location/Qualifiers
source                   1..428
                         mol_type = protein
                         organism = Caenorhabditis elegans
SEQUENCE: 1
MLLEQIWGFL TAHPISVVTT ILIVYLIHIT LKPLNRVRRL GDVGLFFGKP ELKGFYRERQ  60
LERLKLLRRV GDMPPVFPNG WYCVCESEKL ANNQIMEITV LGQFLSLIRS ESGAVYITDS 120
YCPHIGANFN IGGRVVRDNC IQCPFHGWIF SAETGKCVEV PYDEGRIPEQ AKVTTWPCIE 180
RNNNIYLWYH CDGAEPEWEI PEITEITDGF WHLGGRTEHE VMCHIQEIPE NGADIAHLNY 240
LHKSAPPVTK GSDIIKTDLS DPQPAVQHVW DGKWEVKSEE DRHCGVMHLN QFMTFWGYKV 300
PLTSSKLVAE QHGPGIVHML FDFGIWGKGV VFQTVTPEEA LLQRVRFRIF SNIPWFFVKF 360
FMTVEAMQFE RDVFIWSNKK YIKSPLLVKN DGPIQKHRRW FSQFYTENSP KMLKDGSLSN 420
QAKSIFDW                                                         428

SEQ ID NO: 2             moltype = AA  length = 439
FEATURE                  Location/Qualifiers
source                   1..439
                         mol_type = protein
                         organism = synthetic construct
SEQUENCE: 2
MLLEQIWGFL TAHPISVVTT ILIVYLIHIT LKPLNRVRRL GDVGLFFGKP ELKGFYRERQ  60
LERLKLLRRV GDMPPVFPNG WYCVCESEKL ANNQIMEITV LGQFLSLIRS ESGAVYITDS 120
YCPHIGANFN IGGRVVRDNC IQCPFHGWIF SAETGKCVEV PYDEGRIPEQ AKVTTWPCIE 180
RNNNIYLWYH CDGAEPEWEI PEITEITDGF WHLGGRTEHE VMCHIQEIPE NGADIAHLNY 240
LHKSAPPVTK GSDIIKTDLS DPQPAVQHVW DGKWEVKSEE DRHCGVMHLN QFMTFWGYKV 300
PLTSSKLVAE QHGPGIVHML FDFGIWGKGV VFQTVTPEEA LLQRVRFRIF SNIPWFFVKF 360
FMTVEAMQFE RDVFIWSNKK YIKSPLLVKN DGPIQKHRRW FSQFYTENSP KMLKDGSLSN 420
QAKSIFDWAA ALEHHHHHH                                             439

SEQ ID NO: 3             moltype = AA  length = 430
FEATURE                  Location/Qualifiers
source                   1..430
                         mol_type = protein
                         organism = synthetic construct
SEQUENCE: 3
MGSLLEQIWG FLTAHPISVV TTILIVYLIH ITLKPLNRVR RLGDVGLFFG KPELKGFYRE  60
RQLERLKLLR RVGDMPPVFP NGWYCVCESE KLANNQIMEI TVLGQFLSLI RSESGAVYIT 120
DSYCPHIGAN FNIGGRVVRD NCIQCPFHGW IFSAETGKCV EVPYDEGRIP EQAKVTTWPC 180
IERNNNIYLW YHCDGAEPEW EIPEITEITD GFWHLGGRTE HEVMCHIQEI PENGADIAHL 240
NYLHKSAPPV TKGSDIIKTD LSDPQPAVQH VWDGKWEVKS EEDRHCGVMH LNQFMTFWGY 300
KVPLTSSKLV AEQHGPGIVH MLFDFGIWGK GVVFQTVTPE EALLQRVRFR IFSNIPWFFV 360
KFFMTVEAMQ FERDVFIWSN KKYIKSPLLV KNDGPIQKHR RWFSQFYTEN SPKMLKDGSL 420
SNQAKSIFDW                                                       430

SEQ ID NO: 4             moltype = AA  length = 430
FEATURE                  Location/Qualifiers
source                   1..430
                         mol_type = protein
                         organism = synthetic construct
SEQUENCE: 4
MQLLLEQIWG FLTAHPISVV TTILIVYLIH ITLKPLNRVR RLGDVGLFFG KPELKGFYRE  60
```

```
RQLERLKLLR RVGDMPPVFP NGWYCVCESE KLANNQIMEI TVLGQFLSLI RSESGAVYIT    120
DSYCPHIGAN FNIGGRVVRD NCIQCPFHGW IFSAETGKCV EVPYDEGRIP EQAKVTTWPC    180
IERNNNIYLW YHCDGAEPEW EIPEITEITD GFWHLGGRTE HEVMCHIQEI PENGADIAHL    240
NYLHKSAPPV TKGSDIIKTD LSDPQPAVQH VWDGKWEVKS EEDRHCGVMH LNQFMTFWGY    300
KVPLTSSKLV AEQHGPGIVH MLFDFGIWGK GVVFQTVTPE EALLQRVRFR IFSNIPWFFV    360
KFFMTVEAMQ FERDVFIWSN KKYIKSPLLV KNDGPIQKHR RWFSQFYTEN SPKMLKDGSL    420
SNQAKSIFDW                                                           430

SEQ ID NO: 5              moltype = AA   length = 441
FEATURE                   Location/Qualifiers
source                    1..441
                          mol_type = protein
                          organism = synthetic construct
SEQUENCE: 5
MGSLLEQIWG FLTAHPISVV TTILIVYLIH ITLKPLNRVR RLGDVGLFFG KPELKGFYRE    60
RQLERLKLLR RVGDMPPVFP NGWYCVCESE KLANNQIMEI TVLGQFLSLI RSESGAVYIT    120
DSYCPHIGAN FNIGGRVVRD NCIQCPFHGW IFSAETGKCV EVPYDEGRIP EQAKVTTWPC    180
IERNNNIYLW YHCDGAEPEW EIPEITEITD GFWHLGGRTE HEVMCHIQEI PENGADIAHL    240
NYLHKSAPPV TKGSDIIKTD LSDPQPAVQH VWDGKWEVKS EEDRHCGVMH LNQFMTFWGY    300
KVPLTSSKLV AEQHGPGIVH MLFDFGIWGK GVVFQTVTPE EALLQRVRFR IFSNIPWFFV    360
KFFMTVEAMQ FERDVFIWSN KKYIKSPLLV KNDGPIQKHR RWFSQFYTEN SPKMLKDGSL    420
SNQAKSIFDW AAALEHHHHH H                                              441

SEQ ID NO: 6              moltype = AA   length = 441
FEATURE                   Location/Qualifiers
source                    1..441
                          mol_type = protein
                          organism = synthetic construct
SEQUENCE: 6
MQLLLEQIWG FLTAHPISVV TTILIVYLIH ITLKPLNRVR RLGDVGLFFG KPELKGFYRE    60
RQLERLKLLR RVGDMPPVFP NGWYCVCESE KLANNQIMEI TVLGQFLSLI RSESGAVYIT    120
DSYCPHIGAN FNIGGRVVRD NCIQCPFHGW IFSAETGKCV EVPYDEGRIP EQAKVTTWPC    180
IERNNNIYLW YHCDGAEPEW EIPEITEITD GFWHLGGRTE HEVMCHIQEI PENGADIAHL    240
NYLHKSAPPV TKGSDIIKTD LSDPQPAVQH VWDGKWEVKS EEDRHCGVMH LNQFMTFWGY    300
KVPLTSSKLV AEQHGPGIVH MLFDFGIWGK GVVFQTVTPE EALLQRVRFR IFSNIPWFFV    360
KFFMTVEAMQ FERDVFIWSN KKYIKSPLLV KNDGPIQKHR RWFSQFYTEN SPKMLKDGSL    420
SNQAKSIFDW AAALEHHHHH H                                              441

SEQ ID NO: 7              moltype = AA   length = 358
FEATURE                   Location/Qualifiers
source                    1..358
                          mol_type = protein
                          organism = Mycobacterium tuberculosis
SEQUENCE: 7
MTEAIGDEPL GDHVLELQIA EVVDETDEAR SLVFAVPDGS DDPEIPPRRL RYAPGQFLTL    60
RVPSERTGSV ARCYSLCSSP YTDDALAVTV KRTADGYASN WLCDHAQVGM RIHVLAPSGN    120
FVPTTLDADF LLLAAGSGIT PIMSICKSAL AEGGGQVTLL YANRDDRSVI FGDALRELAA    180
KYPDRLTVLH WLESLQGLPS ASALAKLVAP YTDRPVFICG PGPFMQAARD ALAALKVPAQ    240
QVHIEVFKSL ESDPFAAVKV DDSGDEAPAT AVVELDGQTH TVSWPRTAKL LDVLLAAGLD    300
APFSCREGHC GACACTLRAG KVNMGVNDVL EQQDLDEGLI LACQSRPESD SVEVTYDE     358

SEQ ID NO: 8              moltype = AA   length = 360
FEATURE                   Location/Qualifiers
source                    1..360
                          mol_type = protein
                          organism = synthetic construct
SEQUENCE: 8
MQLTEAIGDE PLGDHVLELQ IAEVVDETDE ARSLVFAVPD GSDDPEIPPR RLRYAPGQFL    60
TLRVPSERTG SVARCYSLCS SPYTDDALAV TVKRTADGYA SNWLCDHAQV GMRIHVLAPS    120
GNFVPTTLDA DFLLLAAGSG ITPIMSICKS ALAEGGGQVT LLYANRDDRS VIFGDALREL    180
AAKYPDRLTV LHWLESLQGL PSASALAKLV APYTDRPVFI CGPGPFMQAA RDALAALKVP    240
AQQVHIEVFK SLESDPFAAV KVDDSGDEAP ATAVVELDGQ THTVSWPRTA KLLDVLLAAG    300
LDAPFSCREG HCGACACTLR AGKVNMGVND VLEQQDLDEG LILACQSRPE SDSVEVTYDE    360

SEQ ID NO: 9              moltype = AA   length = 5
FEATURE                   Location/Qualifiers
source                    1..5
                          mol_type = protein
                          organism = synthetic construct
SEQUENCE: 9
GGGGS                                                                5

SEQ ID NO: 10             moltype = AA   length = 5
FEATURE                   Location/Qualifiers
source                    1..5
                          mol_type = protein
                          organism = synthetic construct
SEQUENCE: 10
EAAAK                                                                5
```

```
SEQ ID NO: 11              moltype = AA  length = 11
FEATURE                    Location/Qualifiers
source                     1..11
                           mol_type = protein
                           organism = synthetic construct
SEQUENCE: 11
AAALEHHHHH H                                                          11

SEQ ID NO: 12              moltype = AA  length = 16
FEATURE                    Location/Qualifiers
source                     1..16
                           mol_type = protein
                           organism = synthetic construct
SEQUENCE: 12
HHHHHHSSGL VPRGSH                                                     16

SEQ ID NO: 13              moltype = DNA  length = 15
FEATURE                    Location/Qualifiers
source                     1..15
                           mol_type = other DNA
                           organism = synthetic construct
SEQUENCE: 13
gttatcatgg gtagc                                                      15

SEQ ID NO: 14              moltype = DNA  length = 15
FEATURE                    Location/Qualifiers
source                     1..15
                           mol_type = other DNA
                           organism = synthetic construct
SEQUENCE: 14
gcagctatgc agctt                                                      15

SEQ ID NO: 15              moltype = AA  length = 803
FEATURE                    Location/Qualifiers
source                     1..803
                           mol_type = protein
                           organism = synthetic construct
SEQUENCE: 15
MQLLLEQIWG FLTAHPISVV TTILIVYLIH ITLKPLNRVR RLGDVGLFFG KPELKGFYRE      60
RQLERLKLLR RVGDMPPVFP NGWYCVCESE KLANNQIMEI TVLGQFLSLI RSESGAVYIT     120
DSYCPHIGAN FNIGGRVVRD NCIQCPFHGW IFSAETGKCV EVPYDEGRIP EQAKVTTWPC     180
IERNNNIYLW YHCDGAEPEW EIPEITEITD GFWHLGGRTE HEVMCHIQEI PENGADIAHL     240
NYLHKSAPPV TKGSDIIKTD LSDPQPAVQH VWDGKWEVKS EEDRHCGVMH LNQFMTFWGY     300
KVPLTSSKLV AEQHGPGIVH MLFDFGIWGK GVVFQTVTPE EALLQRVRFR IFSNIPWFFV     360
KFFMTVEAMQ FERDVFIWSN KKYIKSPLLV KNDGPIQKHR RWFSQFYTEN SPKMLKDGSL     420
SNQAKSIFDW GGGGSGGGGS GGGGSMTEAI GDEPLGDHVL ELQIAEVVDE TDEARSLVFA     480
VPDGSDDPEI PPRRLRYAPG QFLTLRVPSE RTGSVARCYS LCSSPYTDDA LAVTVKRTAD     540
GYASNWLCDH AQVGMRIHVL APSGNFVPTT LDADFLLLAA GSGITPIMSI CKSALAEGGG     600
QVTLLYANRD DRSVIFGDAL RELAAKYPDR LTVLHWLESL QGLPSASALA KLVAPYTDRP     660
VFICGPGPFM QAARDALAAL KVPAQQVHIE VFKSLESDPF AAVKVDDSGD EAPATAVVEL     720
DGQTHTVSWP RTAKLLDVLL AAGLDAPFSC REGHCGACAC TLRAGKVNMG VNDVLEQQDL     780
DEGLILACQS RPESDSVEVT YDE                                            803

SEQ ID NO: 16              moltype = AA  length = 800
FEATURE                    Location/Qualifiers
source                     1..800
                           mol_type = protein
                           organism = synthetic construct
SEQUENCE: 16
MQLLLEQIWG FLTAHPISVV TTILIVYLIH ITLKPLNRVR RLGDVGLFFG KPELKGFYRE      60
RQLERLKLLR RVGDMPPVFP NGWYCVCESE KLANNQIMEI TVLGQFLSLI RSESGAVYIT     120
DSYCPHIGAN FNIGGRVVRD NCIQCPFHGW IFSAETGKCV EVPYDEGRIP EQAKVTTWPC     180
IERNNNIYLW YHCDGAEPEW EIPEITEITD GFWHLGGRTE HEVMCHIQEI PENGADIAHL     240
NYLHKSAPPV TKGSDIIKTD LSDPQPAVQH VWDGKWEVKS EEDRHCGVMH LNQFMTFWGY     300
KVPLTSSKLV AEQHGPGIVH MLFDFGIWGK GVVFQTVTPE EALLQRVRFR IFSNIPWFFV     360
KFFMTVEAMQ FERDVFIWSN KKYIKSPLLV KNDGPIQKHR RWFSQFYTEN SPKMLKDGSL     420
SNQAKSIFDW AEAAAKEAAA KAMTEAIGDE PLGDHVLELQ IAEVVDETDE ARSLVFAVPD     480
GSDDPEIPPR RLRYAPGQFL TLRVPSERTG SVARCYSLCS SPYTDDALAV TVKRTADGYA     540
SNWLCDHAQV GMRIHVLAPS GNFVPTTLDA DFLLLAAGSG ITPIMSICKS ALAEGGGQVT     600
LLYANRDDRS VIFGDALREL AAKYPDRLTV LHWLESLQGL PSASALAKLV APYTDRPVFI     660
CGPGPFMQAA RDALAALKVP AQQVHIEVFK SLESDPFAAV KVDDSGDEAP ATAVVELDGQ     720
THTVSWPRTA KLLDVLLAAG LDAPFSCREG HCGACACTLR AGKVNMGVND VLEQQDLDEG     780
LILACQSRPE SDSVEVTYDE                                                800

SEQ ID NO: 17              moltype = AA  length = 830
FEATURE                    Location/Qualifiers
source                     1..830
                           mol_type = protein
```

```
                      organism = synthetic construct
SEQUENCE: 17
MQLLLEQIWG FLTAHPISVV TTILIVYLIH ITLKPLNRVR RLGDVGLFFG KPELKGFYRE    60
RQLERLKLLR RVGDMPPVFP NGWYCVCESE KLANNQIMEI TVLGQFLSLI RSESGAVYIT   120
DSYCPHIGAN FNIGGRVVRD NCIQCPFHGW IFSAETGKCV EVPYDEGRIP EQAKVTTWPC   180
IERNNNIYLW YHCDGAEPEW EIPEITEITD GFWHLGGRTE HEVMCHIQEI PENGADIAHL   240
NYLHKSAPPV TKGSDIIKTD LSDPQPAVQH VWDGKWEVKS EEDRHCGVMH LNQFMTFWGY   300
KVPLTSSKLV AEQHGPGIVH MLFDFGIWGK GVVFQTVTPE EALLQRVRFR IFSNIPWFFV   360
KFFMTVEAMQ FERDVFIWSN KKYIKSPLLV KNDGPIQKHR RWFSQFYTEN SPKMLKDGSL   420
SNQAKSIFDW AAALEHHHHH HGGGGSGGGG SGGGGSHHHH HHSSGLVPRG SHMTEAIGDE   480
PLGDHVLELQ IAEVVDETDE ARSLVFAVPD GSDDPEIPPR RLRYAPGQFL TLRVPSERTG   540
SVARCYSLCS SPYTDDALAV TVKRTADGYA SNWLCDHAQV GMRIHVLAPS GNFVPTTLDA   600
DPFLLLAAGSG ITPIMSICKS ALAEGGGQVT LLYANRDDRS VIFGDALREL AAKYPDRLTV   660
LHWLESLQGL PSASALAKLV APYTDRPVFI CGPGPFMQAA RDALAALKVP AQQVHIEVFK   720
SLESDPFAAV KVDDSGDEAP ATAVVELDGQ THTVSWPRTA KLLDVLLAAG LDAPFSCREG   780
HCGACACTLR AGKVNMGVND VLEQQDLDEG LILACQSRPE SDSVEVTYDE              830

SEQ ID NO: 18            moltype = AA  length = 827
FEATURE                  Location/Qualifiers
source                   1..827
                         mol_type = protein
                         organism = synthetic construct
SEQUENCE: 18
MQLLLEQIWG FLTAHPISVV TTILIVYLIH ITLKPLNRVR RLGDVGLFFG KPELKGFYRE    60
RQLERLKLLR RVGDMPPVFP NGWYCVCESE KLANNQIMEI TVLGQFLSLI RSESGAVYIT   120
DSYCPHIGAN FNIGGRVVRD NCIQCPFHGW IFSAETGKCV EVPYDEGRIP EQAKVTTWPC   180
IERNNNIYLW YHCDGAEPEW EIPEITEITD GFWHLGGRTE HEVMCHIQEI PENGADIAHL   240
NYLHKSAPPV TKGSDIIKTD LSDPQPAVQH VWDGKWEVKS EEDRHCGVMH LNQFMTFWGY   300
KVPLTSSKLV AEQHGPGIVH MLFDFGIWGK GVVFQTVTPE EALLQRVRFR IFSNIPWFFV   360
KFFMTVEAMQ FERDVFIWSN KKYIKSPLLV KNDGPIQKHR RWFSQFYTEN SPKMLKDGSL   420
SNQAKSIFDW AAALEHHHHH HAEAAAKEAA AKAHHHHHHS SGLVPRGSHM TEAIGDEPLG   480
DHVLELQIAE VVDETDEARS LVFAVPDGSD DPEIPPRRLR YAPGQFLTLR VPSERTGSVA   540
RCYSLCSSPY TDDALAVTVK RTADGYASNW LCDHAQVGMR IHVLAPSGNF VPTTLDADFL   600
LLAAGSGITP IMSICKSALA EGGGQVTLLY ANRDDRSVIF GDALRELAAK YPDRLTVLHW   660
LESLQGLPSA SALAKLVAPY TDRPVFICGP GPFMQAARDA LAALKVPAQQ VHIEVFKSLE   720
SDPFAAVKVD DSGDEAPATA VVELDGQTHT VSWPRTAKLL DVLLAAGLDA PFSCREGHCG   780
ACACTLRAGK VNMGVNDVLE QQDLDEGLIL ACQSRPESDS VEVTYDE                 827

SEQ ID NO: 19            moltype = DNA  length = 2412
FEATURE                  Location/Qualifiers
source                   1..2412
                         mol_type = other DNA
                         organism = synthetic construct
SEQUENCE: 19
atgcagcttt tgttggagca aatctggggt ttcctgactg cacatccaat cagtgtagtc    60
acgacgattt taatcgtata tttaatccac attacgctga agccgctgaa tcgtgtgcgt   120
cgtttgggg acgtgggctt ttcttcggc aagcccgaat tgaagggttt ctaccgtgag   180
cgtcagctgg aacgcctgaa acttttcgcg cgtgtgggag atatgccacc tgtatttccc   240
aacggttggt attgtgtttg cgaatcggag aaactggcta acaatcagat catgaaaatt   300
acagtttag gtcagttctt aagccttatt cgtagcgaat ctggtgcggt ttacattaca   360
gattcttact gtccgcacat tggtgcgaac ttcaatatcg gcgggcgtgt ggttcgcgta   420
aactgtatcc agtgtccctt ccatgggtgg atttttctctg ccgagaccgg gaaatgcgta   480
gaagtgccct atgatgaagg acgcatccct gaacaggcaa aggtcaccac ctggccgtgc   540
atcgaacgca acaacaacat ctatttatgg tatcactgtg atggggcgga gcctgaatgg   600
gaaatcccgg aaatcacaga aatcactgac ggctttttggc atctggggggg acgtacagaa   660
catgaggtaa tgtgccatat tcaagagatc cctgagaacg gagctgccca tgccacttta   720
aattatttac acaagtctgc ccccccgta actaaaggta gcgatatcat caagacagat   780
ttgtctgacc cgcagcctgc tgtccagcat gtatgggacg gtaaatggga agttaagagt   840
gaagaagacc gccattgtgg tgttatgcat ctgaaccagt tcatgacatt tgggggttat   900
aaggtccct tgaccagctc taagttggtg gcagaacagc atggcccagg catcgtgcat   960
atgttgtttg atttcggtat tggggaaaa ggggtggtgt tccaaacggt tacacccgag  1020
gaagcattgt tgcagcgtgt acgtttccgc atcttttcga atatcccttg gttcttcgtc  1080
aagttctta tgaccgtcga agcaatgcaa ttgaacgcg atgtgttcat ctggagtaac  1140
aagaaaatata ttaagtcacc cctgttggtc aagaacgatg gccccatcca gaaacatcgt  1200
cgctggttta gccaattcta taccgagaac tcaccgaaaa tgctgaagga tggatctctt  1260
tctaaccagg cgaagtccat cttcgattgg ggaggcggtg gtcaggagg tggtggatct  1320
ggcggaggtg gtagtatgac tgaggcgata ggcgatgaac cactgggaga tcatgtcttg  1380
gaacttcaga tagcggaagt tgtagatgag actgacgagg cgcggagttt agtatttgca  1440
gtccctgacg ggtcggacga ccctgaaata ccgccacggc gcctgcggta tgcgccaggc  1500
cagttcttaa cgctgcgggt ccctagcgag cgcaccggca gttgttgctcg ttgctacagc  1560
ctgtgctcct ccccatatac cgatgacgca ttagctgtta ctgtaaagcg tactgctgat  1620
gggtatgcca gtaattggtt atgtgatcat gcccaagtcg gaatgcgcat tcacgttctg  1680
gcccttcgg ggaattcgt tccaacgaca ttggatgctg actttttgct tctgccgct  1740
ggatcccca tcactcccat tatgagtatt tgcaaaagtg cgttggcgga aggcgggggga  1800
caagtaacat tgctctacgc taatcgggat gacagatcag tgattttttgg cgacgcctta  1860
cgcgagttgg cggcgaagta cccggaccgc ttaacagtat tacactggct gaatctcttt  1920
caaggtttgc cgtcagcgtc ggccttagcc aaattggttg ctccatatac ggaccgtcca  1980
gttttcatct gtggtccagg tccctttatg caagccgccc gggatgccct tgcggcattg  2040
aaggtgccag cacagcaggt tcatatagag gtattcaagt cccttgaatc agaccgttc  2100
```

```
gcggctgtta aggtcgacga cagtggcgat gaggcaccag ccactgctgt tgtggagttg   2160
gatggtcaga ctcatacggt gagttggcct agaacggcga aattattgga tgtccttctt   2220
gcggcgggac ttgacgctcc gttctcgtgc cgtgaggggc attgtggagc ttgtgcgtgc   2280
actttgcggg caggcaaggt caatatgggg gtcaatgacg tgctggagca gcaggacctt   2340
gacgagggat taattttggc atgtcagtcc cgtcccgaat cggactccgt tgaggtgacc   2400
tatgacgagt aa                                                       2412

SEQ ID NO: 20           moltype = DNA  length = 2403
FEATURE                 Location/Qualifiers
source                  1..2403
                        mol_type = other DNA
                        organism = synthetic construct
SEQUENCE: 20
atgcagcttt tgttggagca aatctggggt ttcctgactg cacatccaat cagtgtagtc     60
acgacgattt taatcgtata tttaatccac attacgctga agccgctgaa tcgtgtgcgt    120
cgtttggggg acgtgggctt attcttcggc aagcccgaat tgaagggttt ctaccgtgag    180
cgtcagctgg aacgcctgaa acttttgcgc cgtgtgggag atatgccacc tgtatttccc    240
aacggttggt attgtgtttg cgaatcggag aaactggcta acaatcagat catggaaatt    300
acagttttag gtcagttctt aagccttatt cgtagcgaat ctggtgcggt ttacattaca    360
gattcttact gtccgcacat tggtgcgaac ttcaatatcg gcgggcgtgt ggttcgcgat    420
aactgtatcc agtgtccctt ccatggggtgg attttctctg ccgagaccgg gaaatgcgta    480
gaagtgccct atgatgaagg acgcatccct gaacaggcaa aggtcaccac ctggccgtgc    540
atcgaacgca acaacaacat ctatttatgg tatcactgtg atggggcgga gcctgaatgg    600
gaaatcccgg aaatcacaga aatcactgac ggcttttggc atctgggggg acgtacagaa    660
catgaggtaa tgtgccatat tcaagagatc cctgagaacg gagctgacat tgcgcactta    720
aattatttac acaagtctgc ccccccgta actaaaggta gcgatatcat caagacagat    780
ttgtctgacc cgcagcctgc tgtccagcat gtatgggacg gtaaatggga agttaagagt    840
gaagaagacc gccattgtgg tgttatgcat ctgaaccagt tcatgacatt tgggggttat    900
aaggtcccct tgaccagctc taagttggtg gcagaacagc atggcccagg catcgtgcat    960
atgttgtttg atttcggtat ttggggaaaa ggggtggtgt tccaaacggt tacacccgag   1020
gaagcattgt tgcagcgtgt acgtttccgc atcttttcga atatcccttg gttcttcgtc   1080
aagttcttta tgaccgtcga agcaatgcaa tttgaacgcg atgtgttcat ctggagtaac   1140
aagaaatata ttaagtcacc cctgttggtc aagaacgatg gccccatcca gaaacatcgt   1200
cgctggttta gccaattcta taccgagaac tcaccgaaca tgctgaagga tggatctctt   1260
tctaaccagg cgaagtccat cttcgattgg gctgaggctg cagccaaaga agcggcggct   1320
aaggcgatga ctgaggcgat aggcgatgaa ccactgggag atcatgtctt ggaacttcag   1380
atagcggaag ttgtagatga gactgacgag gcgcggagtt tagtatttgc agtccctgac   1440
gggtcggacg accctgaaat accgccacgg cgcctgcggt atgcgccagg ccagttctta   1500
acgctggtga tcctagccga gcgcaccggc agtgttgctc gttgctacag cctgtgctcc   1560
tccccatata ccgatgacgc attagctgtt actgtaaagc gtactgctga tgggtatgcc   1620
agtaattggt tatgtgatca tgccaagtcc ggaatgcgca ttcacgttct ggccccttcg   1680
gggaatttcg ttccaacgac attggatgct gactttttgc ttctgccgcc tggatcgggg   1740
atcactccca ttatgagtat ttgcaaaagt gcgttggcgg aaggcggcgg gcaagtaaca   1800
ttgctgtacg ctaatcggga tgacagatca gtgattttg gcgacgcctt acgcgagttg   1860
gcggcgaagt acccggaccg cttaacagta ttacactggc ttgaatctct tcaaggtttg   1920
ccgtcagcgt cggccttagc caaattggtt gctccatata cggaccgtcc agttttcatc   1980
tgtggtccag gtccctttat gcaagccgcc cgggatgccc ttgcggcatt gaaggtgcca   2040
gcacagcagg ttcatataga ggtattcaag tcccttgaat cagacccgtt cgcggctgtt   2100
aaggtcgacg acagtggcga tgaggcacca gccactgctg ttgtggagtt ggatggtcag   2160
actcatacgg tgagttggcc tagaacggcg aaattattgg atgtccttct gcggcggga   2220
cttgacgctc cgttctcgtg ccgtgagggg cattgtggag cttgtgcgtg cacttttcgg   2280
gcaggcaagg tcaatatggg ggtcaatgac gtgctggagc agcaggacct tgacgaggga   2340
ttaattttgg catgtcagtc ccgtcccgaa tcggactccg ttgaggtgac ctatgacgag   2400
taa                                                                 2403

SEQ ID NO: 21           moltype = DNA  length = 2484
FEATURE                 Location/Qualifiers
source                  1..2484
                        mol_type = other DNA
                        organism = synthetic construct
SEQUENCE: 21
atgcagcttt tgttggagca aatctggggt ttcctgactg cacatccaat cagtgtagtc     60
acgacgattt taatcgtata tttaatccac attacgctga agccgctgaa tcgtgtgcgt    120
cgtttggggg acgtgggctt attcttcggc aagcccgaat tgaagggttt ctaccgtgag    180
cgtcagctgg aacgcctgaa acttttgcgc cgtgtgggag atatgccacc tgtatttccc    240
aacggttggt attgtgtttg cgaatcggag aaactggcta acaatcagat catggaaatt    300
acagttttag gtcagttctt aagccttatt cgtagcgaat ctggtgcggt ttacattaca    360
gattcttact gtccgcacat tggtgcgaac ttcaatatcg gcgggcgtgt ggttcgcgat    420
aactgtatcc agtgtccctt ccatggggtgg attttctctg ccgagaccgg gaaatgcgta    480
gaagtgccct atgatgaagg acgcatccct gaacaggcaa aggtcaccac ctggccgtgc    540
atcgaacgca acaacaacat ctatttatgg tatcactgtg atggggcgga gcctgaatgg    600
gaaatcccgg aaatcacaga aatcactgac ggcttttggc atctgggggg acgtacagaa    660
catgaggtaa tgtgccatat tcaagagatc cctgagaacg gagctgacat tgcgcactta    720
aattatttac acaagtctgc ccccccgta actaaaggta gcgatatcat caagacagat    780
ttgtctgacc cgcagcctgc tgtccagcat gtatgggacg gtaaatggga agttaagagt    840
gaagaagacc gccattgtgg tgttatgcat ctgaaccagt tcatgacatt tgggggttat    900
aaggtcccct tgaccagctc taagttggtg gcagaacagc atggcccagg catcgtgcat    960
atgttgtttg atttcggtat ttggggaaaa ggggtggtgt tccaaacggt tacacccgag   1020
gaagcattgt tgcagcgtgt acgtttccgc atcttttcga atatcccttg gttcttcgtc   1080
```

-continued

```
aagttcttta tgaccgtcga agcaatgcaa tttgaacgcg atgtgttcat ctggagtaac   1140
aagaaatata ttaagtcacc cctgttggtc aagaacgatg gccccatcca gaaacatcgt   1200
cgctggttta gccaattcta taccgagaac tcaccgaaaa tgctgaagga tggatctctt   1260
tctaaccagg cgaagtccat cttcgattgg gcggccgcac tcgagcatca ccatcaccat   1320
cacgctgagg ctgcagccaa agaagcggcg gctaaggcag atcatcatca tcatcacagc   1380
agcggcctgg tgccgcgcgg cagccatatg actgaggcga taggcgatga accactggga   1440
gatcatgtct tggaacttca gatagcggaa gttgtagatg agactgacga ggcgcggagt   1500
ttagtatttg cagtccctga cgggtcggac gaccctgaaa taccgccacg cgcctgcgg    1560
tatgcgccag gccagttctt aacgctgcgg gtccctagcg agcgcaccgg cagtgttgct   1620
cgttgctaca gcctgtgctc ctccccatat accgatacg cattagctgt tactgtaaag    1680
cgtactgctg atgggtatgc cagtaattgg ttatgtgatc atgcccaagt cggaatgcgc   1740
attcacgttc tggccccttc ggggaatttc gttccaacga cattggatgc tgactttttg   1800
cttctggccg ctggatcggg gatcactccc attatgagta tttgcaaaag tgcgttggcg   1860
gaaggcgcg ggcaagtaac attgctgtac gctaatcggg atgacagatc agtgattttt    1920
ggcgacgcct tacgcgagtt ggcggcgaag taccccggacc gcttaacagt attacactgg  1980
cttgaatctc ttcaaggttt gccgtcagcg tcggccttag ccaaattggt tgctccatat   2040
acggaccgtc cagttttcat ctgtggtcca ggtccctta tgcaagccgc ccgggatgcc    2100
cttgcggcat tgaaggtgcc agcacagcag gttcatatag aggtattcaa gtcccttgaa   2160
tcagacccgt tcgcgctgt taaggtcgac gacagtggcg atgaggcacc agccactgct    2220
gttgtggagt tggatggtca gactcatacg gtgagttggc ctagaacggc gaaattattg   2280
gatgtccttc ttgcggcggg acttgacgct ccgttctcgt gccgtgaggg gcattgtgga   2340
gcttgtgcgt gcactttgcg ggcaggcaag gtcaatatgg gggtcaatga cgtgctgag    2400
cagcaggacc ttgacgaggg attaattttg gcatgtcagt cccgtcccga atcggactcc   2460
gttgaggtga cctatgacga gtaa                                          2484
```

SEQ ID NO: 22   moltype = DNA  length = 36
FEATURE     Location/Qualifiers
source      1..36
         mol_type = other DNA
         organism = synthetic construct
SEQUENCE: 22
gctgaggctg cagccaaaga agcggcggct aaggcg         36

SEQ ID NO: 23   moltype = DNA  length = 45
FEATURE     Location/Qualifiers
source      1..45
         mol_type = other DNA
         organism = synthetic construct
SEQUENCE: 23
ggaggcggtg ggtcaggagg tggtggatct ggcggaggtg gtagt      45

SEQ ID NO: 24   moltype = AA  length = 12
FEATURE     Location/Qualifiers
source      1..12
         mol_type = protein
         organism = synthetic construct
SEQUENCE: 24
AEAAAKEAAA KA                   12

SEQ ID NO: 25   moltype = AA  length = 15
FEATURE     Location/Qualifiers
source      1..15
         mol_type = protein
         organism = synthetic construct
SEQUENCE: 25
GGGGSGGGGS GGGGS                 15

SEQ ID NO: 26   moltype = AA  length = 429
FEATURE     Location/Qualifiers
source      1..429
         mol_type = protein
         organism = Drosophila melanogaster
SEQUENCE: 26
MTSYSLFWMS LLKNNWKPIS NDFVICLWTL AVTFIRIYWI FFVPLEWKKD LDNEKWSFLR    60
KTENVVCYNH KRDTINRLRK LKIQKIIELP PPYPNGWYGI LKSSQLKAGE ATCVSCLGED   120
LVIFRSKKDI VFILDAYCPH LGANLGIGGS VADDCVICPF HQWKFRGTDG LCINIPYSTS   180
VPKGSKLKKW ISQEVDGFIF IWYHAEQTEL PWDLPVPMGE IDDTFVYHGH NEFYINCHIQ   240
EIPENGADIA HFNAIHKKNF INGSWAQKKR LFGLGSHHWK ARWSPFTGKL KYLAEVNLSH   300
TFKLFGKFGC FRMEVSGKQI GPSIVCLEVN SYTFGKIKVF QYITPIEPML QKVVHEFYGP   360
RWIAPLMKIF IYGESLMFER DIKIWNHKVF NRNPILAKED ASIKKFRLWF SQFYSSNSKI   420
YSEATNIGW                                                          429

SEQ ID NO: 27   moltype = AA  length = 453
FEATURE     Location/Qualifiers
source      1..453
         mol_type = protein
         note = Tetrahymena thermophila
         organism = unidentified
SEQUENCE: 27

```
MIEFNKECLM DILKNQDYHF YMVIPLIFIG LYALYIKKFK YYNPIEKQEW DDRRSNVKRG    60
NPPPSYPNGW FRVCHKNELQ IGQSKFFKLN GRHITVFRGE DGIPYALHAY CSHMGANLGI   120
GGKVKWNSCI ECPFHGWSFD GKSGKCVNSE HLDEKQCTHH TYHDIKKMTK GSDNRYIKTC   180
ESGSPSQIQK FHVRQQNNLI YVWFHAKNVD PYYEPFEINE IPYLEDRGET ADYVNCQIQE   240
IPENGADFKH FEYVHYAWIE ILFPWIKFKW VPKDRKPTDK DFDEVMRTHP NKKVQAFSNK   300
LFDKYTNEQN KTHINNLVLD AYLVFFDKFE FYIQTATVFQ LGSGTVFLFL KFPLWEAVVV   360
QSVTPVGKFN QLVHHKMYTS WWLPYWVSAY LLAGFRKQFI SDKIVWNNKI FADKLTYNPK   420
AVFDERLLNW REWYSQYYEG CDEFEKNQEA FDW                                453

SEQ ID NO: 28           moltype = AA   length = 453
FEATURE                 Location/Qualifiers
source                  1..453
                        mol_type = protein
                        organism = Bombyx mori
SEQUENCE: 28
MADRQHFPSA ITEAVSSNTA CPDTGPKAET TNIFLLLQRN ITIESSKHVF SSIVEYILIL    60
TLMFAFSAIL YVIYKSYISP VFYKKELTEV GFDHIPQGPD KGRRISRAQA SRRMGSKLPP   120
PYPNGWFAVA ETRELKVGSV LSIDALGQNL CVYRGEDGLA RCVDAYCPHL GANLAVGGTV   180
RGSCIECPFH KWRFNAAGTC VSLPGSDIAP KGVSIRTWCV VETDGAIWIW HDAEGREPLW   240
EITDPPELKD FGYRGRNEFE VSAHIQEIPE NGADVPHLNA VHSSSLLSDL GERYPVLHEI   300
IGRHVWNADW TKSDDHTSLM HITQEYKVLK YDLARIDVKV TQIGPGHVRL FLKTSVGPFY   360
IAQSVTPLGP LLQKVIHRVY SPAYNAPVGA FLVRCEAYMF ERDVTIWNSK RFVSAPAYVK   420
TDKTIRTFRN WFGQFYSEHS LSFRDALQNP LDW                                453

SEQ ID NO: 29           moltype = AA   length = 315
FEATURE                 Location/Qualifiers
source                  1..315
                        mol_type = protein
                        organism = Pseudomonas putida
SEQUENCE: 29
MIDAVVVSRN DEAQDICSFE LAAVDGSLLR FSAGAHIDVH LPEGQVRQYS LCNHPEERHR    60
YLIGVLKDPA SRGGSRSLHE QIHNGARLRI SAPRNLFPLA QGARRSLLFA GGIGITPILC   120
MAEQLAASAD FELHYCARSS ERAAFIERMR GAAFADRLFV HFDEQPETAL DIAQVLANPQ   180
ADVHLYVCGP GGFMQHVLES AKAQGWQEAC LHREYFAAAP VDTQGDGSFS VQLNSTGQVF   240
EVPADQSVVH VLEQHGIAIA MSCEQGICGT CLTRVLSGTP EASRPVFLTE QEQALNDQFT   300
PCCSRSKTPL LVLDL                                                   315

SEQ ID NO: 30           moltype = AA   length = 346
FEATURE                 Location/Qualifiers
source                  1..346
                        mol_type = protein
                        organism = Rhodococcus erythropolis
SEQUENCE: 30
MTTVEVPHSS RSAVLTVSGV IEETSDARSL VFEIPAELKD KFDYKPGQFL TLRIPSDQTG    60
SVARCYSLAS SPFTDDAPKV TVKRTVDGYG SNWLCDKLQV GDTIEVLPPS GVFTPKSLDH   120
DFLLFGAGSG ITPVISILKS ALTQGSGNVV LIYANRDEKS VIFGAELREL AAQHPGRLTV   180
VHWIETVQGL PAVSQLATLA KPFVAYEAFM CGPGPFMDAV HKALAEAGMP RTQVHAEVFN   240
SLAGDPFRDV EVAEVSDEEA ADAATVEVEL DGETHTLVWP RKQTLVDIML AKGLDVPYSC   300
KEGESGSCAC TVTEGEVQMD NSEILDAEDV ANGYILGCKR SRSPIA                  346

SEQ ID NO: 31           moltype = AA   length = 351
FEATURE                 Location/Qualifiers
source                  1..351
                        mol_type = protein
                        organism = Rhodococcus rhodochrous
SEQUENCE: 31
MTTVEVPHGS RSVILTVSAV VEETADTRSI VFAVPDELRD KFAYRPGQFL TLRIPSDRTG    60
SVARCYSLAS SPFTDDAPKV TVKRTSDGYG SNWLCDNIAT GQTLEVLPPA GVFTPKSLDH   120
DFLLFGAGSG ITPVISILKS ALTQGGGKVV LVYANRDEKS VIFAEELRAL AEKYPTRLTV   180
VHWLESVQGL PTADQLAAIA APYESYEAFM CGPGPFMDTV HQALNTVGMP RARVHAEVFN   240
SLSGDPFADQ APVEVSDEDA ADAATVEVEL DGEVHKLSWP RKQTLVDIML AKGIDVPYSC   300
QEGECGSCAC TVLEGKVEME NCDVLDPEDI EAGYILGCQA RPVTDHLKIE F            351

SEQ ID NO: 32           moltype = DNA   length = 1287
FEATURE                 Location/Qualifiers
source                  1..1287
                        mol_type = other DNA
                        organism = synthetic construct
SEQUENCE: 32
atgttgttgg agcaaatctg ggtttcctg actgcacatc caatcagtgt agtcacgacg     60
attttaatcg tatatttaat ccacattacg ctgaagccgc tgaatcgtgt gcgtcgtttg   120
ggggacgtgg gcttattctt cggcaagccc gaattgaagg ttttctaccg tgagcgtcag   180
ctggaacgcc tgaaactttt gcgccgtgtg ggagatatgc cacctgtatt tcccaacggt   240
tggtattgtg tttgcgaatc ggagaaactg gctaacatc agatcatgga aattacagtt   300
ttaggtcagt tcttaagcct tattcgtagc gaatctggtg cggtttacat tacagattct   360
tactgtccgc acattggtgc gaacttcaat atcggcgggc gtgtggttcg cgataactgt   420
atccagtgtc ccttccatgg gtggattttc tctgccgaga ccgggaaatg cgtagaagtg   480
ccctatgatg aaggacgcat ccctgaacag gcaaaggtca ccacctggcc gtgcatcgaa   540
cgcaacaaca acatctattt tatggtatcac tgtgatgggg cggagcctga atgggaaatc   600
```

```
ccggaaatca cagaaatcac tgacggcttt tggcatctgg ggggacgtac agaacatgag  660
gtaatgtgcc atattcaaga gatccctgag aacggagctg acattgcgca cttaaattat  720
ttacacaagt ctgccccccc cgtaactaaa ggtagcgata tcatcaagac agatttgtct  780
gacccgcagc ctgctgtcca gcatgtatgg gacggtaaat gggaagttaa gagtgaagaa  840
gaccgccatt gtggtgttat gcatctgaac cagttcatga cattttgggg ttataaggtc  900
cccttgacca gctctaagtt ggtggcagaa cagcatggcc caggcatcgt gcatatgttg  960
tttgatttcg gtatttgggg aaaaggggtg tgttccaaa cggttacacc cgaggaagca  1020
ttgttgcagc gtgtacgttt ccgcatcttt tcgaatatcc cttggttctt cgtcaagttc  1080
tttatgaccg tcgaagcaat gcaatttgaa cgcgatgtgt tcatctggag taacaagaaa  1140
tatattaagt caccccctgtt ggtcaagaac gatggcccca tccagaaaca tcgtcgctgg  1200
tttagccaat tctataccga gaactcaccg aaaatgctga aggatggatc tctttctaac  1260
caggcgaagt ccatcttcga ttggtaa                                       1287

SEQ ID NO: 33         moltype = DNA  length = 1077
FEATURE               Location/Qualifiers
source                1..1077
                      mol_type = other DNA
                      organism = synthetic construct
SEQUENCE: 33
atgactgagg cgataggcga tgaaccactg ggagatcatg tcttggaact tcagatagcg   60
gaagttgtag atgagactga cgaggcgcgg agtttagtat ttgcagtccc tgacgggtcg  120
gacgaccctg aaataccgcc acggcgcctg cggtatgcgc caggccagtt cttaacgctg  180
cgggtcccta cgagcgcac cggcagtgtt gctcgttgct acagcctgtg ctcctcccca  240
tataccgatg acgcattagc tgttactgta aagcgtactg ctgatgggta tgccagtaat  300
tggttatgtg atcatgccca gtcggaatg cgcattcacg ttctggcccc ttcggggaat  360
ttcgttccaa cgacattgga tgctgacttt ttgcttctgg gggatcact  420
cccattatga gtatttgcaa aagtgcgttg gcgaaggcg gcgggcaagt aacattgctg  480
tacgctaatc gggatgacag atcagtgatt tttggcgacg cctacgcga gttggcggcg  540
aagtacccgg accgcttaac agtattacac tggcttgaat ctcttcaagg tttgccgtca  600
gcgtcggcct tagccaaatt ggttgctcca tatacggacc gtccagtttt catctgtggt  660
ccaggtccct ttatgcaagc cgcccgggat gcccttgcgg cattgaaggt gccagcacag  720
caggttcata tagaggtatt caagtcccctt gaatcagacc cgttcgcggc tgttaaggtc  780
gacgacagtg gcgatgaggc accagccact gctgttgtgg agttggatgg tcagactcat  840
acggtgagtt ggcctagaac ggcgaaatta ttggatgtcc ttcttgcggc gggacttgac  900
gctccgttct cgtgccgtga gggggcattgt ggagcttgtg cgtgcgcaggc  960
aaggtcaata tgggggtcaa tgacgtgctg gagcagcagg accttgacga gggattaatt 1020
ttggcatgtc agtcccgtcc cgaatcggac tccgttgagg tgacctatga cgagtaa    1077

SEQ ID NO: 34         moltype = DNA  length = 2493
FEATURE               Location/Qualifiers
source                1..2493
                      mol_type = other DNA
                      organism = synthetic construct
SEQUENCE: 34
atgcagcttt tgttggagca aatctggggt ttcctgactg cacatccaat cagtgtagtc   60
acgacgattt taatcgtata tttaatccac attacgctga agccgctgaa tcgtgtgcgt  120
cgtttggggg acgtgggctt attcttcggc aagcccaagtt tgaagggttt ctaccgtgag  180
cgtcagctgg aacgcctgaa acttttgcgc cgtgtgggag atatgccacc tgtatttccc  240
aacggttggt attgtgtttg cgaatcggag aaactggcta acaatcagat catgaaaatt  300
acagtttag gtcagttctt aagccttatt cgtagcgaat ctggtgcggt ttacattaca  360
gattcttact gtccgcacat tggtgcgaac ttcaatatcg gcgggcgtgt ggttcgcgat  420
aactgtatcc agtgtcccctt ccatgggtgg attttctctg ccgagaccgg gaaatgcgta  480
gaagtgccct atgatgaagg acgcatccct gaacaggcaa aggtcaccac ctggccgtgc  540
atcgaacgca acaacaacat ctatttatgg tatcactgtg atggggcgga gcctgaatgg  600
gaaatcccgg aaatcacaga aatcactgac ggcttttgc atctggggg acgtacagaa  660
catgaggtaa tgtgccatat tcaagagatc cctgagaacg gagctgacat tgcgcactta  720
aattattac acaagtctgc cccccccgta actaaaggta gcgatatcat caagacagat  780
ttgtctgacc cgcagcctgc tgtccagcat gtatgggacg gtaaatgga gttaagagt  840
gaagaagacc gccattgtgg tgttatgcat ctgaaccagt tcatgacatt tggggttat  900
aaggtcccct tgaccagctc taagttggtg gcagaacagc atggcccagg catcgtgcat  960
atgttgtttg atttcggtat ttggggaaaa ggggtggtgt tccaaacggt tacacccgag 1020
gaagcattgt tgcagcgtgt acgtttccgc atcttttcga atatcccttg gttcttcgtc 1080
aagttcttta tgaccgtcga agcaatgcaa tttgaacgcg atgtgttcat ctggagtaac 1140
aagaaatata ttaagtcacc cctgttggtc aagaacgatg gccccatcca gaaacatcgt 1200
cgctggttta gccaattcta taccgagaac tcaccgaaaa tgctgaagga tggatctctt 1260
tctaaccagg cgaagtccat cttcgattgg cggccgcac tcgagcatca ccatcaccat 1320
cacgaggcg tgggtcagg aggtggtgga tctggcggag tggtagtca tcatcatcat 1380
catcacagca gcggccctggt gccgcgcgg agccatatga ctgaggcgat aggcgatgaa 1440
ccactgggga tcatgtctt ggaacttcag atacggaag ttgtagatga gactgacgag 1500
gcgcggagtt tagtatttgc agtccctgac gggtcggacg accctgaaat accgccacgg 1560
cgcctgcggt atgcgccagg ccagttctta acgctgcggg tccctagcga gcgcaccggc 1620
agtgttgctc gttgctacag cctgtgctcc tccccatata ccgatgacgc attagctgtt 1680
actgtaaagc gtactgctga tgggtatgcc agtaattggt tatgtgatca tgcccaagtc 1740
ggaatgcgca ttcacgttct ggccccttct ggccccttcg ggaattgcca acgac attggatgct 1800
gacttttgt tctgccgc tggatcgggg atcactccca ttatgagtat ttgcaaaagt 1860
gcgttggcgg aagcggcgg gcaagtaaca ttgctgtacg ctaatcggga tgacagatca 1920
gtgattttg cgacgcctt acgcgagttg gcggcgaagt acccgaccg cttaacagta 1980
ttacactggc ttgaatctct tcaaggtttg ccgtcagcgt cggccttagc caaattggtt 2040
gctccatata cggaccgtcc agttttcatc tgtggtccag gtcccttttat gcaagccgcc 2100
```

```
cgggatgccc ttgcggcatt gaaggtgcca gcacagcagg ttcatataga ggtattcaag    2160
tcccttgaat cagacccgtt cgcggctgtt aaggtcgacg acagtggcga tgaggcacca    2220
gccactgctg ttgtggagtt ggatggtcag actcatacgg tgagttggcc tagaacggcg    2280
aaattattgg atgtccttct tgcggcggga cttgacgctc cgttctcgtg ccgtgagggg    2340
cattgtggag cttgtgcgtg cactttgcgg gcaggcaagg tcaatatggg ggtcaatgac    2400
gtgctggagc agcaggacct tgacgaggga ttaattttgg catgtcagtc ccgtcccgaa    2460
tcggactccg ttgaggtgac ctatgacgag taa                                 2493

SEQ ID NO: 35            moltype = AA  length = 6
FEATURE                  Location/Qualifiers
source                   1..6
                         mol_type = protein
                         organism = synthetic construct
SEQUENCE: 35
HHHHHH                                                                  6
```

What is claimed is:

1. A fusion polypeptide, comprising a first moiety comprising an iron-sulfur protein that can convert cholesterol to 7-dehydrocholesterol (7-DHC), and a second moiety comprising a ferredoxin reductase.

2. The fusion polypeptide of claim 1, wherein the iron-sulfur protein is cholesterol 7-desaturase (C7D).

3. The fusion polypeptide of claim 2, wherein the C7D is derived from *Caenorhabditis elegans* C7D, *Drosophila melanogaster* C7D, *Tetrahymena thermophila* C7D, or *Bombyx mori* C7D.

4. The fusion polypeptide of claim 1, wherein the ferredoxin reductase is derived from *Mycobacterium tuberculosis* 3-ketosteroid-9-alpha-monooxygenase, ferredoxin reductase component (KshB), *Pseudomonas putida* vanillate O-demethylase oxidoreductase (VanB), *Rhodococcus erythropolis* oxygenase reductase (KshB), or *Rhodococcus rhodochrous* 3-ketosteroid-9-alpha-monooxygenase, ferredoxin reductase component (KshB).

5. The fusion polypeptide of claim 1, wherein the first moiety is fused with the second moiety with a linker.

6. The fusion polypeptide of claim 5, wherein the linker is a flexible linker.

7. The fusion polypeptide of claim 5, wherein the linker is a rigid linker.

8. The fusion polypeptide of claim 1, wherein the fusion polypeptide comprises an amino acid sequence that is at least 70% identical to SEQ ID NO: 15, 16, 17, or 18.

9. A polynucleotide comprising a nucleic acid encoding the fusion polypeptide of claim 1.

10. A polynucleotide comprising from 5' end to 3' end:
   (a) a first nucleic acid encoding an iron-sulfur protein that can convert cholesterol to 7-dehydrocholesterol (7-DHC),
   (b) optionally a second nucleic acid encoding a linker; and
   (c) a third nucleic acid encoding a ferredoxin reductase.

11. The polynucleotide of claim 10, wherein the first nucleic acid and the third nucleic acid are codon optimized for *E. coli* expression.

12. A vector comprising the polynucleotide of claim 10.

13. An engineered microbial cell expressing the fusion polypeptide of claim 1.

14. The engineered microbial cell of claim 13, wherein the cell further expresses:
   (a) an alcohol dehydrogenase (ADH), or
   (b) a glucose oxidase.

15. The engineered microbial cell of claim 13, wherein the cell is a bacterial cell.

16. A culture of engineered microbial cells comprising the engineered microbial cell of claim 13.

17. A method for producing 7-DHC, comprising culturing the engineered microbial cell of claim 13 under conditions suitable for producing 7-DHC, optionally wherein the method additionally comprises recovering 7-DHC from the culture.

18. The method of claim 17, wherein the method further comprises adding isopropanol or glucose to the culture.

19. The method of claim 17, wherein the method comprises adding polymyxin B to the culture.

20. The method of claim 17, wherein the 7-DHC can be produced at a concentration of greater than 10 mg/L cholesterol.

* * * * *